United States Patent
Taylor et al.

(10) Patent No.: US 11,919,890 B2
(45) Date of Patent: *Mar. 5, 2024

(54) RIP1 INHIBITORY COMPOUNDS AND METHODS FOR MAKING AND USING THE SAME

(71) Applicant: Rigel Pharmaceuticals, Inc., South San Francisco, CA (US)

(72) Inventors: Vanessa Taylor, San Francisco, CA (US); Jiaxin Yu, Foster City, CA (US); Esteban Masuda, Menlo Park, CA (US); Ihab Darwish, San Carlos, CA (US); Yan Chen, Foster City, CA (US)

(73) Assignee: ;Eli Lilly and Company, Indianapolis, IN (US)

( * ) Notice: Subject to any disclaimer, the term of this patent is extended or adjusted under 35 U.S.C. 154(b) by 274 days.

This patent is subject to a terminal disclaimer.

(21) Appl. No.: 17/210,261

(22) Filed: Mar. 23, 2021

(65) Prior Publication Data

US 2021/0214347 A1 Jul. 15, 2021

Related U.S. Application Data

(63) Continuation of application No. 16/402,103, filed on May 2, 2019, now Pat. No. 10,975,064.

(60) Provisional application No. 62/666,452, filed on May 3, 2018.

(51) Int. Cl.

| C07D 413/12 | (2006.01) |
|---|---|
| A61K 31/553 | (2006.01) |
| A61P 29/00 | (2006.01) |
| A61P 37/02 | (2006.01) |
| C07D 413/14 | (2006.01) |
| C07D 471/10 | (2006.01) |
| C07D 487/08 | (2006.01) |
| C07D 491/107 | (2006.01) |

(52) U.S. Cl.
CPC ......... *C07D 413/14* (2013.01); *C07D 471/10* (2013.01); *C07D 487/08* (2013.01); *C07D 491/107* (2013.01)

(58) Field of Classification Search
CPC .. C07D 413/12; C07D 413/14; A61K 31/553; A61P 29/00; A61P 37/02
See application file for complete search history.

(56) References Cited

U.S. PATENT DOCUMENTS

| 8,658,689 | B2 | 2/2014 | Cuny et al. |
|---|---|---|---|
| 9,556,152 | B2 | 1/2017 | Harris et al. |
| 9,624,202 | B2 | 4/2017 | Jeong |
| 9,815,850 | B2 | 11/2017 | Estrada et al. |
| 9,896,458 | B2 | 2/2018 | Estrada et al. |
| 10,815,206 | B2 | 10/2020 | Masuda et al. |
| 10,975,064 | B2 | 4/2021 | Taylor et al. |
| 10,988,459 | B2 | 4/2021 | Patel et al. |
| 2015/0353533 | A1 | 12/2015 | Bandyopadhyay et al. |
| 2017/0008877 | A1 | 1/2017 | Patel et al. |
| 2017/0226127 | A1 | 8/2017 | Estrada et al. |
| 2021/0069208 | A1 | 3/2021 | Yu et al. |
| 2021/0070735 | A1 | 3/2021 | Bhamidipati et al. |
| 2021/0070743 | A1 | 3/2021 | Chen et al. |
| 2021/0070744 | A1 | 3/2021 | Shaw et al. |
| 2021/0317135 | A1 | 10/2021 | Darwish et al. |

FOREIGN PATENT DOCUMENTS

| WO | WO 2014/125444 | 8/2014 |
|---|---|---|
| WO | WO 2014/145022 | 9/2014 |
| WO | WO 2016/027253 | 2/2016 |
| WO | WO 2016/128936 | 8/2016 |
| WO | WO 2017/064217 | 4/2017 |
| WO | WO 2017/069279 | 4/2017 |
| WO | WO 2017/109724 | 6/2017 |
| WO | WO 2018/073193 | 4/2018 |
| WO | WO 2018/109097 | 6/2018 |
| WO | 2018/154520 A1 | 8/2018 |
| WO | 2020/001420 | 1/2020 |
| WO | 2020/088194 A1 | 5/2020 |

OTHER PUBLICATIONS

Harris et al., "Discovery and Lead-Optimization of 4,5-Dihydropyrazoles as Mono-Kinase Selective, Orally Bioavailable and Efficacious Inhibitors of Receptor Interacting Protein 1 (RIP1) Kinase," Journal of Medicinal Chemistry, pp. 5096-5110, vol. 62, No. 10, (2019).

Harris et al., "DNA-Encoded Library Screening Identifies Benzo[b][1,4]oxazepin-4-ones as Highly Potent and Monoselective Receptor Interacting Protein 1 Kinase Inhibitors" Journal of Medicinal Chemistry 59(5): 2163-2178, Mar. 10, 2016.

Harris et al., "Discovery of a First-in-Class Receptor Interacting Protein 1 (RIP1) Kinase Specific Clinical Candidate (GSK2982772) for the Treatment of Inflammatory Diseases" Journal of Medicinal Chemistry 60:1247-1261, 2017.

Yoshikawa et al., "Discovery of 7-Oxo-2,4,5,7-tetrahydro-6 H-pyrazolo [3,4- C ] pyridine Derivatives as Potent, Orally Available, and Brain-Penetrating Receptor Interacting Protein 1 (RIP1) Kinase Inhibitors: Analysis of Structure-Kinetic Relationships," Journal of Medicinal Chemistry, pp. 2384-2409, vol. 61, No. 6, (2018).

International Search Report issued for International Application No. PCT/US2019/030476 dated Sep. 11, 2019.

International Search Report issued for International Application No. PCT/US2019/030473 dated Jul. 4, 2019.

(Continued)

*Primary Examiner* — Brenda L Coleman
(74) *Attorney, Agent, or Firm* — Gabriel Magallanes

(57) ABSTRACT

Disclosed herein are kinase inhibitory compounds, such as a receptor-interacting protein-1 (RIP1) kinase inhibitor compounds, as well as pharmaceutical compositions and combinations comprising such inhibitory compounds. The disclosed compounds, pharmaceutical compositions, and/or combinations may be used to inhibit a RIP1 kinase in vivo or ex vivo, and also may treat or prevent a kinase-associated disease or condition, particularly a RIP1-associated disease or condition.

18 Claims, No Drawings

(56) References Cited

OTHER PUBLICATIONS

Najjar et al., "Structure guided design of potent and selective ponatinib-based hybrid inhibitors for RIPK1," *Cell Reports*, vol. 10, pp. 1850-1860, Mar. 24, 2015.
Takeda et al., "CETSA quantitatively verifies in vivo target engagement of novel RIPK1 inhibitors in various biospecimens," *Scientific Reports*, vol. 7, Oct. 11, 2017.

RIP1 INHIBITORY COMPOUNDS AND METHODS FOR MAKING AND USING THE SAME

CROSS-REFERENCE TO RELATED APPLICATION

This application is a continuation of U.S. application Ser. No. 16/402,103, filed May 2, 2019, which claims the benefit of the earlier filing date of U.S. Provisional Application No. 62/666,452, filed on May 3, 2018; the entirety of each of these prior applications is incorporated herein by reference.

FIELD

The present disclosure concerns compounds and methods of making and using the compounds, such as for inhibiting receptor-interacting protein-1 kinase ("RIP1"), and for treating diseases and/or conditions related to RIP1.

BACKGROUND

Receptor-interacting protein-1 kinase (referred to herein as "RIP1") belongs to the tyrosine kinase-like family and is a serine/threonine protein kinase involved in innate immune signaling. RIP1 plays a central role in regulating cell signaling and its role in programmed cell death has been linked to various inflammatory diseases, such as inflammatory bowel disease, psoriasis, and other diseases and/or conditions associated with inflammation and/or necroptotic cell death.

SUMMARY

Disclosed herein are compound embodiments having a Formula I

Formula I or a pharmaceutically acceptable salt thereof. A person of ordinary skill in the art will appreciate that compounds within the scope of Formula I also include stereoisomers, N-oxides, tautomers, hydrates, solvates, isotopes, and/or prodrugs thereof.

With reference to Formula I, ring B is 5-membered heteroaryl; L is a $C_{1-10}$aliphatic linker; $R^1$ is $R^a$ or $R^b$ wherein at least one $R^1$ is $R^b$; each of $R^2$ and $R^3$ independently are $R^a$; each $R^4$ and each $R^5$ independently are $R^a$ or $R^b$; $R^a$ is independently for each occurrence H, D, $C_{1-10}$aliphatic, or $C_{1-10}$cycloaliphatic; $R^b$ is independently for each occurrence halogen or —$NR^dR^d$ wherein (i) each $R^d$ independently is $R^a$ or $R^e$; or (ii) two $R^d$ groups together with the nitrogen bound thereto provide a $C_{3-10}$heterocyclic group; $R^e$ is independently for each occurrence —$OR^a$, —$NR^a$, $C_{1-6}$alkyl, $C_{1-6}$haloalkyl, $C_{1-6}$heteroalkyl, $C_{3-6}$cycloalkyl, or two $R^e$ groups join together to provide a $C_{3-10}$heterocyclic group with the $R^b$ group to which the two $R^e$ groups are bound; m is 1 to 4, such as 1, 2, 3, or 4, with particular embodiments being 1 or 2; n is 0, 1 or 2; and p is 0, 1, 2, 3, 4, or 5.

Disclosed compounds may have a structure satisfying the formula below

In any or all of the above embodiments, ring B can have a structure satisfying a formula wherein at least one W is nitrogen, and each remaining W independently is selected from carbon, CH, oxygen, sulfur, nitrogen, or NH, with particular ring B embodiments being a triazole or an oxazole. Suitable exemplary triazoles include any of the following:

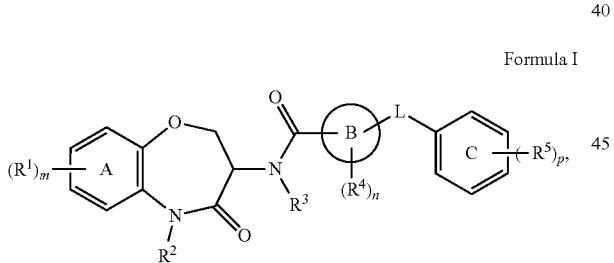

; or

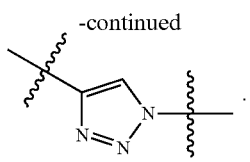

Suitable exemplary oxazoles include any of the following:

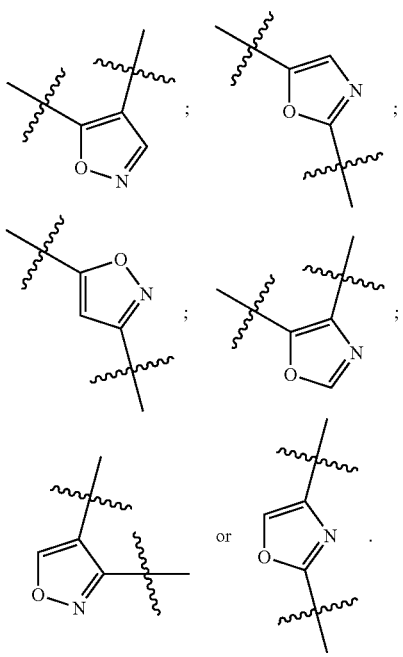

Certain disclosed compounds comprise an $R^5$ group that is an $R^a$ group, wherein $R^a$ is $C_1$-$C_4$aliphatic, or that is an $R^b$ group, wherein $R^b$ is halogen, $R^2$ is $R^a$ wherein $R^a$ is $C_1$-$C_4$aliphatic, and $R^3$ is $R^a$, wherein $R^a$ is hydrogen.

$R^1$ is $R^b$ wherein $R^b$ is —$NR^dR^d$ wherein two $R^d$ groups together with the nitrogen bound thereto provide a $C_{3-10}$heterocyclic group. In some embodiments, $C_{3-10}$heterocyclic group is substituted with one or more $R^e$ groups and/or has one or more additional heteroatoms in addition to the nitrogen to which both $R^d$ groups are bound in certain embodiments. In some embodiments, the $C_{3-10}$heterocyclic group is substituted with two $R^e$ groups that join together to provide a $C_{3-10}$heterocyclic group and this $C_{3-10}$heterocyclic, along with the Rb group can provide a spirocyclic group or a bicyclic group. Certain disclosed spirocyclic groups comprise at least two rings, with each ring having a different number of atoms in the ring. In some embodiments, the spirocyclic group comprises at least two rings, wherein a first ring and a second ring of the spirocyclic group have a different number of carbon atoms, a different number of heteroatoms, or both. In yet additional embodiments, each ring of the spirocyclic group comprises a heteroatom in the ring, and each ring of the spirocyclic group may have a different heteroatom in the ring or the same heteroatom in the ring, such as at least one oxygen atom and at least one nitrogen atom. In some embodiments, the spirocyclic group comprises a first ring comprising a nitrogen atom and a second ring comprising an oxygen atom. The spirocyclic group comprises a first ring coupled to the ring A phenyl group, wherein the first ring has from 3 to 7 atoms and a second ring has from 3 to 7 atoms. Typically, the spirocyclic group comprises greater than 7 total atoms in the spirocyclic system, with some embodiments having a spirocyclic group that comprises 9 total atoms in the spirocyclic system.

The $C_{3-10}$heterocyclic formed by the two $R^e$ groups and the $C_{3-10}$heterocyclic formed by the two $R^d$ groups of $R^b$ may provide a bicyclic group, such as a bicyclic group comprising two or more heteroatoms in the bicyclic group, such as nitrogen and/or oxygen. The bicyclic group may be attached to the ring A phenyl group through a nitrogen atom of the bicyclic group. In some embodiments, the bicyclic group may be a fused bicyclic group or a bridged bicyclic group.

In any or all of the above embodiments, $R^1$ is selected from

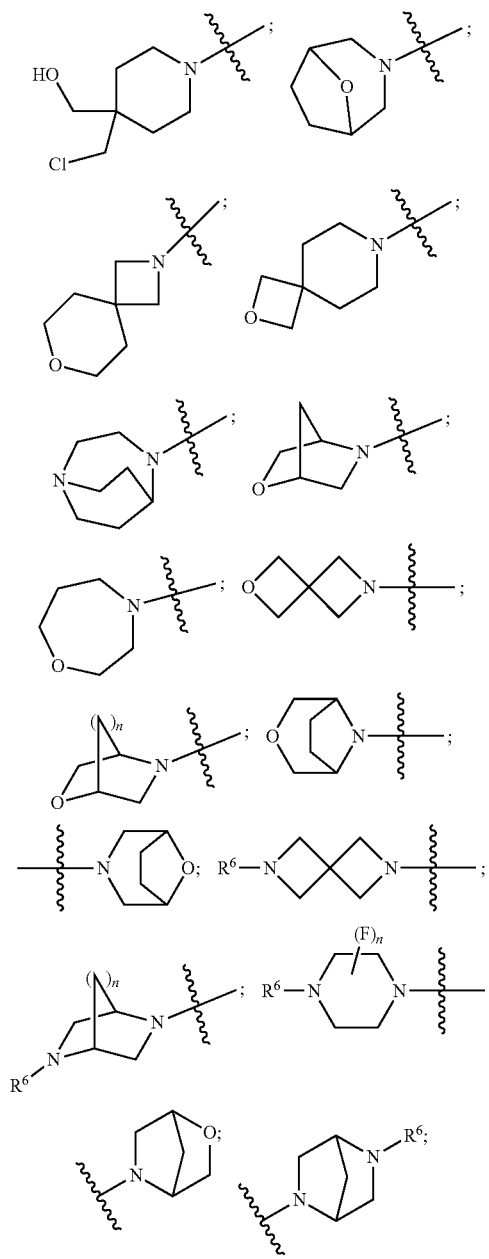

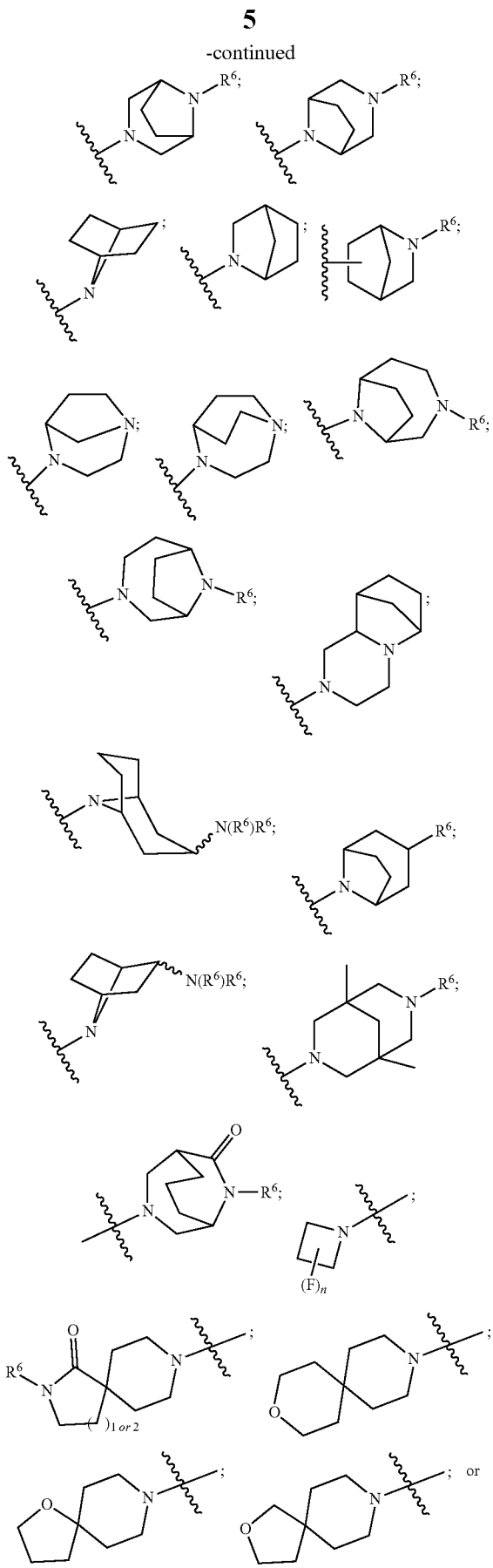

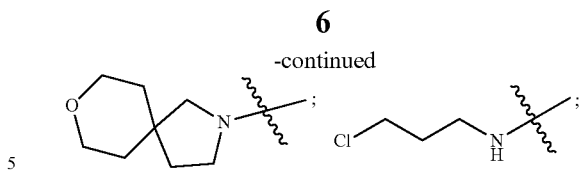

wherein each n independently is an integer ranging from 0 to 4, such as 0, 1, 2, 3, or 4; and $R^6$ independently is selected from hydrogen; aliphatic, such as $C_{1-10}$aliphatic; aromatic, such as $C_{5-10}$aromatic; or heteroaliphatic, such as $C_{1-10}$heteroaliphatic. Exemplary compound embodiments are disclosed herein and can be selected from any one or more of compounds I-1 through I-27.

Also disclosed herein are pharmaceutical composition embodiments comprising a compound (or compounds) according to any of the formulas and/or species disclosed herein (or a pharmaceutically acceptable salt, a stereoisomer, an N-oxide, a tautomer, a hydrate, a solvate, an isotope, or a prodrug thereof), and at least one additional active and/or non-active agent, such as an excipient, a therapeutic agent, an adjuvant, or combinations thereof.

Also disclosed herein are embodiments of a method for using disclosed compounds. One such embodiment comprises contacting a receptor-interacting protein-1 (RIP1) kinase with a compound according to any of the formulas and/or species disclosed herein (or a pharmaceutically acceptable salt, a stereoisomer, an N-oxide, a tautomer, a hydrate, a solvate, an isotope, or a prodrug thereof), or a pharmaceutical composition embodiment described herein. Contacting can occur ex vivo or in vivo.

Also disclosed is a method for treating a disease in a subject, comprising administering to the subject (i) a therapeutically effective amount of the compound according to any of the formulas and/or species disclosed herein (or a pharmaceutically acceptable salt, a stereoisomer, an N-oxide, a tautomer, a hydrate, a solvate, an isotope, or a prodrug thereof); and/or (ii) a therapeutically effective amount of a pharmaceutical composition embodiment described herein; wherein the subject has, or is suspected of having or developing a disease involving a receptor-interacting protein-1 (RIP1) kinase.

The foregoing and other objects, features, and advantages of the present disclosure will become more apparent from the following detailed description.

DETAILED DESCRIPTION

I. Overview of Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references, including patents and patent applications cited herein, are incorporated by reference.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is expressly recited.

Unless explained otherwise, all technical and scientific terms used herein have the same meaning as commonly understood to one of ordinary skill in the art to which this disclosure pertains. Although methods and materials similar or equivalent to those described herein can be used in the practice or testing of the present disclosure, suitable methods and materials are described below. The materials, methods, and examples are illustrative only and not intended to be limiting.

When chemical structures are depicted or described, unless explicitly stated otherwise, all carbons are assumed to include hydrogen so that each carbon conforms to a valence of four. For example, in the structure on the left-hand side of the schematic below there are nine hydrogen atoms implied. The nine hydrogen atoms are depicted in the right-hand structure.

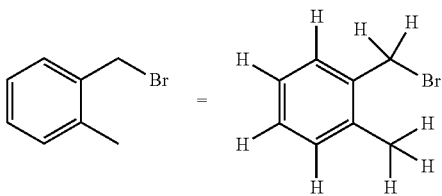

Sometimes a particular atom in a structure is described in textual formula as having a hydrogen or hydrogen atoms, for example —CH$_2$CH$_2$—. It will be understood by a person of ordinary skill in the art that the aforementioned descriptive techniques are common in the chemical arts to provide brevity and simplicity to description of organic structures.

If an R group is depicted as "floating" on a ring system, as for example with R$^1$ in the group:

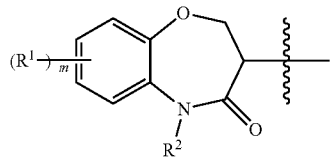

then, unless otherwise defined, a substituent R (e.g., R$^1$ above) can reside on any atom of the fused bicyclic ring system, excluding the atom carrying the bond with the "⁀⁀⁀" symbol, so long as a stable structure is formed.

When a group R is depicted as existing on a ring system containing saturated carbons, as for example in the formula:

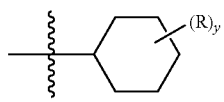

where, in this example, y can be more than one, assuming each replaces a currently depicted, implied, or expressly defined hydrogen on the ring; then, unless otherwise defined, two R's can reside on the same carbon. A simple example is when R is a methyl group. The depicted structure can exist as a geminal dimethyl on a carbon of the depicted ring (an "annular" carbon). In another example, two R's on the same carbon, including that same carbon, can be included in a ring, thus creating a spirocyclic ring (a "spirocyclyl" group) structure. For example, as shown below two Rs can form an oxetane or tetrahydropyran ring in a spirocyclic arrangement with the piperidine or azetidine ring, as

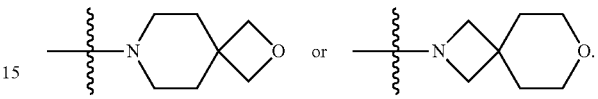

As used herein, the term "substituted" refers to all subsequent modifiers in a term, for example in the term "substituted arylC$_{1-8}$alkyl," substitution may occur on the "C$_{1-8}$alkyl" portion, the "aryl" portion or both portions of the arylC$_{1-8}$alkyl group.

"Substituted," when used to modify a specified group or moiety, means that at least one, and perhaps two or more, hydrogen atoms of the specified group or moiety are independently replaced with the same or different substituent groups as defined below. In a particular embodiment, a group, moiety or substituent may be substituted or unsubstituted, unless expressly defined as either "unsubstituted" or "substituted." Accordingly, any of the groups specified herein may be unsubstituted or substituted unless the context indicates otherwise or a particular structural formula precludes substitution. In particular embodiments, a substituent may or may not be expressly defined as substituted, but is still contemplated to be optionally substituted. For example, an "aliphatic" or a "cyclic" moiety may be unsubstituted or substituted, but an "unsubstituted aliphatic" or an "unsubstituted cyclic" is not substituted.

"Substituents" or "substituent groups" for substituting for one or more hydrogen atoms on saturated carbon atoms in the specified group or moiety can be, unless otherwise specified, —R$^{60}$, halo, =O, —OR$^{70}$, —SR$^{70}$, —N(R$^{80}$)$_2$, haloalkyl, perhaloalkyl, —CN, —NO$_2$, =N$_2$, —N$_3$, —SO$_2$R$^{70}$, —SO$_3$⁻M⁺, —SO$_3$R$^{70}$, —OSO$_2$R$^{70}$, —OSO$_3$⁻M⁺, —OSO$_3$R$^{70}$, —P(O)(O⁻)$_2$(M⁺)$_2$, —P(O)(O⁻)$_2$M$^{2+}$, —P(O)(OR$^{70}$)O⁻M⁺, —P(O)(OR$^{70}$)$_2$, —C(O)R$^{70}$, —C(S)R$^{70}$, —C(NR$^{70}$)R$^{70}$, —CO$_2$⁻M⁺, —CO$_2$R$^{70}$, —C(S)OR$^{70}$, —C(O)N(R$^{80}$)$_2$, —C(NR$^{70}$)(R$^{80}$)$_2$, —OC(O)R$^{70}$, —OC(S)R$^{70}$, —OCO$_2$⁻M⁺, —OCO$_2$R$^{70}$, —OC(S)OR$^{70}$, —NR$^{70}$C(O)R$^{70}$, —NR$^{70}$C(S)R$^{70}$, —NR$^{70}$CO$_2$⁻M⁺, —NR$^{70}$CO$_2$R$^{70}$, —NR$^{70}$C(S)OR$^{70}$, —NR$^{70}$C(O)N(R$^{80}$)$_2$, —NR$^{70}$C(NR$^{70}$)R$^{70}$ and —NR$^{70}$C(NR$^{70}$)N(R$^{80}$)$_2$, where R$^{60}$ is C$_{1-10}$aliphatic, heteroaliphatic, or cycloaliphatic, typically, C$_{1-6}$aliphatic, more typically C$_{1-6}$alkyl, where R$^{60}$ optionally may be substituted; each R$^{70}$ is independently for each occurrence hydrogen or R$^{60}$; each R$^{80}$ is independently for each occurrence R$^{70}$ or alternatively, two R$^{80}$ groups, taken together with the nitrogen atom to which they are bonded, form a 3- to 7-membered heterocycloaliphatic, which optionally includes from 1 to 4 of the same or different additional heteroatoms selected from O, N and S, of which N optionally has R$^{70}$ substitution, such as H or C$_1$-C$_3$alkyl substitution; and each M⁺ is a counter ion with a net single positive charge. Each M⁺ is independently for each occurrence, for example, an alkali metal ion, such as K⁺, Na⁺, Li⁺; an ammonium ion, such as ⁺N(R$^{60}$)$_4$; a protonated amino acid ion, such as a lysine ion, or an arginine ion; or an alkaline metal earth ion, such as $[Ca^{2+}]_{0.5}$, $[Mg^{2+}]_{0.5}$, or $[Ba^{2+}]_{0.5}$ (a subscript "0.5" means, for example, that one of the counter ions for such divalent alkali earth ions can be an ionized form of a compound of the invention and the other a typical counter ion such as chloride, or two ionized compounds can serve as counter ions for such divalent alkali earth ions, or a doubly ionized compound can serve as the counter ion for such divalent alkali earth ions). As specific examples, —N($R^{80}$)$_2$ includes —NH$_2$, —NH-alkyl, —NH-pyrrolidin-3-yl, N-pyrrolidinyl, N-piperazinyl, 4N-methyl-piperazin-1-yl, N-morpholinyl and the like. Any two hydrogen atoms on a single carbon also can be replaced with, for example, =O, =N$R^{70}$, =N—O$R^{70}$, =N$_2$ or =S.

Substituent groups for replacing hydrogen atoms on unsaturated carbon atoms in groups containing unsaturated carbons are, unless otherwise specified, —$R^{60}$, halo, —O$^-$M$^+$, —O$R^{70}$, —S$R^{70}$, —S$^-$M$^+$, —N($R^{80}$)$_2$, perhaloalkyl, —CN, —OCN, —SCN, —NO, —NO$_2$, —N$_3$, —SO$_2R^{70}$, —SO$_3^-$M$^+$, —SO$_3R^{70}$, —OSO$_2R^{70}$, —OSO$_3^-$M$^+$, —OSO$_3R^{70}$, —PO$_3^{-2}$(M$^+$)$_2$, —PO$_3^{-2}$M$^{2+}$, —P(O)(O$R^{70}$)O$^-$M$^+$, —P(O)(O$R^{70}$)$_2$, —C(O)$R^{70}$, —C(S)$R^{70}$, —C(N$R^{70}$)$R^{70}$, —CO$_2^-$M$^+$, —CO$_2R^{70}$, —C(S)O$R^{70}$, —C(O)N$R^{80}R^{80}$, —C(N$R^{70}$)N($R^{80}$)$_2$, —OC(O)$R^{70}$, —OC(S)$R^{70}$, —OCO$_2^-$M$^+$, —OCO$_2R^{70}$, —OC(S)O$R^{70}$, —N$R^{70}$C(O)$R^{70}$, —N$R^{70}$C(S)$R^{70}$, —N$R^{70}$CO$_2^-$M$^+$, —N$R^{70}$CO$_2R^{70}$, —N$R^{70}$C(S)O$R^{70}$, —N$R^{70}$C(O)N($R^{80}$)$_2$, —N$R^{70}$C(N$R^{70}$)$R^{70}$ and —N$R^{70}$C(N$R^{70}$)N($R^{80}$)$_2$, where $R^{60}$, $R^{70}$, $R^{80}$ and M$^+$ are as previously defined. In an independent embodiment, the substituents are not —O$^-$M$^+$, —O$R^{70}$, —S$R^{70}$, or —S$^-$M$^+$.

Substituent groups for replacing hydrogen atoms on nitrogen atoms in groups containing such nitrogen atoms are, unless otherwise specified, —$R^6$, —O$^-$M$^+$, —O$R^{70}$, —S$R^{70}$, —S$^-$M$^+$, —N($R^{80}$)$_2$, perhaloalkyl, —CN, —NO, —NO$_2$, —S(O)$_2R^{70}$, —SO$_3^-$M$^+$, —SO$_3R^{70}$, —OS(O)$_2R^{70}$, —OSO$_3^-$M$^+$, —OSO$_3R^{70}$, —PO$_3^{2-}$(M$^+$)$_2$, —PO$_3^{2-}$M$^{2+}$, —P(O)(O$R^{70}$)O$^-$M$^+$, —P(O)(O$R^{70}$)(O$R^{70}$), —C(O)$R^{70}$, —C(S)$R^{70}$, —C(N$R^{70}$)$R^{70}$, —CO$_2R^{70}$, —C(S)O$R^{70}$, —C(O)N$R^{80}R^{80}$, —C(N$R^{70}$)N$R^{80}R^{80}$, —OC(O)$R^{70}$, —OC(S)$R^{70}$, —OCO$_2R^{70}$, —OC(S)O$R^{70}$, —N$R^{70}$C(O)$R^{70}$, —N$R^{70}$C(S)$R^{70}$, —N$R^{70}$CO$_2R^{70}$, —N$R^{70}$C(S)O$R^{70}$, —N$R^{70}$C(O)N($R^{80}$)$_2$, —N$R^{70}$C(N$R^{70}$)$R^{70}$ and —N$R^{70}$C(N$R^{70}$)N($R^{80}$)$_2$, where $R^{60}$, $R^{70}$, $R^{80}$ and M$^+$ are as previously defined.

In one embodiment, a group that is substituted has at least one substituent up to the number of substituents possible for a particular moiety, such as 1 substituent, 2 substituents, 3 substituents, or 4 substituents.

Additionally, in embodiments where a group or moiety is substituted with a substituted substituent, the nesting of such substituted substituents is limited to three, thereby preventing the formation of polymers. Thus, in a group or moiety comprising a first group that is a substituent on a second group that is itself a substituent on a third group, which is attached to the parent structure, the first (outermost) group can only be substituted with unsubstituted substituents. For example, in a group comprising -(aryl-1)-(aryl-2)-(aryl-3), aryl-3 can only be substituted with substituents that are not themselves substituted.

Any group or moiety defined herein can be connected to any other portion of a disclosed structure, such as a parent or core structure, as would be understood by a person of ordinary skill in the art, such as by considering valence rules, comparison to exemplary species, and/or considering functionality, unless the connectivity of the group or moiety to the other portion of the structure is expressly stated, or is implied by context.

"Acyl" refers to the group —C(O)R, where R is H, aliphatic, heteroaliphatic, or aromatic (including both aryl and heteroaryl). Exemplary acyl moieties include, but are not limited to, —C(O)H, —C(O)alkyl, —C(O)$C_1$-$C_6$alkyl, —C(O)$C_1$-$C_6$haloalkyl, —C(O)cycloalkyl, —C(O)alkenyl, —C(O)cycloalkenyl, —C(O)aryl, —C(O)heteroaryl, or —C(O)heterocyclyl. Specific examples include, —C(O)H, —C(O)Me, —C(O)Et, or —C(O)cyclopropyl.

"Aliphatic" refers to a substantially hydrocarbon-based group or moiety. An aliphatic group or moiety can be acyclic, including alkyl, alkenyl, or alkynyl groups (as well as alkylene, alkenylene, or alkynylene groups), cyclic versions thereof, such as cycloaliphatic groups or moieties including cycloalkyl, cycloalkenyl or cycloalkynyl, and further including straight- and branched-chain arrangements, and all stereo and position isomers as well. Unless expressly stated otherwise, an aliphatic group contains from one to twenty-five carbon atoms ($C_{1-25}$); for example, from one to fifteen ($C_{1-15}$), from one to ten ($C_{1-10}$) from one to six ($C_{1-6}$), or from one to four carbon atoms ($C_{1-4}$) for an acyclic aliphatic group or moiety, or from three to fifteen ($C_{3-15}$) from three to ten ($C_{3-10}$), from three to six ($C_{3-6}$), or from three to four ($C_{3-4}$) carbon atoms for a cycloaliphatic group or moiety. An aliphatic group may be substituted or unsubstituted, unless expressly referred to as an "unsubstituted aliphatic" or a "substituted aliphatic." An aliphatic group can be substituted with one or more substituents (up to two substituents for each methylene carbon in an aliphatic chain, or up to one substituent for each carbon of a —C=C— double bond in an aliphatic chain, or up to one substituent for a carbon of a terminal methine group).

"Lower aliphatic" refers to an aliphatic group containing from one to ten carbon atoms ($C_{1-10}$), such as from one to six ($C_{1-6}$), or from one to four ($C_{1-4}$) carbon atoms; or from three to ten ($C_{3-10}$), such as from three to six ($C_{3-6}$) carbon atoms for a lower cycloaliphatic group.

"Alkoxy" refers to the group —OR, where R is a substituted or unsubstituted alkyl or a substituted or unsubstituted cycloalkyl group. In certain examples R is a $C_{1-6}$ alkyl group or a $C_{3-6}$cycloalkyl group. Methoxy (—OCH$_3$) and ethoxy (—OCH$_2$CH$_3$) are exemplary alkoxy groups. In a substituted alkoxy, R is substituted alkyl or substituted cycloalkyl, examples of which in the presently disclosed compounds include haloalkoxy groups, such as —OCF$_2$H.

"Alkoxyalkyl" refers to the group -alkyl-OR, where R is a substituted or unsubstituted alkyl or a substituted or unsubstituted cycloalkyl group; —CH$_2$CH$_2$—O—CH$_2$CH$_3$ is an exemplary alkoxyalkyl group.

"Alkyl" refers to a saturated aliphatic hydrocarbyl group having from 1 to at least 25 ($C_{1-25}$) carbon atoms, more typically 1 to 10 ($C_{1-10}$) carbon atoms such as 1 to 6 ($C_{1-6}$) carbon atoms. An alkyl moiety may be substituted or unsubstituted. This term includes, by way of example, linear and branched hydrocarbyl groups such as methyl (CH$_3$), ethyl (—CH$_2$CH$_3$), n-propyl (—CH$_2$CH$_2$CH$_3$), isopropyl (—CH(CH$_3$)$_2$), n-butyl (—CH$_2$CH$_2$CH$_2$CH$_3$), isobutyl (—CH$_2$CH$_2$(CH$_3$)$_2$), sec-butyl (—CH(CH$_3$)(CH$_2$CH$_3$), t-butyl (—C(CH$_3$)$_3$), n-pentyl (—CH$_2$CH$_2$CH$_2$CH$_2$CH$_3$), and neopentyl (—CH$_2$C(CH$_3$)$_3$).

"Amino" refers to the group —NH$_2$, —NHR, or —NRR, where each R independently is selected from H, aliphatic, heteroaliphatic, aromatic, including both aryl and heteroaryl, or heterocycloaliphatic, or two R groups together with the nitrogen attached thereto form a heterocyclic ring. Examples of such heterocyclic rings include those wherein two R groups together with the nitrogen to which they are attached form a —(CH$_2$)$_{2-5}$— ring optionally interrupted by one or two heteroatom groups, such as —O— or —N(R$^g$) such as in the groups

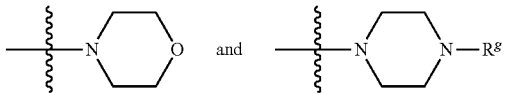

wherein R$^g$ is R$^{70}$, —C(O)R$^{70}$, —C(O)OR$^{60}$ or —C(O)N(R$^{80}$)$_2$.

"Amide" refers to the group —N(R)acyl, wherein R is hydrogen, heteroaliphatic, or aliphatic, such as alkyl, particularly C$_{1-6}$alkyl.

"Aromatic" refers to a cyclic, conjugated group or moiety of, unless specified otherwise, from 5 to 15 ring atoms having a single ring (e.g., phenyl, pyridinyl, or pyrazolyl) or multiple condensed rings in which at least one ring is aromatic (e.g., naphthyl, indolyl, or pyrazolopyridinyl), that is at least one ring, and optionally multiple condensed rings, have a continuous, delocalized π-electron system. Typically, the number of out of plane π-electrons corresponds to the Hückel rule (4n+2). The point of attachment to the parent structure typically is through an aromatic portion of the condensed ring system. For example,

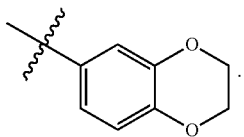 [SMILES: *c1ccc2c(c1)OCCO2]

However, in certain examples, context or express disclosure may indicate that the point of attachment is through a non-aromatic portion of the condensed ring system. For example,

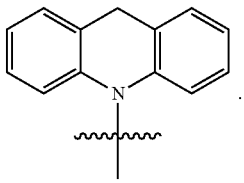 [SMILES: *N1c2ccccc2Cc2ccccc21]

An aromatic group or moiety may comprise only carbon atoms in the ring, such as in an aryl group or moiety, or it may comprise one or more ring carbon atoms and one or more ring heteroatoms comprising a lone pair of electrons (e.g. S, O, N, P, or Si), such as in a heteroaryl group or moiety. Unless otherwise stated, an aromatic group may be substituted or unsubstituted.

"Aryl" refers to an aromatic carbocyclic group of, unless specified otherwise, from 6 to 15 carbon atoms having a single ring (e.g., phenyl) or multiple condensed rings in which at least one ring is aromatic (e.g., 1,2,3,4-tetrahydroquinoline, benzodioxole, and the like). If any aromatic ring portion contains a heteroatom, the group is heteroaryl and not aryl. Aryl groups may be, for example, monocyclic, bicyclic, tricyclic or tetracyclic. Unless otherwise stated, an aryl group may be substituted or unsubstituted.

"Araliphatic" refers to an aryl group attached to the parent via an aliphatic moiety. Araliphatic includes aralkyl or arylalkyl groups such as benzyl and phenylethyl.

"Carboxyl" refers to —CO$_2$H.

"Carboxamide" refers to —C(O)amino.

"Carboxyl ester" or "carboxy ester" refers to the group —C(O)OR, where R is aliphatic, heteroaliphatic, or aromatic (including both aryl and heteroaryl).

"Carboxylate" refers to —C(O)O$^-$ or salts thereof.

"Cyano" refers to the group —CN.

"Cycloaliphatic" refers to a cyclic aliphatic group having a single ring (e.g., cyclohexyl), or multiple rings, such as in a fused, bridged or spirocyclic system, the ring or at least one of the rings in the system is aliphatic. Typically, the point of attachment to the parent structure is through an aliphatic portion of the multiple ring system. Cycloaliphatic includes saturated and unsaturated systems, including cycloalkyl, cycloalkenyl and cycloalkynyl. A cycloaliphatic group may contain from three to twenty-five carbon atoms; for example, from three to fifteen, from three to ten, or from three to six carbon atoms. Unless otherwise stated, a cycloaliphatic group may be substituted or unsubstituted. Exemplary cycloaliphatic groups include, but are not limited to, cyclopropyl, cyclobutyl, cyclopentyl, cyclohexyl, cycloheptyl, cyclopentenyl, or cyclohexenyl.

"Halo," "halide" or "halogen" refers to fluoro, chloro, bromo or iodo.

"Haloalkyl" refers to an alkyl moiety substituted with one or more halogens. Exemplary haloalkyl moieties include —CH$_2$F, —CHF$_2$ and —CF$_3$.

"Heteroaliphatic" refers to an aliphatic compound or group having at least one heteroatom and at least one carbon atom, i.e., at least one carbon atom from an aliphatic compound or group comprising at least two carbon atoms, has been replaced with an atom having at least one lone pair of electrons, typically nitrogen, oxygen, phosphorus, silicon, or sulfur. Heteroaliphatic compounds or groups may be substituted or unsubstituted, branched or unbranched, chiral or achiral, and/or acyclic or cyclic, such as a heterocycloaliphatic group.

"Heteroaryl" refers to an aromatic group or moiety having, unless specified otherwise, from 5 to 15 ring atoms comprising at least one carbon atom and at least one heteroatom, such as N, S, O, P, or Si. A heteroaryl group or moiety may comprise a single ring (e.g., pyridinyl, pyrimidinyl or pyrazolyl) or multiple condensed rings (e.g., indolyl, benzopyrazolyl, or pyrazolopyridinyl). Heteroaryl groups or moiety may be, for example, monocyclic, bicyclic, tricyclic or tetracyclic. Unless otherwise stated, a heteroaryl group or moiety may be substituted or unsubstituted.

"Heterocyclyl," "heterocyclo" and "heterocycle" refer to both aromatic and non-aromatic ring systems, and more specifically refer to a stable three- to fifteen-membered ring moiety comprising at least one carbon atom, and typically plural carbon atoms, and at least one, such as from one to five, heteroatoms. The heteroatom(s) may be nitrogen, phosphorus, oxygen, silicon or sulfur atom(s). The heterocyclyl moiety may be a monocyclic moiety, or may comprise multiple rings, such as in a bicyclic or tricyclic ring system, provided that at least one of the rings contains a heteroatom. Such a multiple ring moiety can include fused or bridged ring systems as well as spirocyclic systems; and any nitrogen, phosphorus, carbon, silicon or sulfur atoms in the heterocyclyl moiety can be optionally oxidized to various oxidation states. For convenience, nitrogens, particularly, but not exclusively, those defined as annular aromatic nitrogens, are meant to include their corresponding N-oxide form, although not explicitly defined as such in a particular example. Thus, for a compound having, for example, a pyridinyl ring, the corresponding pyridinyl-N-oxide is included as another compound of the invention, unless expressly excluded or excluded by context. In addition, annular nitrogen atoms can be optionally quaternized. Heterocycle includes heteroaryl moieties, and heteroalicyclyl or heterocycloaliphatic moieties, which are heterocyclyl rings that are partially or fully saturated. Examples of heterocyclyl groups include, but are not limited to, azetidinyl, oxetanyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, diazabicycloheptane, diazapane, diazepine, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Hydroxyl" refers to the group —OH.

"Nitro" refers to the group —NO$_2$.

"Phosphate" refers to the group —O—P(O)(OR')$_2$, where each —OR' independently is —OH; —O-aliphatic, such as —O-alkyl or —O-cycloalkyl; —O-aromatic, including both —O-aryl and —O-heteroaryl; —O-aralkyl; or —OR' is —O$^-$M$^+$, where M$^+$ is a counter ion with a single positive charge. Each M$^+$ may be an alkali ion, such as K$^+$, Na$^+$, Li$^+$; an ammonium ion, such as $^+$N(R")$_4$ where R" is H, aliphatic, heteroaliphatic, or aromatic (including both aryl and heteroaryl); or an alkaline earth ion, such as [Ca$^{2+}$]$_{0.5}$, [Mg$^{2+}$]$_{0.5}$, or [Ba$^{2+}$]$_{0.5}$. Phosphonooxyalkyl refers to the group -alkyl-phosphate, such as, for example, —CH$_2$OP(O)(OH)$_2$, or a salt thereof, such as —CH$_2$OP(O)(O$^-$Na$^+$)$_2$, and (((dialkoxyphosphoryl)oxy)alkyl) refers to the dialkyl ester of a phosphonooxyalkyl group, such as, for example, —CH$_2$OP(O)(O-tert-butyl)$_2$.

"Phosphonate" refers to the group —P(O)(OR')$_2$, where each —OR' independently is —OH; —O-aliphatic such as —O-alkyl or —O-cycloalkyl; —O-aromatic, including both —O-aryl and —O-heteroaryl; or —O-aralkyl; or —OR' is —O$^-$M$^+$, and M$^+$ is a counter ion with a single positive charge. Each M$^+$ is a positively charged counterion and may be, by way of example, an alkali metal ion, such as K$^+$, Na$^+$, Li$^+$; an ammonium ion, such as $^+$N(R")$_4$ where R" is H, aliphatic, heteroaliphatic, or aromatic (including both aryl and heteroaryl); or an alkaline earth metal ion, such as [Ca$^{2+}$]$_{0.5}$, [Mg$^{2+}$]$_{0.5}$, or [Ba$^{2+}$]$_{0.5}$. Phosphonoalkyl refers to the group -alkyl-phosphonate, such as, for example, —CH$_2$P(O)(OH)$_2$, or —CH$_2$P(O)(O$^-$Na$^+$)$_2$, and ((dialkoxyphosphoryl)alkyl) refers to the dialkyl ester of a phosphonoalkyl group, such as, for example, —CH$_2$P(O)(O-tert-butyl)$_2$.

"Patient" or "Subject" may refer generally to any living being, but more typically refers to mammals and other animals, particularly humans. Thus disclosed methods are applicable to both human therapy and veterinary applications.

"Pharmaceutically acceptable excipient" refers to a substance, other than the active ingredient, that is included in a formulation of the active ingredient. As used herein, an excipient may be incorporated within particles of a pharmaceutical composition, or it may be physically mixed with particles of a pharmaceutical composition. An excipient can be used, for example, to dilute an active agent and/or to modify properties of a pharmaceutical composition. Excipients can include, but are not limited to, antiadherents, binders, coatings, enteric coatings, disintegrants, flavorings, sweeteners, colorants, lubricants, glidants, sorbents, preservatives, carriers or vehicles. Excipients may be starches and modified starches, cellulose and cellulose derivatives, saccharides and their derivatives such as disaccharides, polysaccharides and sugar alcohols, protein, synthetic polymers, crosslinked polymers, antioxidants, amino acids or preservatives. Exemplary excipients include, but are not limited to, magnesium stearate, stearic acid, vegetable stearin, sucrose, lactose, starches, hydroxypropyl cellulose, hydroxypropyl methylcellulose, xylitol, sorbitol, maltitol, gelatin, polyvinylpyrrolidone (PVP), polyethyleneglycol (PEG), tocopheryl polyethylene glycol 1000 succinate (also known as vitamin E TPGS, or TPGS), carboxy methyl cellulose, dipalmitoyl phosphatidyl choline (DPPC), vitamin A, vitamin E, vitamin C, retinyl palmitate, selenium, cysteine, methionine, citric acid, sodium citrate, methyl paraben, propyl paraben, sugar, silica, talc, magnesium carbonate, sodium starch glycolate, tartrazine, aspartame, benzalkonium chloride, sesame oil, propyl gallate, sodium metabisulphite or lanolin.

An "adjuvant" is a component that modifies the effect of other agents, typically the active ingredient. Adjuvants are often pharmacological and/or immunological agents. An adjuvant may modify the effect of an active ingredient by increasing an immune response. An adjuvant may also act as a stabilizing agent for a formulation. Exemplary adjuvants include, but are not limited to, aluminum hydroxide, alum, aluminum phosphate, killed bacteria, squalene, detergents, cytokines, paraffin oil, and combination adjuvants, such as Freund's complete adjuvant or Freund's incomplete adjuvant.

"Pharmaceutically acceptable carrier" refers to an excipient that is a carrier or vehicle, such as a suspension aid, solubilizing aid, or aerosolization aid. *Remington: The Science and Practice of Pharmacy*, The University of the Sciences in Philadelphia, Editor, Lippincott, Williams, & Wilkins, Philadelphia, PA, 21$^{st}$ Edition (2005), incorporated herein by reference, describes exemplary compositions and formulations suitable for pharmaceutical delivery of one or more therapeutic compositions and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

"Pharmaceutically acceptable salt" refers to pharmaceutically acceptable salts of a compound that are derived from a variety of organic and inorganic counter ions as will be known to a person of ordinary skill in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. "Pharmaceutically acceptable acid addition salts" are a subset of "pharmaceutically acceptable salts" that retain the biological effectiveness of the free bases while formed by acid partners. In particular, the disclosed compounds form salts with a variety of pharmaceutically acceptable acids, including, without limitation, inorganic acids such as hydrochloric acid, hydrobromic acid, sulfuric acid, nitric acid, phosphoric acid, and the like, as well as organic acids such as amino acids, formic acid, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, benzene sulfonic acid, isethionic acid, methanesulfonic acid, ethanesulfonic acid, p-toluenesulfonic acid, salicylic acid, xinafoic acid and the like. "Pharmaceutically acceptable base addition salts" are a subset of "pharmaceutically acceptable salts" that are derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, tris(hydroxymethyl)aminomethane (Tris), ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, tris(hydroxymethyl)aminomethane (Tris), ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.) In particular disclosed embodiments, the compounds may be a formate, trifluoroactate, hydrochloride or sodium salt.

"Effective amount" with respect to a compound or pharmaceutical composition refers to an amount of the compound or pharmaceutical composition sufficient to achieve a particular desired result, such as to inhibit a protein or enzyme. In particular embodiments, an "effective amount" is an amount sufficient to inhibit RIP1; to elicit a desired biological or medical response in a tissue, system, subject or patient; to treat a specified disorder or disease; to ameliorate or eradicate one or more of its symptoms; and/or to prevent the occurrence of the disease or disorder. The amount of a compound which constitutes an "effective amount" may vary depending on the compound, the desired result, the disease state and its severity, the size, age, and gender of the patient to be treated and the like, as will be understood by a person of ordinary skill in the art.

"Prodrug" refers to compounds that are transformed in vivo to yield a biologically active compound, or a compound more biologically active than the parent compound. In vivo transformation may occur, for example, by hydrolysis or enzymatic conversion. Common examples of prodrug moieties include, but are not limited to, ester and amide forms of a compound having an active form bearing a carboxylic acid moiety. Examples of pharmaceutically acceptable esters of the compounds of this invention include, but are not limited to, esters of phosphate groups and carboxylic acids, such as aliphatic esters, particularly alkyl esters (for example $C_{1-6}$alkyl esters). Other prodrug moieties include phosphate esters, such as —$CH_2$—O—P(O)(OR')$_2$ or a salt thereof, wherein R' is H or $C_{1-6}$alkyl. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of disclosed exemplary embodiments of compounds according to the present invention can be prepared according to conventional methods. A thorough discussion of prodrugs is provided in T. Higuchi and V. Stella, "Prodrugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Solvate" refers to a complex formed by combination of solvent molecules with molecules or ions of a solute. The solvent can be an organic solvent, an inorganic solvent, or a mixture of both. Exemplary solvents include, but are not limited to, alcohols, such as methanol, ethanol, propanol; amides such as N,N-dialiphatic amides, such as N,N-dimethylformamide; tetrahydrofuran; alkylsulfoxides, such as dimethylsulfoxide; water; and combinations thereof. The compounds described herein can exist in un-solvated as well as solvated forms when combined with solvents, pharmaceutically acceptable or not, such as water, ethanol, and the like. Solvated forms of the presently disclosed compounds are within the scope of the embodiments disclosed herein.

"Sulfonamide" refers to the group or moiety —$SO_2$amino, or —N(R)sulfonyl, where R is H, aliphatic, heteroaliphatic, or aromatic (including both aryl and heteroaryl).

"Sulfanyl" refers to the group or —SH, —S-aliphatic, —S-heteroaliphatic, —S-aromatic, (including both-S-aryl and —S-heteroaryl).

"Sulfinyl" refers to the group or moiety —S(O)H, —S(O) aliphatic, —S(O)heteroaliphatic, or —S(O)aromatic (including both —S(O)aryl and —S(O)heteroaryl).

"Sulfonyl" refers to the group: —$SO_2$H, —$SO_2$aliphatic, —$SO_2$heteroaliphatic, —$SO_2$aromatic (including both —$SO_2$aryl and —$SO_2$heteroaryl).

"Treating" or "treatment" as used herein concerns treatment of a disease or condition of interest in a patient or subject, particularly a human having the disease or condition of interest, and includes by way of example, and without limitation:
  (i) preventing the disease or condition from occurring in a patient or subject, in particular, when such patient or subject is predisposed to the condition but has not yet been diagnosed as having it;
  (ii) inhibiting the disease or condition, for example, arresting or slowing its development;

(iii) relieving the disease or condition, for example, causing diminution of a symptom or regression of the disease or condition or a symptom thereof; or (iv) stabilizing the disease or condition.

As used herein, the terms "disease" and "condition" can be used interchangeably or can be different in that the particular malady or condition may not have a known causative agent (so that etiology has not yet been determined) and it is therefore not yet recognized as a disease but only as an undesirable condition or syndrome, where a more or less specific set of symptoms have been identified by clinicians.

The above definitions and the following general formulas are not intended to include impermissible substitution patterns (e.g., methyl substituted with 5 fluoro groups). Such impermissible substitution patterns are easily recognized by a person having ordinary skill in the art.

A person of ordinary skill in the art will appreciate that compounds may exhibit the phenomena of tautomerism, conformational isomerism, geometric isomerism, and/or optical isomerism. For example, certain disclosed compounds can include one or more chiral centers and/or double bonds and as a consequence can exist as stereoisomers, such as double-bond isomers (i.e., geometric isomers), enantiomers, diasteromers, and mixtures thereof, such as racemic mixtures. As another example, certain disclosed compounds can exist in several tautomeric forms, including the enol form, the keto form, and mixtures thereof. As the various compound names, formulae and compound drawings within the specification and claims can represent only one of the possible tautomeric, conformational isomeric, optical isomeric, or geometric isomeric forms, a person of ordinary skill in the art will appreciate that the disclosed compounds encompass any tautomeric, conformational isomeric, optical isomeric, and/or geometric isomeric forms of the compounds described herein, as well as mixtures of these various different isomeric forms. Mixtures of different isomeric forms, including mixtures of enantiomers and/or stereoisomers, can be separated to provide each separate enantiomers and/or stereoisomer using techniques known to those of ordinary skill in the art, particularly with the benefit of the present disclosure. In cases of limited rotation, e.g. around the amide bond or between two directly attached rings such as pyridinyl rings, biphenyl groups, and the like, atropisomers are also possible and are also specifically included in the compounds of the invention.

In any embodiments, any or all hydrogens present in the compound, or in a particular group or moiety within the compound, may be replaced by a deuterium or a tritium. Thus, a recitation of alkyl includes deuterated alkyl, where from one to the maximum number of hydrogens present may be replaced by deuterium. For example, ethyl refers to both $C_2H_5$ or $C_2H_5$ where from 1 to 5 hydrogens are replaced by deuterium, such as in $C_2D_xH_{5-x}$.

II. RIP1-Active Compounds and Pharmaceutical Compositions Comprising RIP1-Active Compounds A. Compounds Disclosed herein are compounds and pharmaceutical compositions comprising such compounds that are useful for inhibiting RIP1 and/or for treating diseases and/or conditions associated with RIP1. In some embodiments, the compounds are selective kinase inhibitors. For example, exemplary compounds are able to selectively inhibit RIP1 over RIP2, RIP3, or both RIP2 and RIP3. In some embodiments, a compound of the present disclosure can have a structure satisfying Formula I

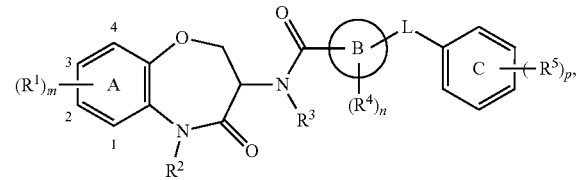

Formula I or a pharmaceutically acceptable salt thereof. A person of ordinary skill in the art will appreciate that the disclosed general formulas include within their scope all stereoisomers, N-oxides, tautomers, hydrates, solvates, isotopes, and/or prodrugs of compounds otherwise having structural features required by such formulas.

With reference to Formula I:
ring B is 5-membered heteroaryl;
L is a $C_{1-10}$aliphatic linker;
$R^1$ is $R^a$ or $R^b$ wherein at least one $R^1$ is $R^b$;
each of $R^2$ and $R^3$ independently are $R^a$;
each $R^4$ and each $R^5$ independently are $R^a$ or $R^b$;
  $R^a$ is independently for each occurrence H or D (except for embodiments where L and/or $R^1$ is $R^a$), $C_{1-10}$aliphatic, or $C_{1-10}$cycloaliphatic;
  $R^b$ is independently for each occurrence halogen or —$NR^dR^d$ wherein (i) each $R^d$ independently is $R^a$ or $R^e$; or (ii) two $R^d$ groups together with the nitrogen bound thereto provide a $C_{3-10}$heterocyclic group, with some embodiments providing a $C_{3-10}$heterocyclic group that is substituted with one or more $R^e$ and/or $R^g$ groups and/or that has one or more additional heteroatoms in addition to the nitrogen to which both $R^d$ groups are bound;
  $R^e$ is independently for each occurrence —$OR^a$, —$NR^a$, $C_{1-6}$alkyl, $C_{1-6}$haloalkyl, $C_{1-6}$heteroalkyl, $C_{3-6}$cycloalkyl, or two $R^e$ groups join together to provide a $C_{3-10}$heterocyclic group with the $R^b$ group to which the two $R^e$ groups are bound, and in some embodiments, the $C_{3-10}$heterocyclic group is substituted with one or more $R^g$ groups;
  $R^g$ is halogen, $C_{1-10}$aliphatic-$C_{5-10}$aromatic, or =O;
  m is 1 to 4, such as 1, 2, 3, or 4, with particular embodiments being 1 or 2;
  n is 0, 1 or 2; and
  p is 0, 1, 2, 3, 4, or 5.

In particular embodiments of Formula I, the 5-membered heteroaryl group can have a structure satisfying formula

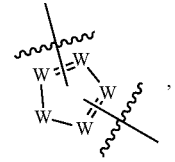

wherein at least one W is nitrogen, and each remaining W independently is selected from carbon, CH, oxygen, sulfur, nitrogen, or NH. In some embodiments, the 5-membered heteroaryl group is a triazole or an oxazole. Exemplary triazoles include any of the following:

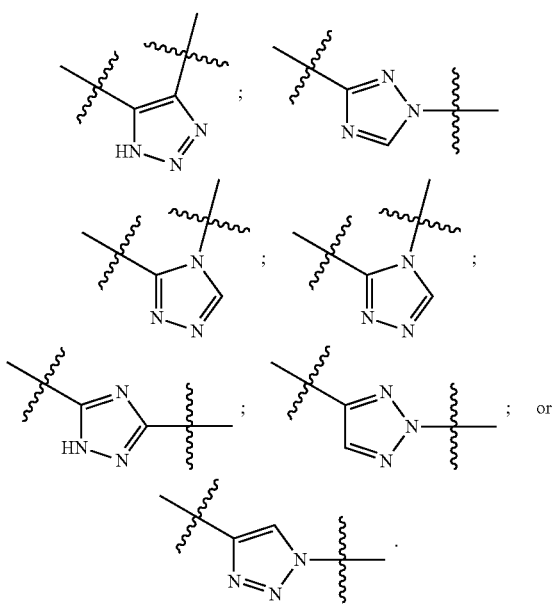

Exemplary oxazoles are include any of the following:

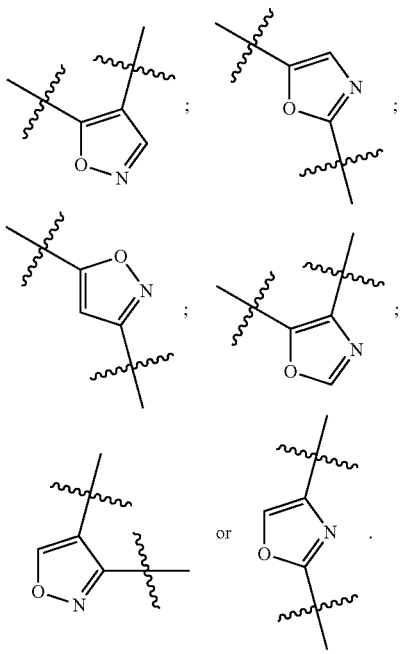

In particular embodiments of Formula I, L is a $C_{1-10}$aliphatic linker, such as a $C_1$-$C_4$alkylene linker (e.g., —$CH_2$—, —$CH_2CH_2$—, —$CH_2CH_2CH_2$—, or —$CH_2CH_2CH_2CH_2$—). In some embodiments, L is —$CH_2$—.

$R^1$ can be positioned on any suitable carbon atom(s) of phenyl ring A, such as at the 1, 2, 3, or 4 position, illustrated in Formula I. In some embodiments, one $R^1$ is $R^a$, wherein $R^a$ is $C_1$-$C_{10}$alkyl (e.g., methyl, ethyl, propyl, butyl, pentyl, hexyl, heptyl, octyl, nonyl, or decyl), and a second $R^1$ is $R^b$, wherein $R^b$ is halogen (e.g., Br, F, I, or Cl) or —$NR^dR^d$ wherein two $R^d$ groups together with the nitrogen bound thereto provide a $C_{4-9}$heterocyclic group. In some embodiments, the $C_{4-9}$heterocyclic group is substituted with one or more $R^e$ groups and/or has one or more additional heteroatoms in addition to the nitrogen to which both $R^d$ groups are bound. Some compound embodiments comprise at least one $R^1$ group that is an R group, wherein $R^b$ is —$NR^dR^d$, wherein (i) each $R^d$ independently is $R^a$ or $R^e$; or (ii) two $R^d$ groups together with the nitrogen bound thereto provide a $C_{4-9}$heterocyclic group. In some embodiments, $R^b$ is —$NR^dR^d$, wherein one $R^d$ is $R^a$, wherein $R^a$ is H, and the other $R^d$ is $R^e$, wherein $R^e$ is $C_{1-6}$haloalkyl. In some embodiments, the heterocyclic group comprises 1 or 2 heteroatoms (including the nitrogen atom of R). Certain heterocyclic groups comprise the nitrogen atom of the $R^b$ group and either an oxygen atom or an additional nitrogen atom. The heterocyclic groups in some compound embodiments are bound to the ring A phenyl ring of Formula I via the nitrogen atom of the $R^b$ group. In some embodiments, the heterocyclic group is substituted with two $R^e$ groups, wherein $R^e$ is independently for each occurrence $C_{1-6}$haloalkyl (e.g., —$CH_2Cl$) or $C_{1-6}$heteroalkyl (e.g., $CH_2OH$). The heterocyclic groups are 6-membered or 7-membered heterocyclic groups. In exemplary embodiments, the heterocyclic group is

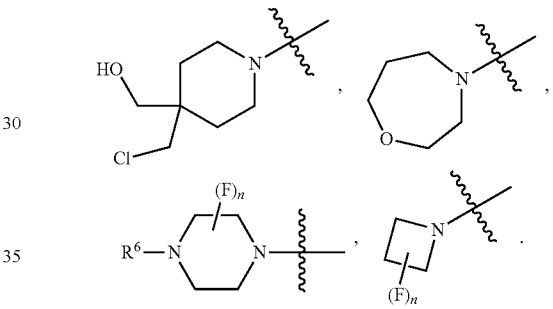

wherein each n independently is an integer ranging from 0 to 4, such as 0, 1, 2, 3, or 4; and $R^6$ is selected from hydrogen; aliphatic, such as $C_{1-10}$aliphatic; aromatic, such as $C_{5-10}$aromatic; or heteroaliphatic, such as $C_{1-10}$heteroaliphatic.

In some embodiments, $R^1$ is $R^b$ wherein $R^b$ is —$NR^dR^d$ and both $R^d$ groups together with the nitrogen bound thereto provide a $C_{4-9}$heterocyclic group substituted with at least two $R^e$ groups wherein the two $R^e$ groups join together to provide a $C_{3-10}$heterocyclic group with the $R^b$ group to which they are attached. In such embodiments, the two $R^e$ groups can join together such that a bicyclic group or a spirocyclic group is provided (wherein one ring of the bicyclic group or spirocyclic group is provided by the $R^b$ group and the other ring of the bicyclic group or the spirocyclic group is provided by the two $R^e$ groups). In embodiments comprising a spirocyclic group, each ring of the spirocyclic group may have the same number of atoms or a different number of atoms. In particular embodiments, the spirocyclic group comprises at least two rings, wherein a first ring and a second ring of the spirocyclic group have a different number of carbon atoms, a different number of heteroatoms, or both. In some embodiments, the two rings of the spirocyclic group comprise the same number of carbon atoms, the same number of heteroatoms, or both. In some embodiments, each ring of the spirocyclic group comprises a heteroatom in the ring and the heteroatom may be the same in each ring, or each ring of the spirocyclic group may have a different heteroatom in the ring. The spirocyclic group can comprise a first ring coupled to a carbon atom of the ring A phenyl group, wherein the first ring has from 3 to 7 atoms, and a second ring has from 3 to 7 atoms. In some embodiments, the spirocyclic group comprises at least one oxygen atom in addition to the nitrogen atom of the $R^b$ group. The spirocyclic group may comprise greater than 7 total atoms in the spirocyclic system with particular embodiments comprising 9 total atoms in the spirocyclic system. In exemplary embodiments, $R^b$ together with two $R^e$ groups can provide the following spirocycles:

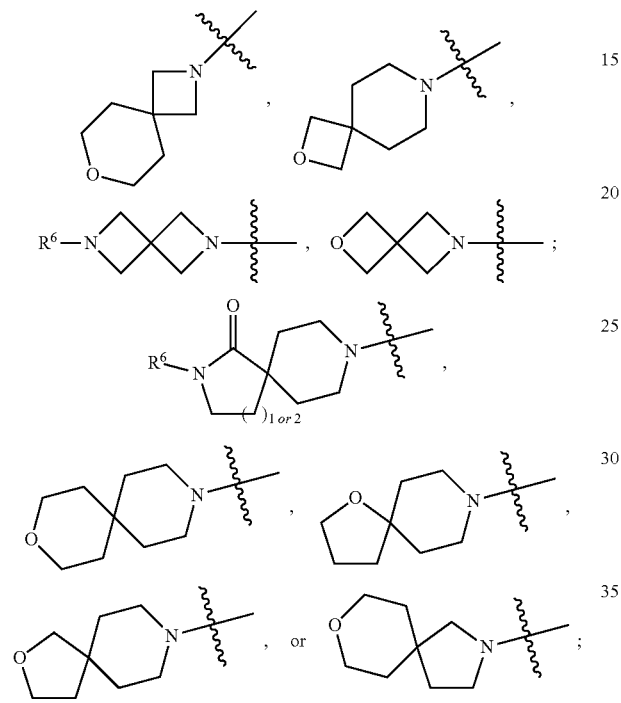

wherein $R^6$ is selected from hydrogen; aliphatic, such as $C_{1-10}$aliphatic; aromatic, such as $C_{5-10}$aromatic; or heteroaliphatic, such as $C_{1-10}$heteroaliphatic.

A bicyclic group may be provided by the $R^b$ group and the two $R^e$ groups attached thereto. The bicyclic may group comprise two or more heteroatoms in the bicyclic group. In such embodiments, the two or more heteroatoms are nitrogen and/or oxygen. In some embodiments, the bicyclic group is attached to a carbon atom of the ring A phenyl group illustrated in the general formulas provided herein through the nitrogen atom of the $R^b$ group when Rb is —$NR^dR^d$. The bicyclic group can be any bicyclic group, including fused bicyclic groups and bridged bicyclic groups, but for certain exemplary embodiments the bicyclic group is a 2.2.1 bicycle, a 3.2.1 bicycle, or a 3.2.2 bicycle. In exemplary embodiments when R together with two $R^e$ groups provide a bicyclic group, the bicycle can be

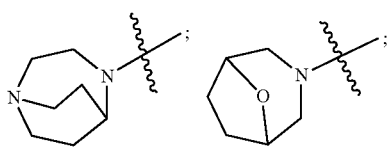

-continued

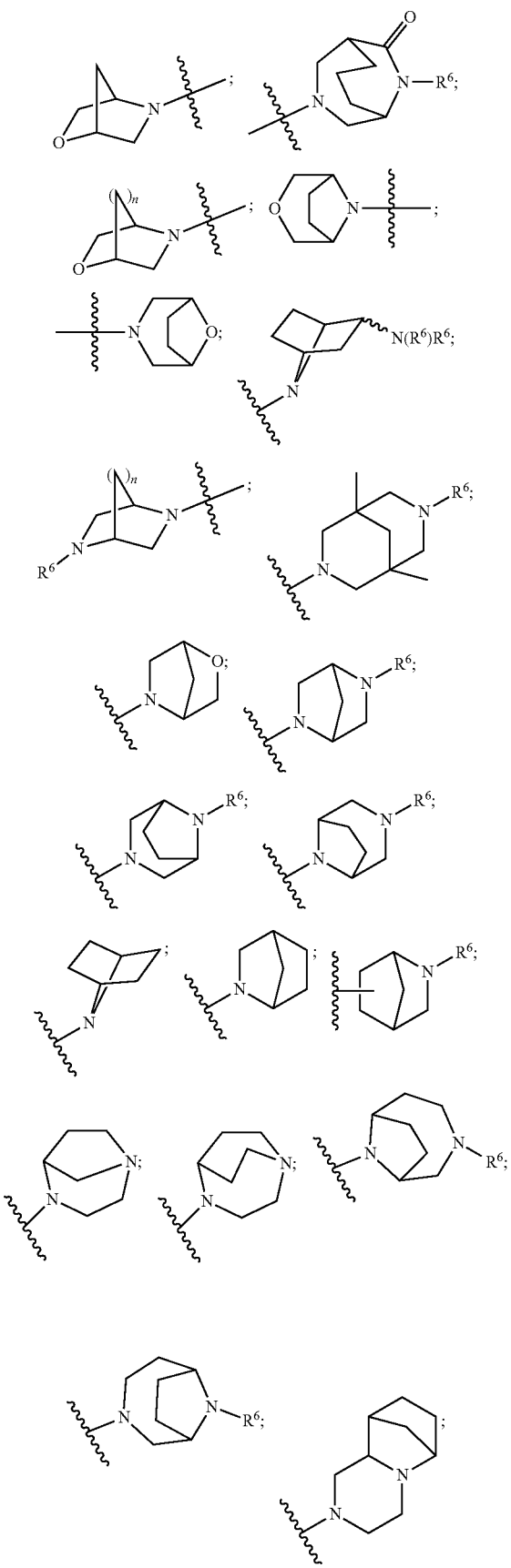

-continued

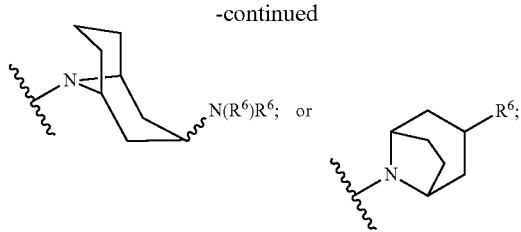

wherein each n independently is an integer ranging from 0 to 4, such as 0, 1, 2, 3, or 4; and $R^6$ independently is selected from hydrogen; aliphatic, such as $C_{1-10}$aliphatic; aromatic, such as $C_{5-10}$aromatic; or heteroaliphatic, such as $C_{1-10}$heteroaliphatic.

In some embodiments, each of $R^2$ and $R^3$ independently is $R^a$, wherein $R^a$ is hydrogen, methyl, ethyl, propyl, butyl, pentyl, or hexyl. In particular embodiments, each of $R^2$ and $R^3$ independently is hydrogen or methyl. In exemplary embodiments, $R^2$ is methyl and $R^3$ is hydrogen.

In some embodiments, each $R^4$ independently and/or each $R^5$ independently is $R^a$ or $R^b$, wherein $R^a$ is independently for each occurrence alkyl, alkenyl, or alkynyl and wherein $R^b$ is chloro, bromo, iodo, or fluoro. In particular embodiments, each $R^4$ and/or each $R^5$ independently is lower alkyl or fluoro.

In some embodiments, m is 1; n is 0 or 1; and p is 0 or 1. In particular embodiments, m is 1, n is 0 and p is 0 or 1.

The compounds of Formula I can also have structures satisfying any one or more of Formulas II and IIA-IIC.

Formula II

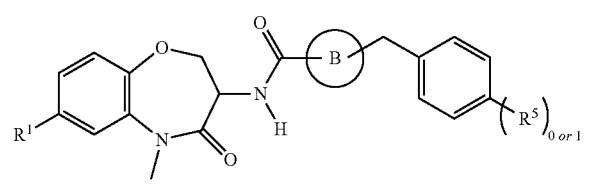

Formula IIA

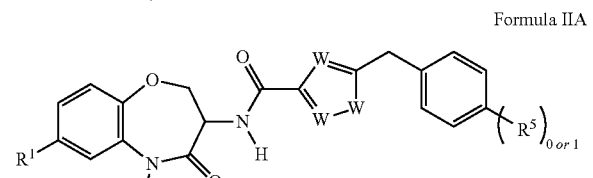

Formula IIB

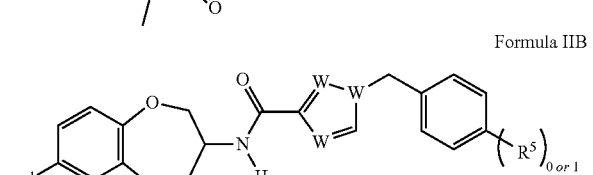

Formula IIC

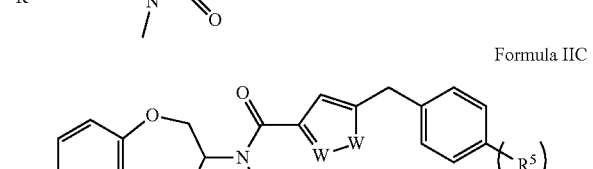

With reference to Formulas II and IIA-IIC, each of $R^1$ and $R^5$ are as recited above for Formula I. In particular embodiments, $R^1$ is $R^b$ wherein $R^b$ is —$NR^dR^d$ and wherein two $R^d$ groups together with the nitrogen bound thereto provide a heterocyclic group substituted with two $R^e$ groups, wherein the $R^e$ groups are independently for each occurrence $C_{1-6}$haloalkyl or $C_{1-6}$heteroalkyl or wherein the two $R^e$ groups join together to provide a $C_{3-10}$heterocyclic group with the $R^b$ group to which the two $R^e$ groups are bound. In some embodiments, and the two $R^e$ groups a bicyclic group or a spirocyclic group. In particular embodiments, $R^5$ is present and is fluoro. In other particular embodiments, $R^5$ is not present. With reference to Formulas IIA-IIC, each W independently is nitrogen or oxygen.

In some embodiments, the compounds of Formula I can also have structures satisfying any one or more of Formula III wherein $R^1$ is a heterocyclic group; Formulas IVA or IVB wherein $R^1$ is a heterocyclic group and further is a spirocyclic group; or Formulas VA, VB, or VC wherein $R^1$ is a heterocyclic group and further is a bicyclic group.

Formula III

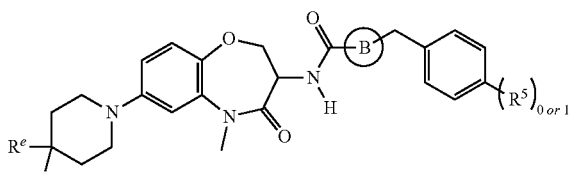

Formula IVA

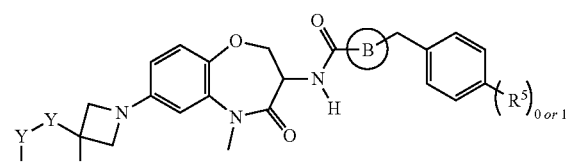

Formula IVB

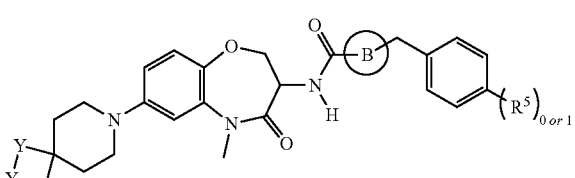

Formula VA

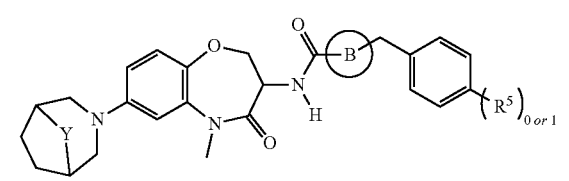

Formula VB

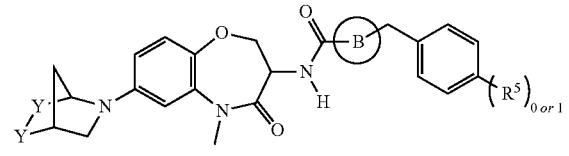

Formula VC

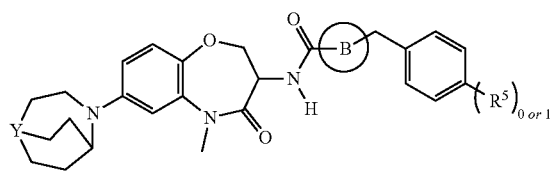

With reference to Formula III, each $R^e$ is independently for each occurrence $C_{1-6}$haloalkyl (e.g., alkyl-Cl, alkyl-Br, alkyl-F, or alkyl-I) or $C_{1-6}$heteroalkyl (e.g., alkyl-OH). In particular embodiments of Formula III, one $R^e$ is —CH$_2$OH and the other $R^e$ is —CH$_2$Cl. With reference to Formulas IVA and IVB, each Y independently is nitrogen, oxygen, or —C(R$^f$)$_2$—, wherein each R$^f$ independently for each occurrence is hydrogen or C$_1$-C$_6$alkyl, such as methyl, ethyl, propyl, butyl, pentyl, or hexyl. In particular embodiments of Formula IVA, IVB, VA and VB, at least one Y is oxygen and the remaining Y variables are all —CH$_2$—. In particular embodiments of Formulas IVA, IVB, VA and VB, at least one Y is oxygen, for example at least one Y is oxygen and the remaining Y variables are all —CH$_2$—. In particular embodiments of Formula VC, Y is nitrogen or —CR$^f$—, wherein R$^f$ is hydrogen or aliphatic, particularly C$_1$-C$_6$alkyl, such as methyl, ethyl, propyl, butyl, pentyl, or hexyl. In particular embodiments of Formula VC, X is nitrogen and Y is nitrogen. With reference to any one of Formulas III, IVA, IVB, and VA-VC, ring B is

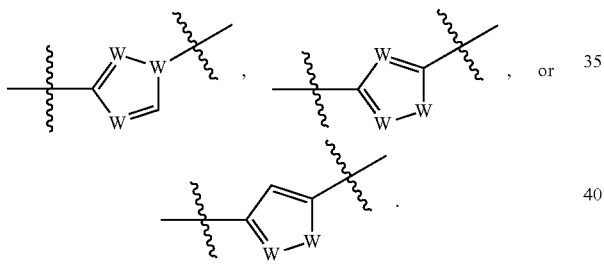

Certain disclosed exemplary compounds within the scope of one or more of Formulas I, II, IIA-IIC, III, IVA, IVB, or VA-VC include:

I-1

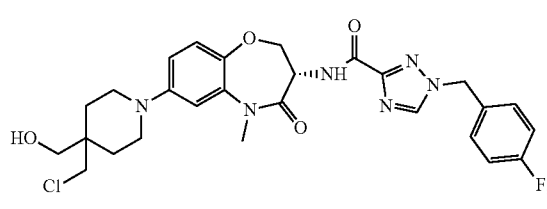

I-2

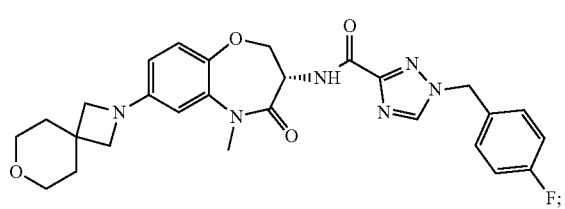

I-3

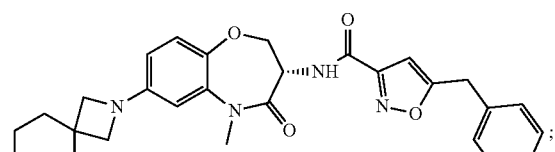

I-4

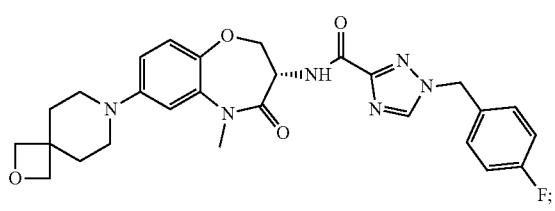

I-5

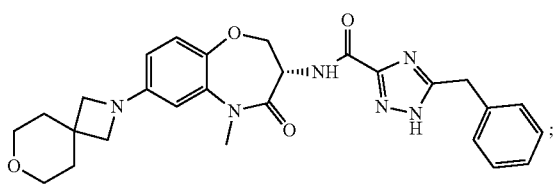

I-6

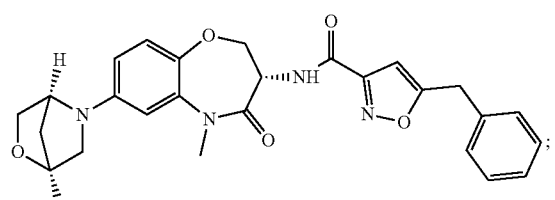

I-7

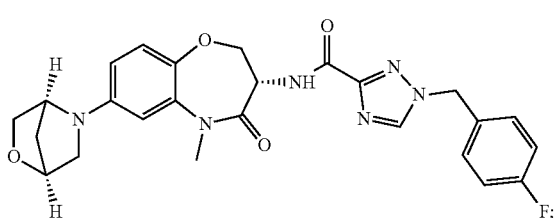

I-8

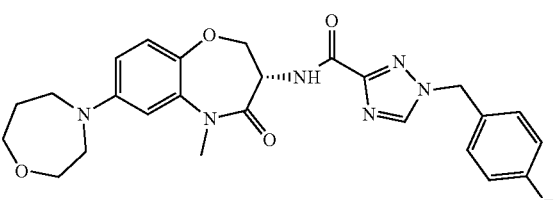

I-9

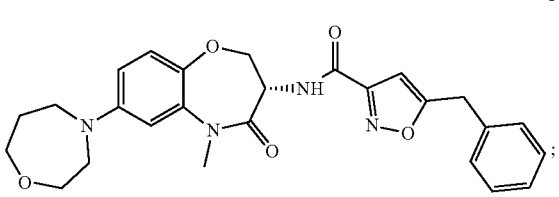

-continued

I-10

I-11

I-12

I-13

I-14

I-15

I-16

-continued

I-17

I-18

I-19

I-20

I-21

I-22

I-23

I-24

-continued

I-25
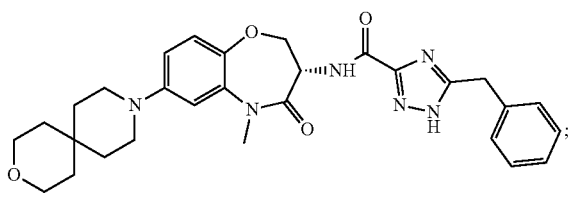

I-26
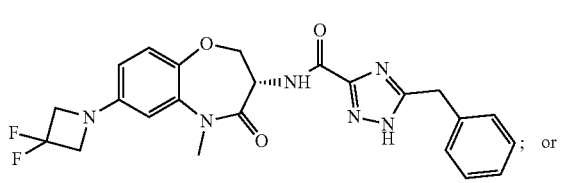
or

I-27
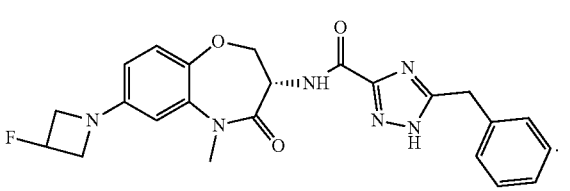

Exemplary compounds within the scope of one or more of Formulas I-V, VIA, VIB, or VIIA-VIIC include:

I-1: (S)—N-(7-(4-(chloromethyl)-4-(hydroxymethyl)piperidin-1-yl)-5-methyl-4-oxo-2,3,4,5-tetrahydrobenzo[b][1,4]oxazepin-3-yl)-1-(4-fluorobenzyl)-1H-1,2,4-triazole-3-carboxamide;

I-2: (S)-1-(4-fluorobenzyl-N-(5-methyl-4-oxo-7-(7-oxa-2-azaspiro[3.5]nonan-2-yl)-2,3,4,5-tetrahydrobenzo[b][1,4]oxazepin-3-yl)-1H-1,2,4-triazole-3-carboxamide;

I-3: (S)-5-benzyl-N-(5-methyl-4-oxo-7-(7-oxa-2-azaspiro[3.5]nonan-2-yl)-2,3,4,5-tetrahydrobenzo[b][1,4]oxazepin-3-yl)isoxazole-3-carboxamide;

I-4: (S)-1-(4-fluorobenzyl)-N-(5-methyl-4-oxo-7-(2-oxa-7-azaspiro[3.5]nonan-7-yl)-2,3,4,5-tetrahydrobenzo[b][1,4]oxazepin-3-yl)-1H-1,2,4-triazole-3-carboxamide;

I-5: (S)-5-benzyl-N-(5-methyl-4-oxo-7-(7-oxa-2-azaspiro[3.5]nonan-2-yl)-2,3,4,5-tetrahydrobenzo[b][1,4]oxazepin-3-yl)-1H-1,2,4-triazole-3-carboxamide;

I-6: N—((S)-7-((1S,4S)-2-oxa-5-azabicyclo[2.2.1]heptan-5-yl)-5-methyl-4-oxo-2,3,4,5-tetrahydrobenzo[b][1,4]oxazepin-3-yl)-5-benzylisoxazole-3-carboxamide;

I-7: N—((S)-7-((1S,4S)-2-oxa-5-azabicyclo[2.2.1]heptan-5-yl)-5-methyl-4-oxo-2,3,4,5-tetrahydrobenzo[b][1,4]oxazepin-3-yl)-1-(4-fluorobenzyl)-1H-1,2,4-triazole-3-carboxamide;

I-8: (S)-1-(4-fluorobenzyl)-N-(5-methyl-7-(1,4-oxazepan-4-yl)-4-oxo-2,3,4,5-tetrahydrobenzo[b][1,4]oxazepin-3-yl)-1H-1,2,4-triazole-3-carboxamide;

I-9: (S)-5-benzyl-N-(5-methyl-7-(1,4-oxazepan-4-yl)-4-oxo-2,3,4,5 tetrahydrobenzo[b][1,4]oxazepin-3-yl)isoxazole-3-carboxamide;

I-10: (S)-5-(4-fluorobenzyl)-N-(5-methyl-7-(1,4-oxazepan-4-yl)-4-oxo-2,3,4,5-tetrahydrobenzo[b][1,4]oxazepin-3-yl)-1H-1,2,4-triazole-3-carboxamide;

I-11: (S)-5-(4-fluorobenzyl)-N-(5-methyl-4-oxo-7-(7-oxa-2-azaspiro[3.5]nonan-2-yl)-2,3,4,5-tetrahydrobenzo[b][1,4]oxazepin-3-yl)-1H-1,2,4-triazole-3-carboxamide;

I-12: (S)-5-benzyl-N-(5-methyl-7-(1,4-oxazepan-4-yl)-4-oxo-2,3,4,5-tetrahydrobenzo[b][1,4]oxazepin-3-yl)-1H-1,2,4-triazole-3-carboxamide;

I-13: N-((3S)-7-(8-oxa-3-azabicyclo[3.2.1]octan-3-yl)-5-methyl-4-oxo-2,3,4,5-tetrahydrobenzo[b][1,4]oxazepin-3-yl)-5-benzylisoxazole-3-carboxamide;

I-14: (S)—N-(7-(1,4-diazabicyclo[3.2.2]nonan-4-yl)-5-methyl-4-oxo-2,3,4,5-tetrahydrobenzo[b][1,4]oxazepin-3-yl)-5-benzylisoxazole-3-carboxamide;

I-15: (S)-5-benzyl-N-(5-methyl-4-oxo-8-(3-oxa-9-azaspiro[5.5]undecan-9-yl)-2,3,4,5-tetrahydrobenzo[b][1,4]oxazepin-3-yl)-1H-1,2,4-triazole-3-carboxamide;

I-16: (S)—N-(7-(1,4-diazabicyclo[3.2.2]nonan-4-yl)-5-methyl-4-oxo-2,3,4,5-tetrahydrobenzo[b][1,4]oxazepin-3-yl)-5-benzyl-1H-1,2,4-triazole-3-carboxamide;

I-17: (S)-5-benzyl-N-(7-((3-chloropropyl)amino)-5-methyl-4-oxo-2,3,4,5-tetrahydrobenzo[b][1,4]oxazepin-3-yl)-1H-1,2,4-triazole-3-carboxamide;

I-18: (S)-5-benzyl-N-(5-methyl-4-oxo-7-(1-oxa-8-azaspiro[4.5]decan-8-yl)-2,3,4,5-tetrahydrobenzo[b][1,4]oxazepin-3-yl)-1H-1,2,4-triazole-3-carboxamide;

I-19: (S)-5-(4-fluorobenzyl)-N-(5-methyl-4-oxo-7-(1-oxa-8-azaspiro[4.5]decan-8-yl)-2,3,4,5-tetrahydrobenzo[b][1,4]oxazepin-3-yl)-1H-1,2,4-triazole-3-carboxamide;

I-20: (S)—N-(7-(azetidin-1-yl)-5-methyl-4-oxo-2,3,4,5-tetrahydrobenzo[b][1,4]oxazepin-3-yl)-5-benzyl-1H-1,2,4-triazole-3-carboxamide;

I-21: (S)-5-benzyl-N-(5-methyl-4-oxo-7-(2-oxa-8-azaspiro[4.5]decan-8-yl)-2,3,4,5-tetrahydrobenzo[b][1,4]oxazepin-3-yl)-1H-1,2,4-triazole-3-carboxamide;

I-22: (S)-5-benzyl-N-(5-methyl-4-oxo-7-(8-oxa-2-azaspiro[4.5]decan-2-yl)-2,3,4,5-tetrahydrobenzo[b][1,4]oxazepin-3-yl)-1H-1,2,4-triazole-3-carboxamide;

I-23: (S)-5-benzyl-N-(7-(2-benzyl-1-oxo-2,8-diazaspiro[4.5]decan-8-yl)-5-methyl-4-oxo-2,3,4,5-tetrahydrobenzo[b][1,4]oxazepin-3-yl)-1H-1,2,4-triazole-3-carboxamide;

I-24: (S)-5-benzyl-N-(7-(2-benzyl-1-oxo-2,9-diazaspiro[5.5]undecan-9-yl)-5-methyl-4-oxo-2,3,4,5-tetrahydrobenzo[b][1,4]oxazepin-3-yl)-1H-1,2,4-triazole-3-carboxamide;

I-25: (S)-5-benzyl-N-(5-methyl-4-oxo-7-(3-oxa-9-azaspiro[5.5]undecan-9-yl)-2,3,4,5-tetrahydrobenzo[b][1,4]oxazepin-3-yl)-1H-1,2,4-triazole-3-carboxamide;

I-26: (S)-5-benzyl-N-(7-(3,3-difluoroazetidin-1-yl)-5-methyl-4-oxo-2,3,4,5-tetrahydrobenzo[b][1,4]oxazepin-3-yl)-1H-1,2,4-triazole-3-carboxamide; and I-27: (S)-5-benzyl-N-(7-(3-fluoroazetidin-1-yl)-5-methyl-4-oxo-2,3,4,5-tetrahydrobenzo[b][1,4]oxazepin-3-yl)-1H-1,2,4-triazole-3-carboxamide.

Additional exemplary compound species contemplated by the present disclosure are illustrated below.

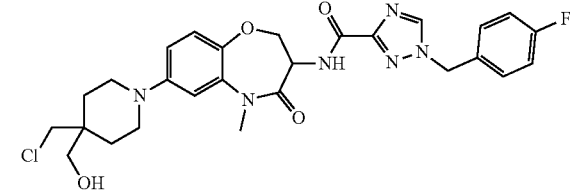

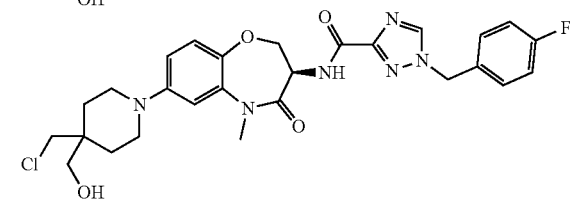

-continued
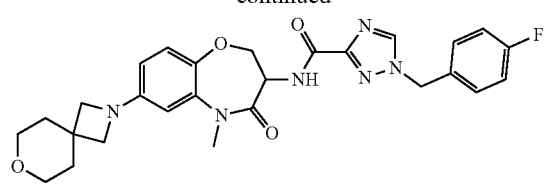
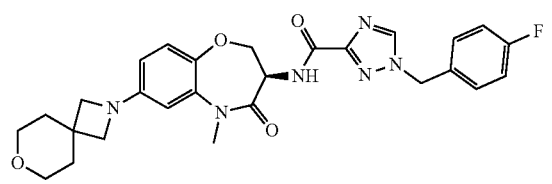
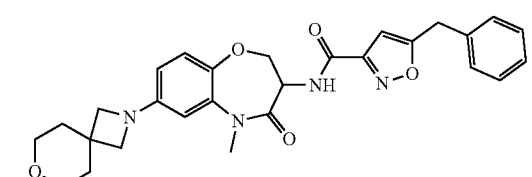
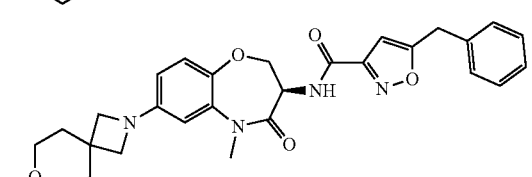
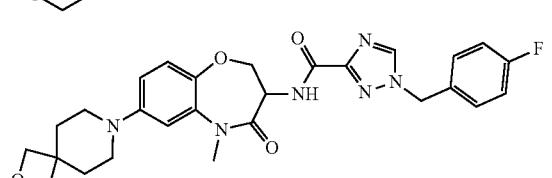
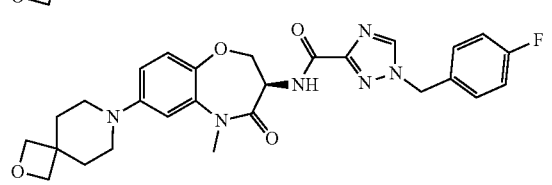
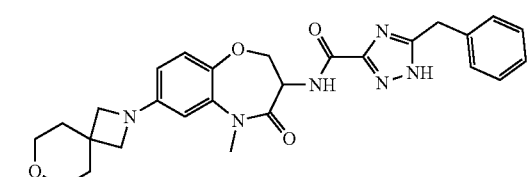
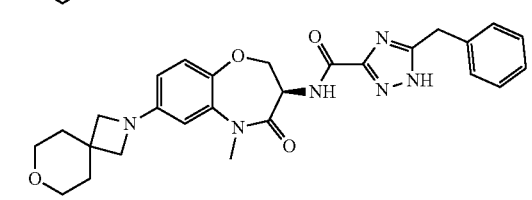
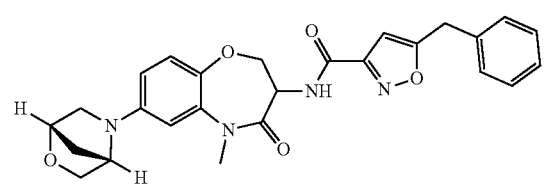
-continued
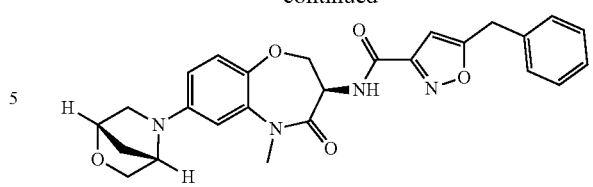
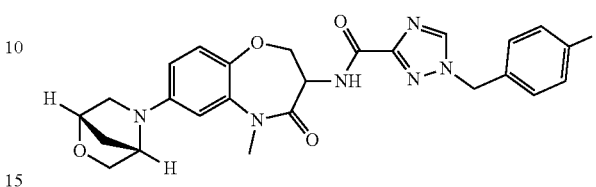
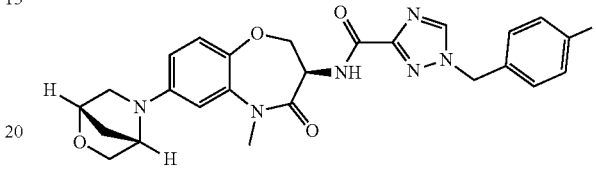
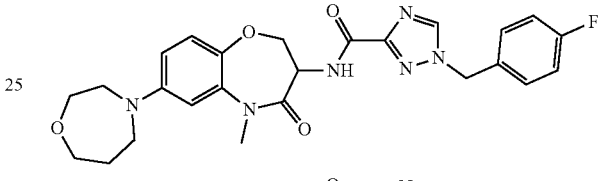
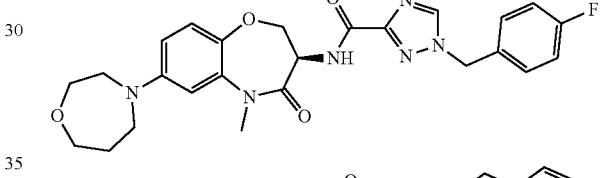
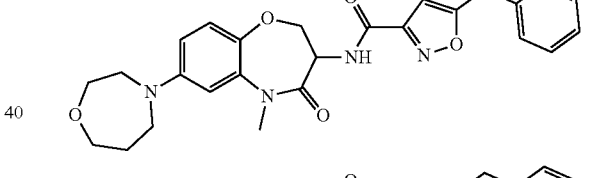
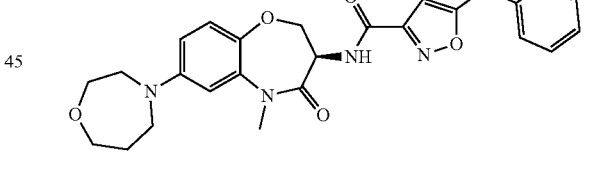
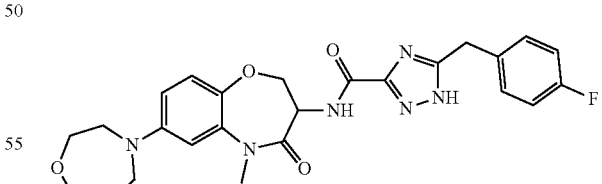
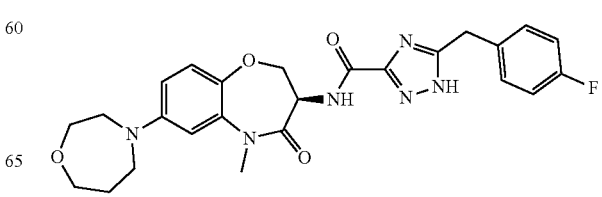

| 33 | 34 |
|---|---|
| -continued | -continued |
| 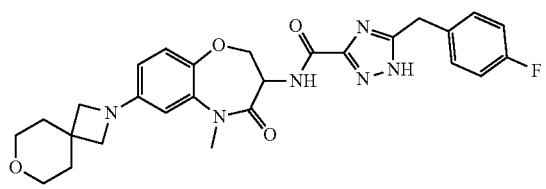 | 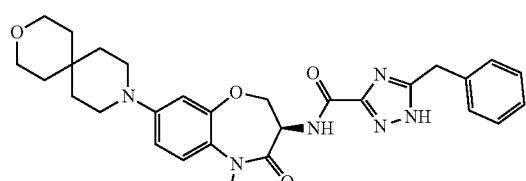 |
| 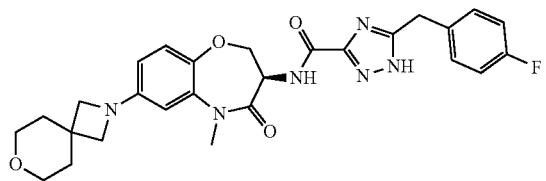 | 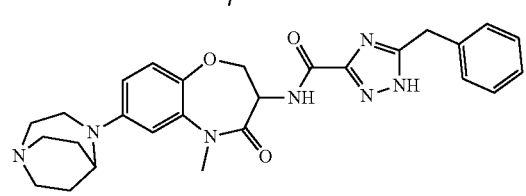 |
| 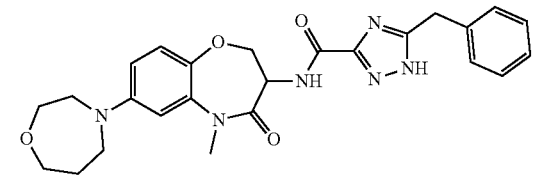 | 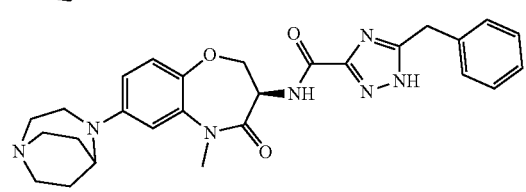 |
| 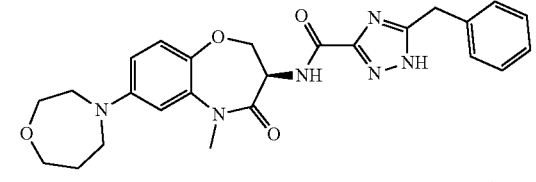 | 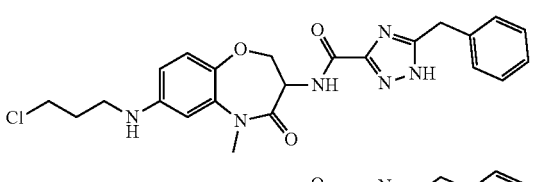 |
| 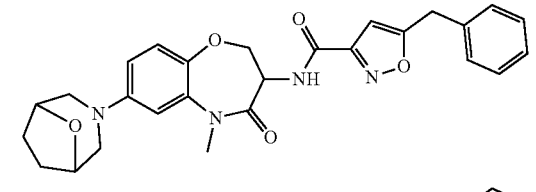 | 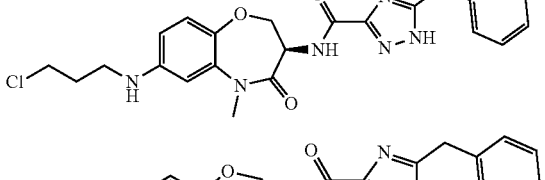 |
| 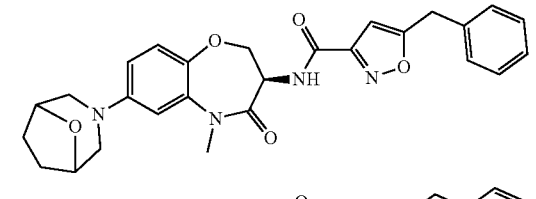 | 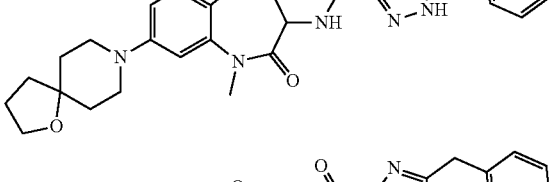 |
| 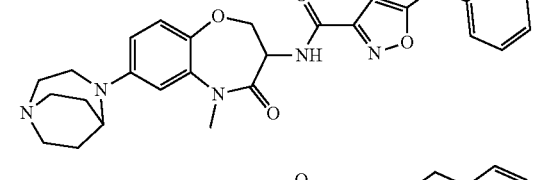 | 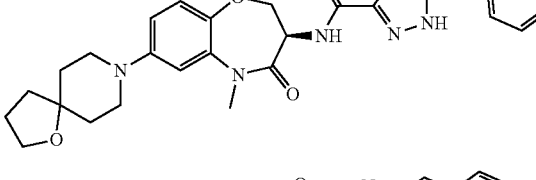 |
| 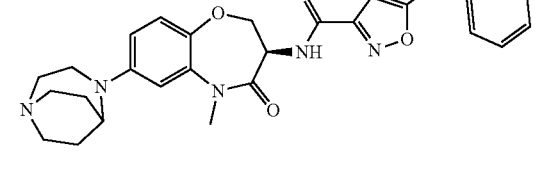 | 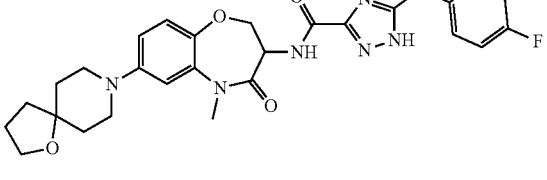 |
| 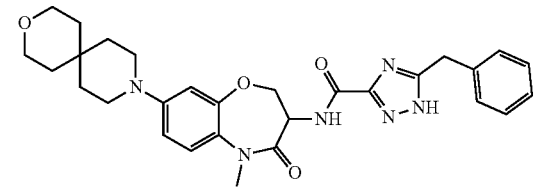 | 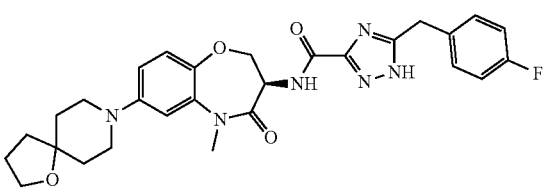 |

-continued
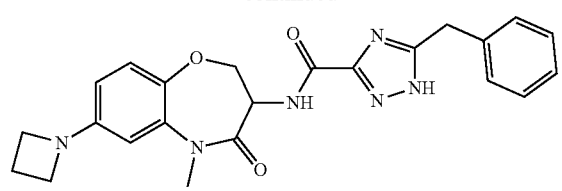
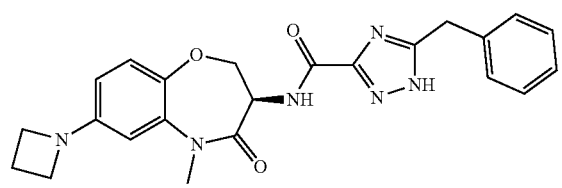
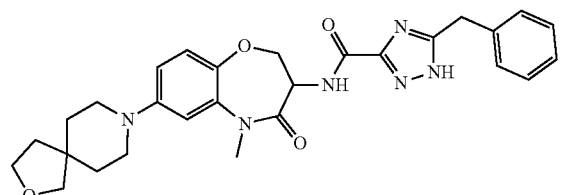
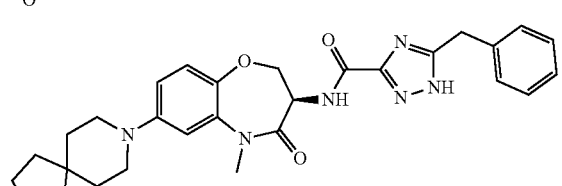
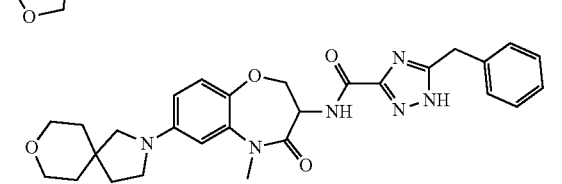
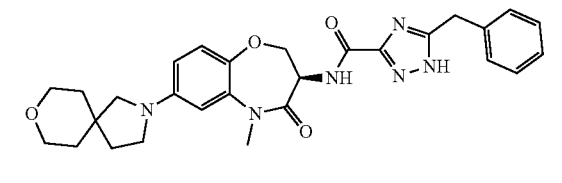
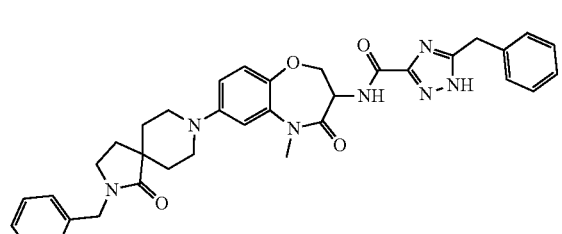
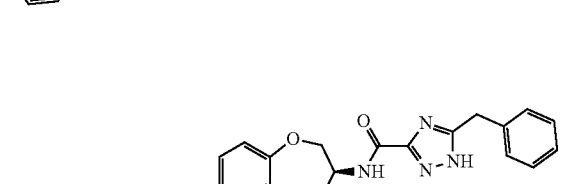
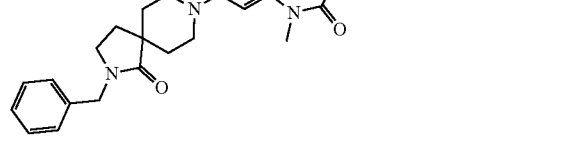
-continued
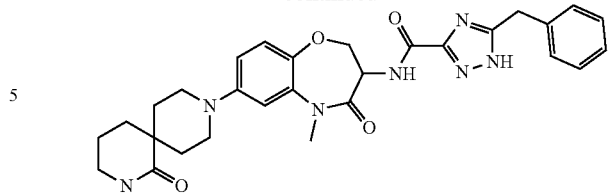
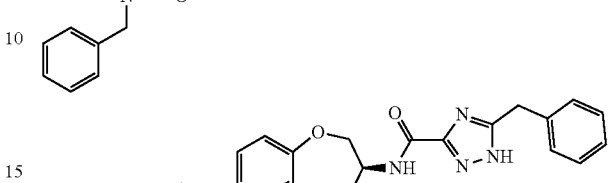
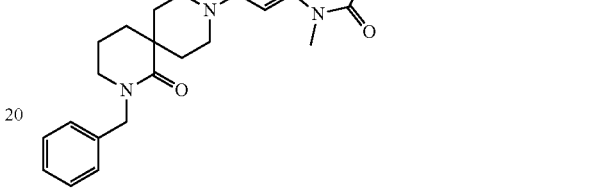
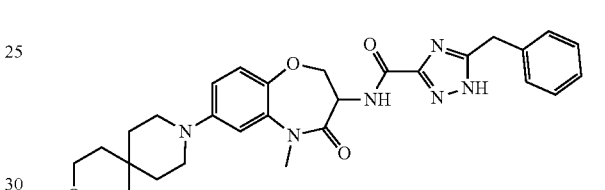
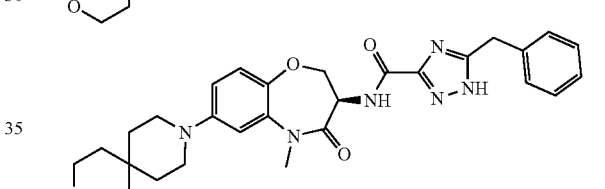
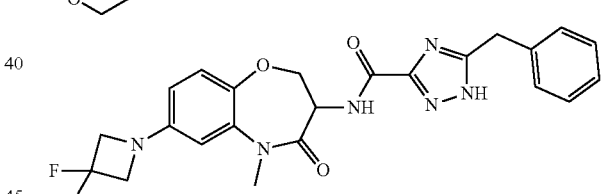
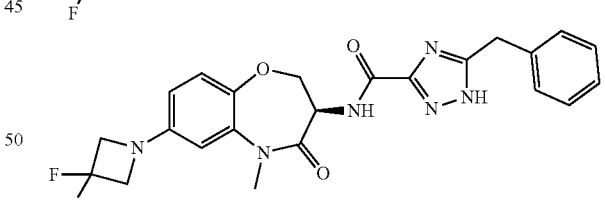
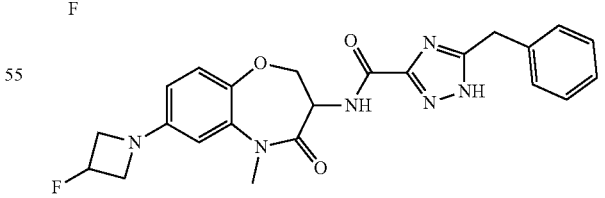
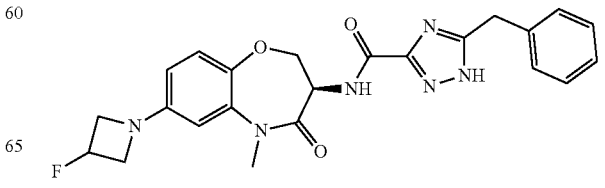

In some embodiments, one or more of the compounds can be included in a pharmaceutical composition or medicament, and in some embodiments the compound or compounds can be in the form of the parent compound or a pharmaceutically acceptable salt, a stereoisomer, an N-oxide, a tautomer, a hydrate, a solvate, an isotope, or a prodrug thereof. The pharmaceutical composition typically includes at least one additional component other than a disclosed compound or compounds, such as a pharmaceutically acceptable excipient, an adjuvant, an additional therapeutic agent (described in the following section), or any combination thereof.

Pharmaceutically acceptable excipients can be included in pharmaceutical compositions for a variety of purposes, such as to dilute a pharmaceutical composition for delivery to a subject, to facilitate processing of the formulation, to provide advantageous material properties to the formulation, to facilitate dispersion from a delivery device, to stabilize the formulation (e.g., antioxidants or buffers), to provide a pleasant or palatable taste or consistency to the formulation, or the like. The pharmaceutically acceptable excipient(s) may include a pharmaceutically acceptable carrier(s). Exemplary excipients include, but are not limited to: mono-, di-, and polysaccharides, sugar alcohols and other polyols, such as, lactose, glucose, raffinose, melezitose, lactitol, maltitol, trehalose, sucrose, mannitol, starch, or combinations thereof; surfactants, such as sorbitols, diphosphatidyl choline, and lecithin; bulking agents; buffers, such as phosphate and citrate buffers; anti-adherents, such as magnesium stearate; binders, such as saccharides (including disaccharides, such as sucrose and lactose,), polysaccharides (such as starches, cellulose, microcrystalline cellulose, cellulose ethers (such as hydroxypropyl cellulose), gelatin, synthetic polymers (such as polyvinylpyrrolidone, polyalkylene glycols); coatings (such as cellulose ethers, including hydroxypropylmethyl cellulose, shellac, corn protein zein, and gelatin); release aids (such as enteric coatings); disintegrants (such as crospovidone, crosslinked sodium carboxymethyl cellulose, and sodium starch glycolate); fillers (such as dibasic calcium phosphate, vegetable fats and oils, lactose, sucrose, glucose, mannitol, sorbitol, calcium carbonate, and magnesium stearate); flavors and sweeteners (such as mint, cherry, anise, peach, apricot or licorice, raspberry, and vanilla; lubricants (such as minerals, exemplified by talc or silica, fats, exemplified by vegetable stearin, magnesium stearate or stearic acid); preservatives (such as antioxidants exemplified by vitamin A, vitamin E, vitamin C, retinyl palmitate, and selenium, amino acids, exemplified by cysteine and methionine, citric acid and sodium citrate, parabens, exemplified by methyl paraben and propyl paraben); colorants; compression aids; emulsifying agents; encapsulation agents; gums; granulation agents; and combinations thereof.

B. Combinations of Therapeutic Agents

The compounds described herein may be used alone, in combination with one another, in separate pharmaceutical compositions, together in a single pharmaceutical composition, or as an adjunct to, or in combination with, other established therapies. The compound or compounds or composition comprising the compound (or compounds) may be administered once, or in plural administrations. In some embodiments, the compounds of the present invention may be used in combination with other therapeutic agents useful for the disorder or condition being treated. These other therapeutic agents may be administered simultaneously, sequentially in any order, by the same route of administration, or by a different route as the presently disclosed compounds. For sequential administration, the compound(s) and the therapeutic agent(s) may be administered such that an effective time period of at least one compound and the therapeutic agent overlaps with an effective time period of at least one other compound and/or therapeutic agent. In an exemplary embodiment of a combination comprising four components, the effective time period of the first component administered may overlap with the effective time periods of the second, third and fourth components, but the effective time periods of the second, third and fourth components independently may or may not overlap with one another. In another exemplary embodiment of a combination comprising four components, the effective time period of the first component administered overlaps with the effective time period of the second component, but not that of the third or fourth; the effective time period of the second component overlaps with those of the first and third components; and the effective time period of the fourth component overlaps with that of the third component only. In some embodiments, the effective time periods of all compounds and/or therapeutic agents overlap with each other.

In some embodiments, the compounds are administered with another therapeutic agent, such as an analgesic, an antibiotic, an anticoagulant, an antibody, an anti-inflammatory agent, an immunosuppressant, a guanylate cyclase-C agonist, an intestinal secretagogue, an antiviral, anticancer, antifungal, or a combination thereof. The anti-inflammatory agent may be a steroid or a nonsteroidal anti-inflammatory agent. In certain embodiments, the nonsteroidal anti-inflammatory agent is selected from aminosalicylates, cyclooxygenase inhibitors, diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, tolmetin, or a combination thereof. In some embodiments, the immunosuppressant is mercaptopurine, a corticosteroid, an alkylating agent, a calcineurin inhibitor, an inosine monophosphate dehydrogenase inhibitor, antilymphocyte globulin, antithymocyte globulin, an anti-T-cell antibody, or a combination thereof. In one embodiment, the antibody is infliximab.

In some embodiments, the present compounds may be used with anti-cancer or cytotoxic agents. Various classes of anti-cancer and anti-neoplastic compounds include, but are not limited to, alkylating agents, antimetabolites, BCL-2 inhibitors, vinca alkyloids, taxanes, antibiotics, enzymes, cytokines, platinum coordination complexes, proteasome inhibitors, substituted ureas, kinase inhibitors, hormones and hormone antagonists, and hypomethylating agents, for example DNMT inhibitors, such as azacitidine and decitabine. Exemplary alkylating agents include, without limitation, mechlorothamine, cyclophosphamide, ifosfamide, melphalan, chlorambucil, ethyleneimines, methylmelamines, alkyl sulfonates (e.g., busulfan), and carmustine. Exemplary antimetabolites include, by way of example and not limitation, folic acid analog methotrexate; pyrmidine analog fluorouracil, cytosine arbinoside; purine analogs mercaptopurine, thioguanine, and azathioprine. Exemplary vinca alkyloids include, by way of example and not limitation, vinblastine, vincristine, paclitaxel, and colchicine. Exemplary antibiotics include, by way of example and not limitation, actinomycin D, daunorubicin, and bleomycin. An exemplary enzyme effective as an anti-neoplastic agent includes L-asparaginase. Exemplary coordination compounds include, by way of example and not limitation, cisplatin and carboplatin. Exemplary hormones and hormone related compounds include, by way of example and not limitation, adrenocorticosteroids prednisone and dexamethasone; aromatase inhibitors amino glutethimide, formestane, and anastrozole; progestin compounds hydroxyprogesterone caproate, medroxyprogesterone; and anti-estrogen compound tamoxifen.

These and other useful anti-cancer compounds are described in Merck Index, 13th Ed. (O'Neil M. J. et al., ed.) Merck Publishing Group (2001) and Goodman and Gilman's The Pharmacological Basis of Therapeutics, 12th Edition, Brunton L. L. ed., Chapters 60-63, McGraw Hill (2011), both of which are incorporated by reference herein.

Among the CTLA 4 antibodies that can be used in combination with the presently disclosed inhibitors is ipilimumab, marketed as YERVOY® by Bristol-Myers Squibb.

Other chemotherapeutic agents for combination include immunooncology agents, such as checkpoint pathway inhibitors, for example, PD-1 inhibitors, such as nivolumab and lambrolizumab, and PD-L1 inhibitors, such as pembrolizumab, MEDI-4736 and MPDL3280A/RG7446. Additional checkpoint inhibitors for combination with the compounds disclosed herein include, Anti-LAG-3 agents, such as BMS-986016 (MDX-1408).

Further chemotherapeutic agents for combination with the presently disclosed inhibitors include Anti-SLAMF7 agents, such as the humanized monoclonal antibody elotuzumab (BMS-901608), anti-KIR agents, such as the anti-KIR monoclonal antibody lirilumab (BMS-986015), and anti-CD137 agents, such as the fully human monoclonal antibody urelumab (BMS-663513).

The presently disclosed compounds also may be used advantageously with CAR-T therapies. Example of currently available CAR-T therapies are axicabtagene ciloleucel and tisagenlecleucel.

Additional anti-proliferative compounds useful in combination with the compounds of the present invention include, by way of example and not limitation, antibodies directed against growth factor receptors (e.g., anti-Her2); and cytokines such as interferon-α and interferon-γ, interleukin-2, and GM-CSF.

Additional chemotherapeutic agents useful in combination with the present compounds include proteasome inhibitors, such as bortezomib, carfilzomib, marizomib and the like.

Examples of kinase inhibitors that are useful in combination with the presently disclosed compounds, particularly in treating malignancies include: Btk inhibitors, such as ibrutinib; CDK inhibitors, such as palbociclib; EGFR inhibitors, such as afatinib, erlotinib, gefitinib, lapatinib, osimertinib and vandetinib; Mek inhibitors, such as trametinib; Raf inhibitors, such as dabrafenib, sorafenib and vemurafenib; VEGFR inhibitors, such as axitinib, lenvatinib, nintedanib, pazopanib; BCR-Abl inhibitors, such as bosutinib, dasatinib, imatinib and nilotinib; FLT-3 inhibitors, such as gilteritinib and quizartinib, PI3-kinase inhibitors, such as idelalisib, Syk inhibitors, such as fostamatinib; and JAK inhibitors, such as ruxolitinib and fedratinib.

In other embodiments, the second therapeutic agent may be selected from any of the following:

analgesics-morphine, fentanyl, hydromorphone, oxycodone, codeine, acetaminophen, hydrocodone, buprenorphine, tramadol, venlafaxine, flupirtine, meperidine, pentazocine, dextromoramide, dipipanone;

antibiotics-aminoglycosides (e.g., amikacin, gentamicin, kanamycin, neomycin, netilmicin, tobramycin, and paromycin), carbapenems (e.g., ertapenem, doripenem, imipenem, cilastatin, and meropenem), cephalosporins (e.g., cefadroxil, cefazolin, cefalotin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, and cefobiprole), glycopeptides (e.g., teicoplanin, vancomycin, and telavancin), lincosamides (e.g., clindamycin and incomysin), lipopeptides (e.g., daptomycin), macrolides (azithromycin, clarithromycin, dirithromycin, erythromycin, roxithromycin, troleandomycin, telithromycin, and spectinomycin), monobactams (e.g., aztreonam), nitrofurans (e.g., furazolidone and nitrofurantoin), penicillins (e.g., amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, and ticarcillin), penicillin combinations (e.g., amoxicillin/clavulanate, ampicillin/sulbactam, piperacillin/tazobactam, and ticarcillin/clavulanate), polypeptides (e.g., bacitracin, colistin, and polymyxin B), quinolones (e.g., ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, and temafloxacin), sulfonamides (e.g., mafenide, sulfonamidochrysoidine, sulfacetamide, sulfadiazine, silver sulfadiazine, sulfamethizole, sulfamethoxazole, sulfanilimide, sulfasalazine, sulfisoxazole, trimethoprim, and trimethoprim-sulfamethoxaxzole), tetracyclines (e.g., demeclocycline, doxycycline, minocycline, oxytetracycline, and tetracycline), antimycobacterial compounds (e.g., clofazimine, dapsone, capreomycin, cycloserine, ethambutol, ethionamide, isoniazid, pyrazinamide, rifampicin (rifampin), rifabutin, rifapentine, and streptomycin), and others, such as arsphenamine, chloramphenicol, fosfomycin, fusidic acid, linezolid, metronidazole, mupirocin, platensimycin, quinuprisin/dalfopristin, rifaximin, thiamphenicol, tigecycline, and timidazole;

antibodies-anti-TNF-α antibodies, e.g., infliximab (Remicade™), adalimumab, golimumab, certolizumab; anti-B cell antibodies, e.g., rituximab; anti-IL-6 antibodies, e.g., tocilizumab; anti-IL-1 antibodies, e.g., anakinra; anti PD-1 and/or anti-PD-L1 antibodies, e.g. nivolumab, pembrolizumab, pidilizumab, BMS-936559, MPDL3280A, AMP-224, MEDI4736; ixekizumab, brodalumab, ofatumumab, sirukumab, clenoliximab, clazakiumab, fezakinumab, fletikumab, mavrilimumab, ocrelizumab, sarilumab, secukinumab, toralizumab, zanolimumab;

anticoagulants-warfarin (Coumadin™), acenocoumarol, phenprocoumon, atromentin, phenindione, heparin, fondaparinux, idraparinux, rivaroxaban, apixaban, hirudin, lepirudin, bivalirudin, argatrobam, dabigatran, ximelagatran, batroxobin, hementin;

anti-inflammatory agents-steroids, e.g., budesonide, non-steroidal anti-inflammatory agents, e.g., aminosalicylates (e.g., sulfasalazine, mesalamine, olsalazine, and balsalazide), cyclooxygenase inhibitors (COX-2 inhibitors, such as rofecoxib, celecoxib), diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, tolmetin;

immunosuppressants-mercaptopurine, corticosteroids such as dexamethasone, hydrocortisone, prednisone, methylprednisolone and prednisolone, alkylating agents such as cyclophosphamide, calcineurin inhibitors such as cyclosporine, sirolimus and tacrolimus, inhibitors of inosine monophosphate dehydrogenase (IMPDH) such as mycophenolate, mycophenolate mofetil and azathioprine, and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. Azathioprine is currently available from Salix Pharmaceuticals, Inc. under the brand name Azasan; mercaptopurine is currently available from Gate Pharmaceuticals, Inc. under the brand name Purinethol; prednisone and prednisolone are currently available from Roxane Laboratories, Inc.; Methyl prednisolone is currently available from Pfizer; sirolimus (rapamycin) is currently available from Wyeth-Ayerst under the brand name Rapamune; tacrolimus is currently available from Fujisawa under the brand name Prograf; cyclosporine is current available from Novartis under the brand name Sandimmune and Abbott under the brand name Gengraf; IMPDH inhibitors such as mycophenolate mofetil and mycophenolic acid are currently available from Roche under the brand name Cellcept and Novartis under the brand name Myfortic; azathioprine is currently available from Glaxo Smith Kline under the brand name Imuran; and antibodies are currently available from Ortho Biotech under the brand name Orthoclone, Novartis under the brand name Simulect (basiliximab) and Roche under the brand name Zenapax (daclizumab); and Guanylate cyclase-C receptor agonists or intestinal secretagogues, for example linaclotide, sold under the name Linzess.

These various agents can be used in accordance with their standard or common dosages, as specified in the prescribing information accompanying commercially available forms of the drugs (see also, the prescribing information in the 2006 Edition of The Physician's Desk Reference), the disclosures of which are incorporated herein by reference.

III. Methods of Making Compounds

Disclosed compounds can be prepared by any acceptable synthetic method as will be understood by a person of ordinary skill in the art with the benefit of the present disclosure. One suitable method is exemplified below, as illustrated for specific compounds in the examples. An exemplary method of making the compounds can include the following first reaction step according to Scheme 1.

Scheme 1

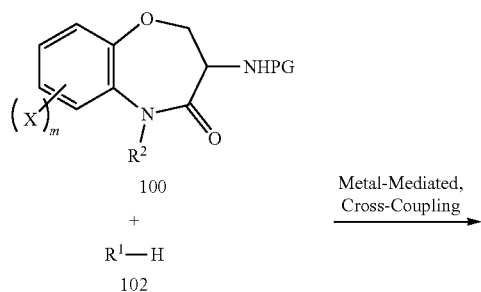

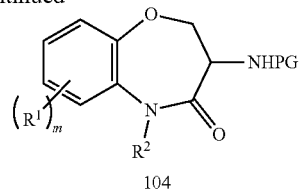
104

With reference to Scheme 1, starting compound 100 is reacted with an $R^1$-containing reagent 102 using suitable metal-mediated, cross-coupling conditions to provide $R^1$-functionalized product 104. X is a suitable group for metal-mediated cross-coupling, such as a halogen or a triflate group and PG is an amine protecting group, which can be selected from, but is not limited to, a 9-fluorenylmethoxycarbonyl ("Fmoc") group, a t-butyloxycarbonyl ("Boc") group, a trityl ("Tr") group, an allyloxycarbonyl ("Alloc") group, a benzyloxycarbonyl ("Cbz") group, and the like. In some embodiments, the metal-mediated, cross-coupling conditions comprise using a transition metal catalyst, such as a Pd(0) catalyst (e.g., $Pd_2(dba)_3$, $Pd(dba)_2$, $Pd(PPh_3)_4$, and the like) in combination with a ligand component, such as a ligand capable of generating Pd(II) from the Pd(0) catalyst (e.g., a BINAP ligand, a BINOL ligand, and the like), a base (e.g., t-BuONa), and a solvent. In some embodiments, the cross-coupling step involves heating the reaction mixture at a suitable temperature (e.g., 60° C. or higher, such as 70° C. to 140° C., or 80° C. to 120° C., or 85° C. to 100° C.).

Representative examples of the method shown in Scheme 1 are provided below in Schemes 2A-2G.

Scheme 2A

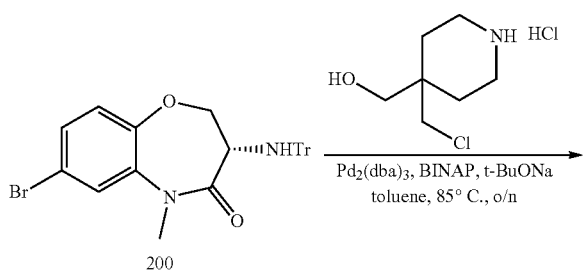
200

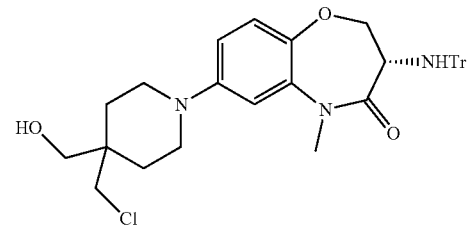
202

Scheme 2B

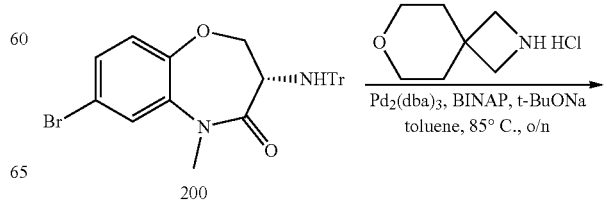
200

-continued

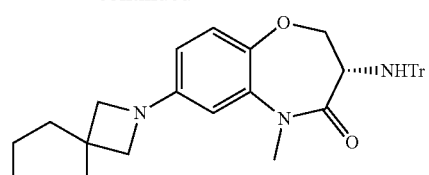
204

Scheme 2B

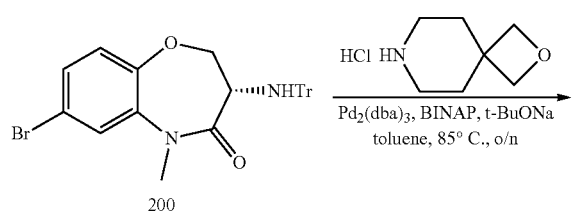
200

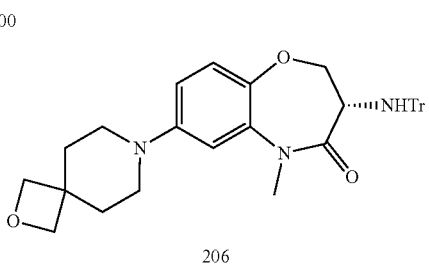
206

Scheme 2D

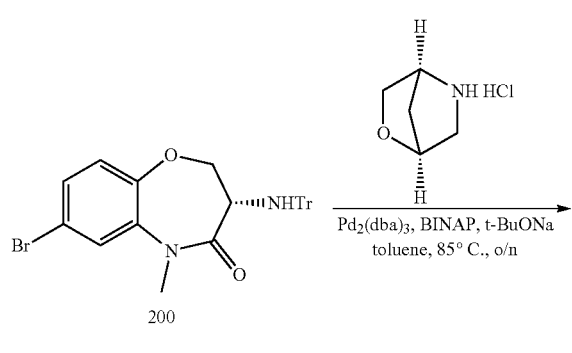
200

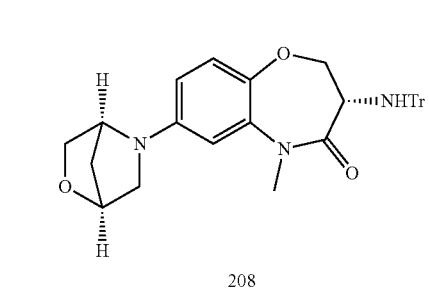
208

Scheme 2E

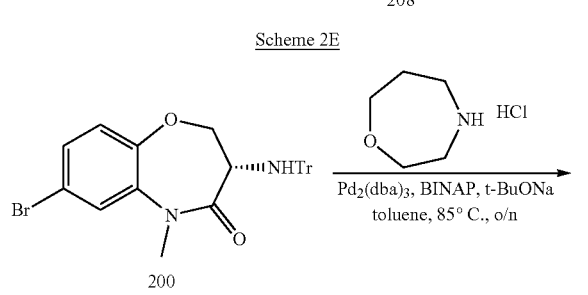
200

-continued

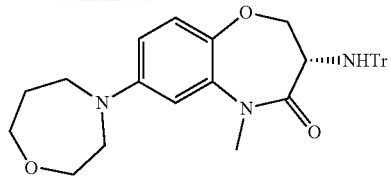
210

Scheme 2F

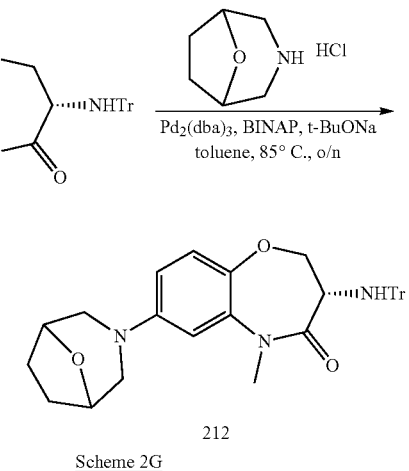
200

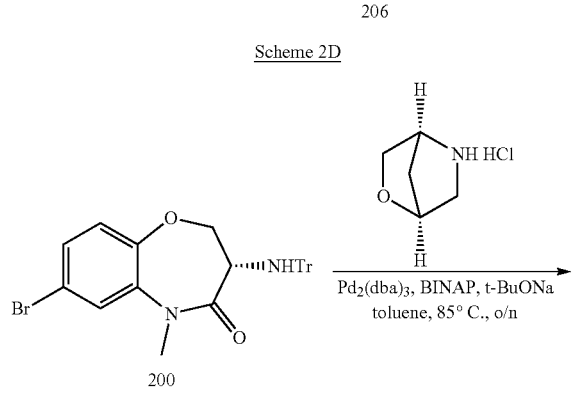
212

Scheme 2G

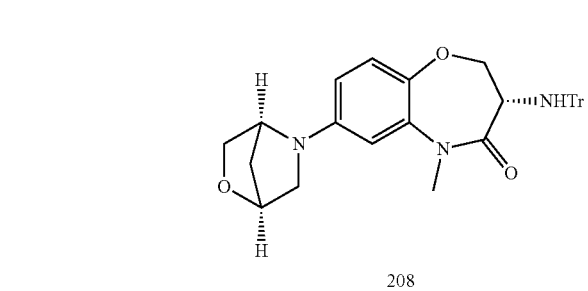
200

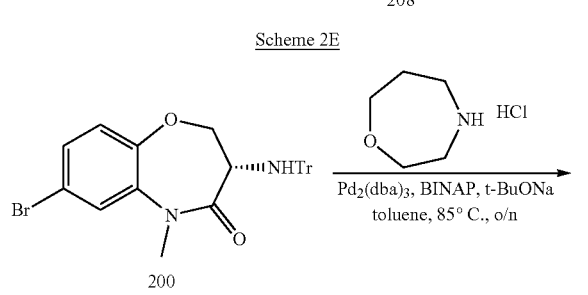
214

Embodiments of the method for making the compounds can further comprise additional steps used to transform $R^1$-functionalized product 104 into desired compounds within the scope of the present disclosure. In some embodiments, these additional steps can include a first deprotection step to provide amine compound 300. Amine compound 300 is then converted into amide compound 304 by reacting the amine compound with a suitable acid coupling partner 302, as illustrated in Scheme 3.

Scheme 3

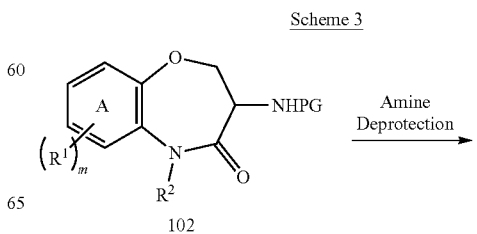
102

Amine Deprotection →

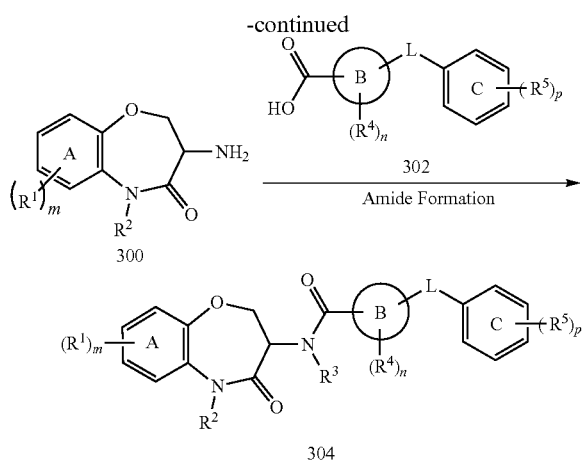

With reference to Scheme 3, deprotection can involve using any suitable reagent capable of removing an amine protecting group ("PG" as shown in Schemes 1 and 3). In some embodiments, an acid is used in the deprotection step, such as TFA. In yet additional embodiments, a base can be used in the deprotection step, such as piperidine. Other acids and bases suitable for deprotection are readily recognized by those of ordinary skill in the art with the benefit of the present disclosure. The amide formation step can be carried out using reagents capable of facilitating amide formation between the free amine of amine compound 300 and the acid functional group of acid coupling partner 302. Suitable coupling partners can be synthesized using methods recognizable to those of ordinary skill in the art with the benefit of the present disclosure, or can be purchased from commercial sources. In some embodiments, propylphosphonic anhydride can be used in combination with a base, such as diisopropylethylamine for amide formation; however, other reagents can be used, such as 2-(7-aza-1H-benzotriazol-1-yl)-N,N,N',N'-tetramethylaminium hexafluorophosphate, 2-(1H-benzotriazol-1-yl)-N,N,N',N'-hexafluorophosphate, 2-(6-chloro-1H-benzotriazol-1-yl)-N,N,N',N'-tetramethylaminium hexafluorophosphate, 1-hydroxybenzotriazole, dicyclohexylcarbodiimide, diisopropylcarbodiimide, N-(3-dimethylaminopropyl)-N'-ethylcarbodiimide-HCl, benzotriazol-1-yloxy-tris(dimethylamino)-phosphonium hexafluorophosphate, benzotriazol-1-yloxy-tripyrrolidino-phosphonium hexafluorophosphate, bromo-tripyrrolidino-phosphonium hexafluorophosphate, and the like, in combination with di-isopropylethyl amine, isopropyl amine, and the like. A suitable solvent also is used, such as dichloromethane ("DCM").

Representative examples of the method steps shown in Scheme 3 are provided below in Schemes 4A-4N.

Scheme 4A

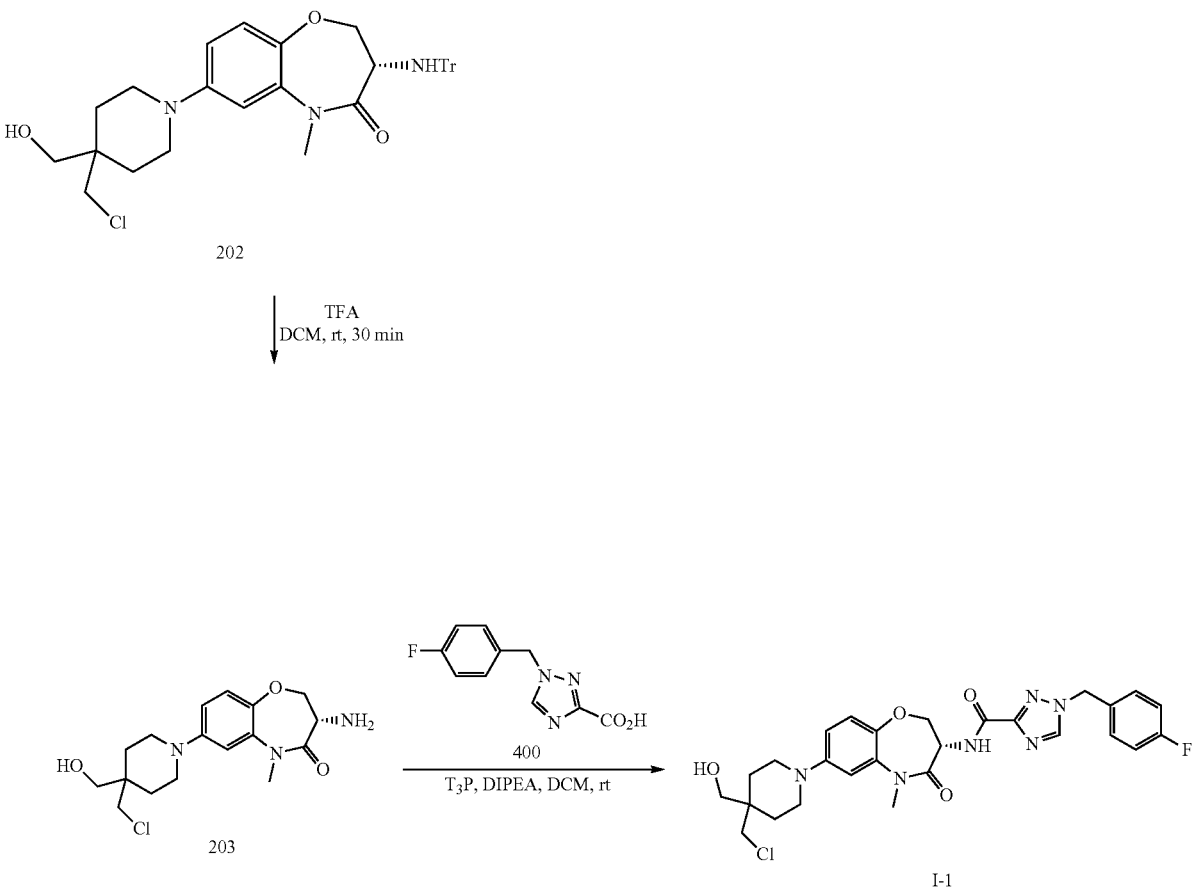

-continued
Scheme 4B
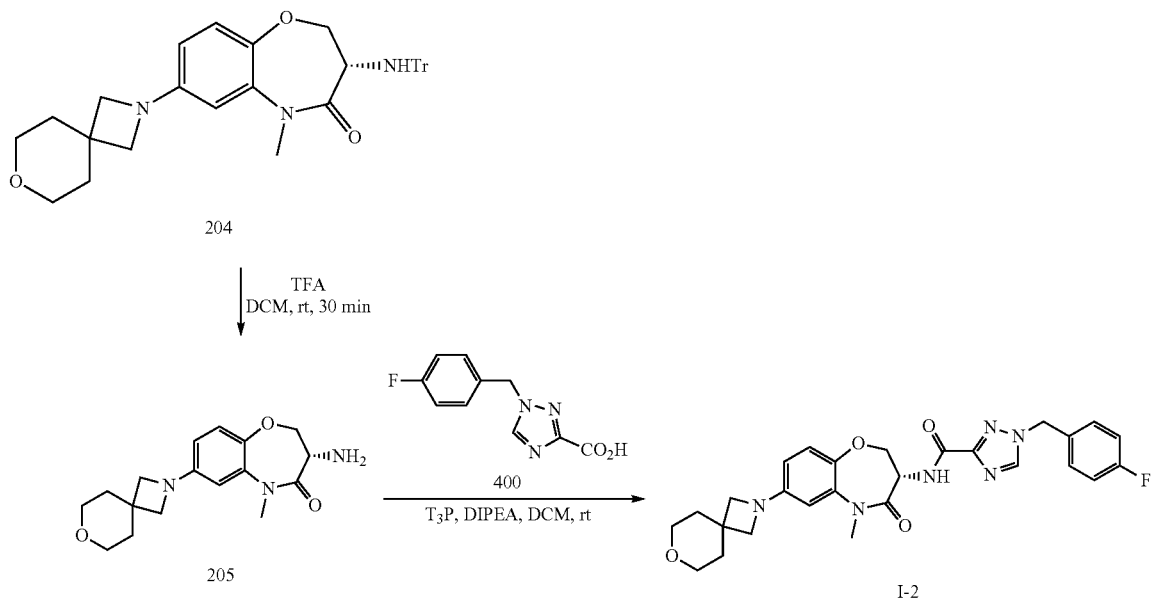
Scheme 4C
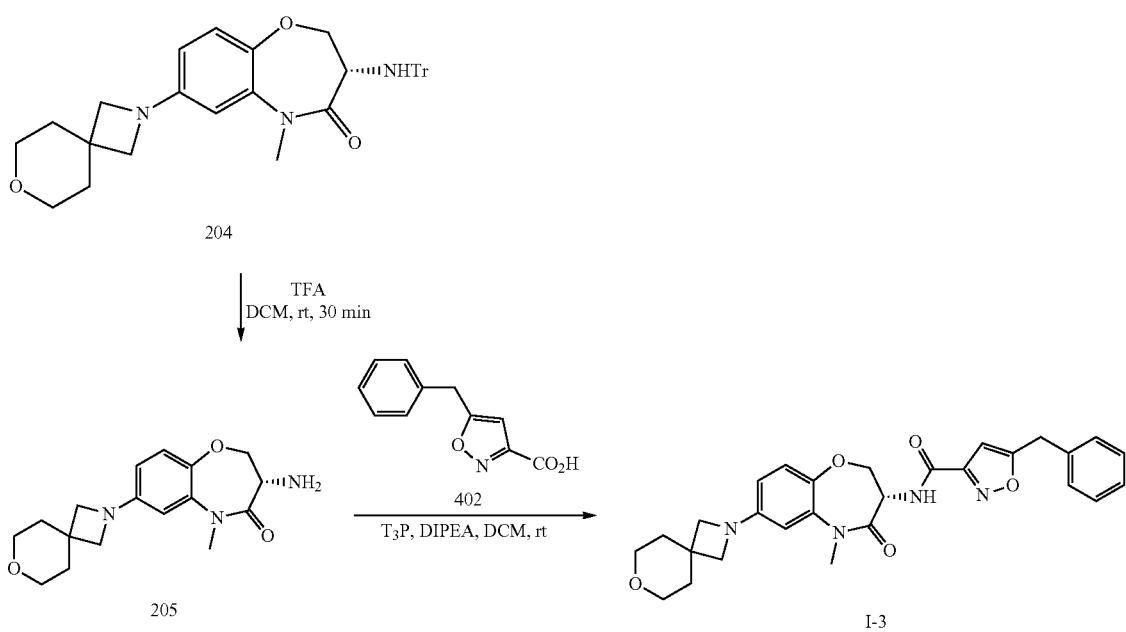
Scheme 4D
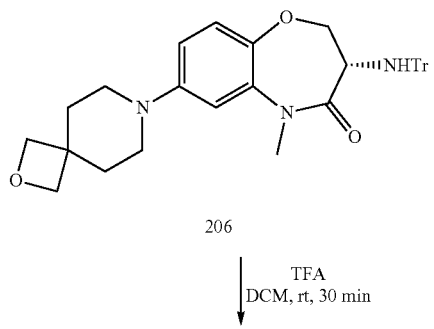

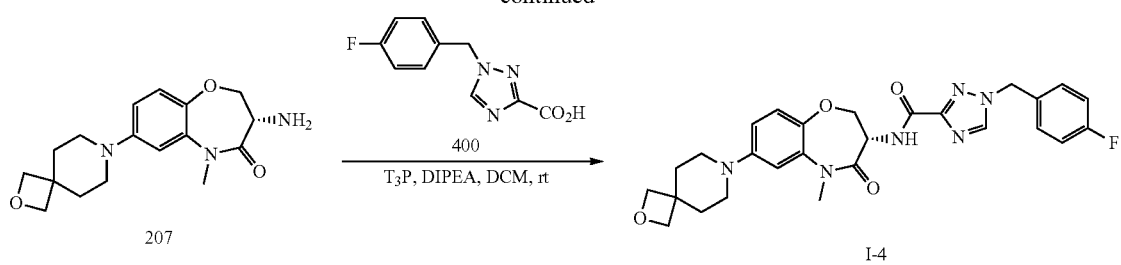
Scheme 4E
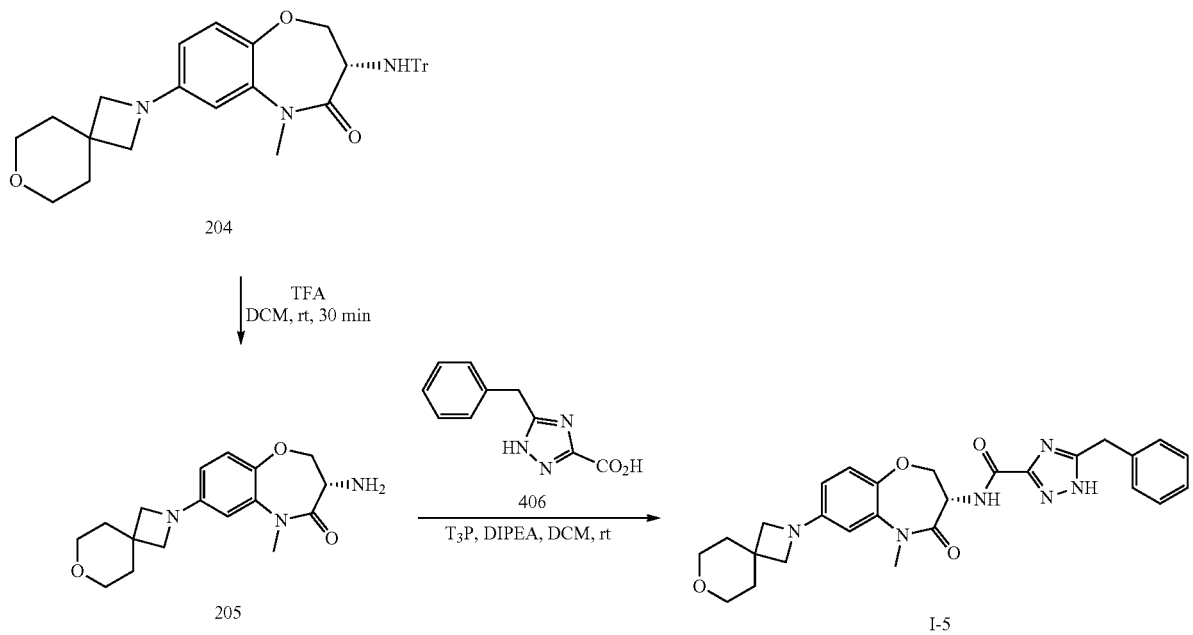
Scheme 4F
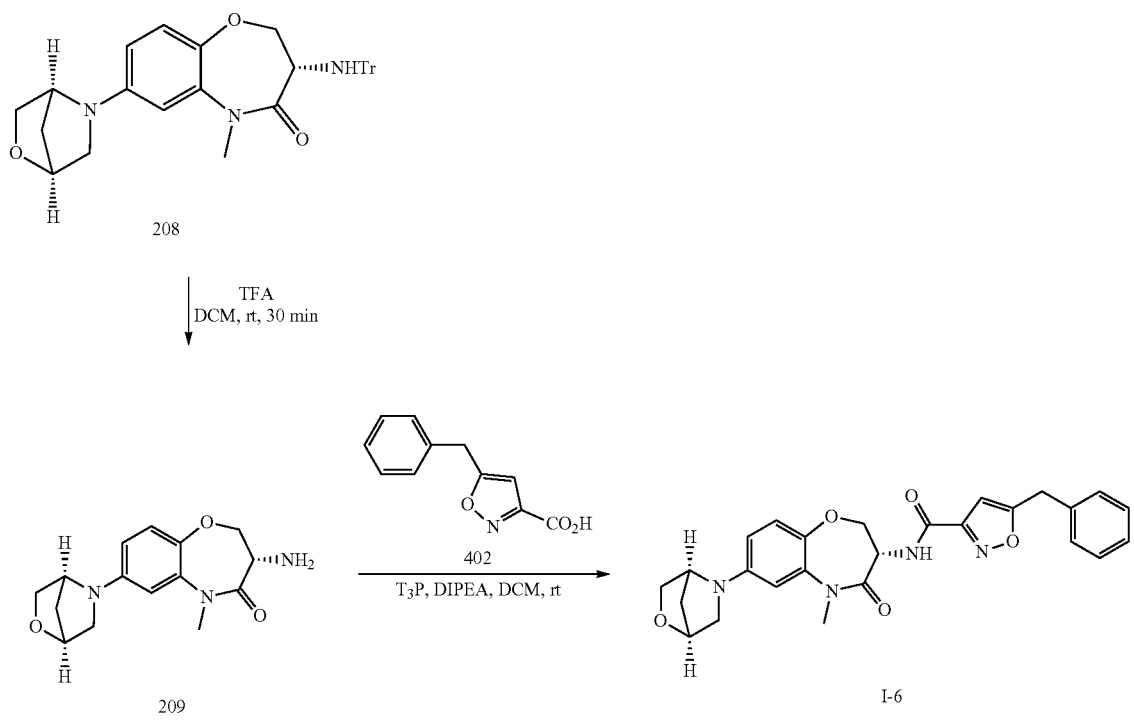

-continued
Scheme 4G
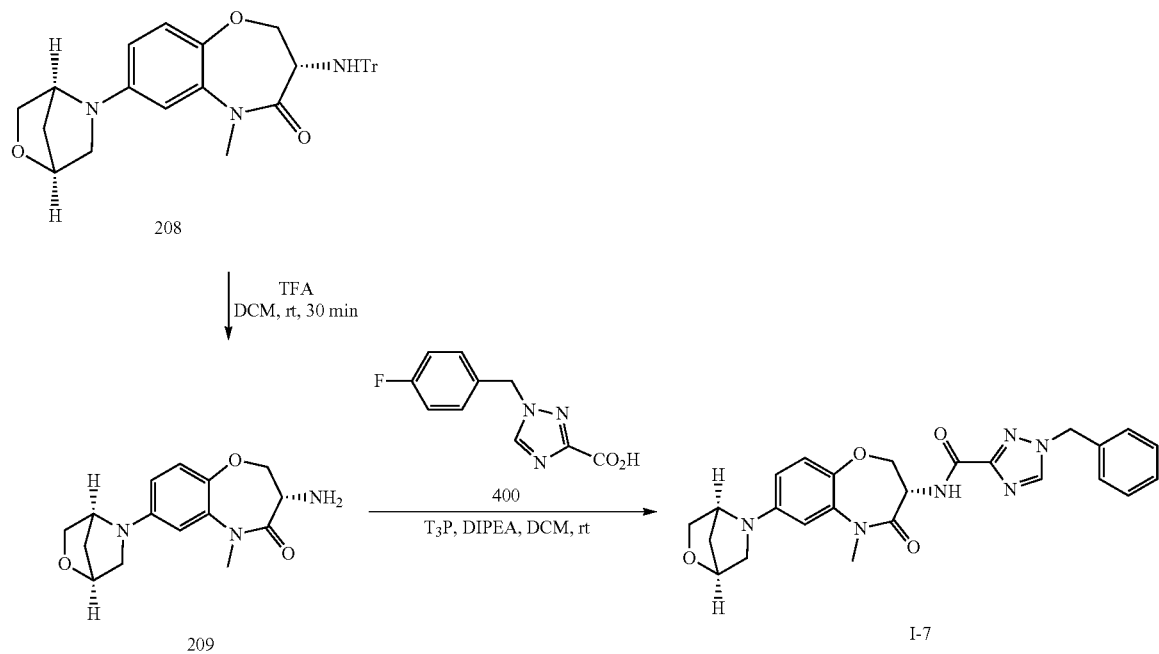
Scheme 4H
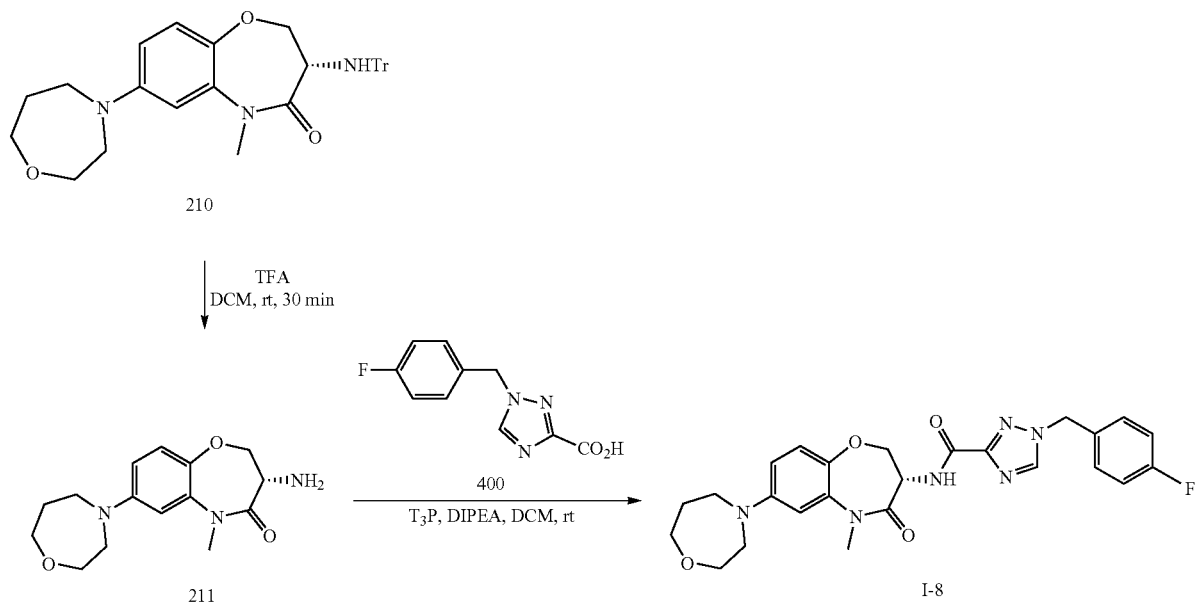
Scheme 4I
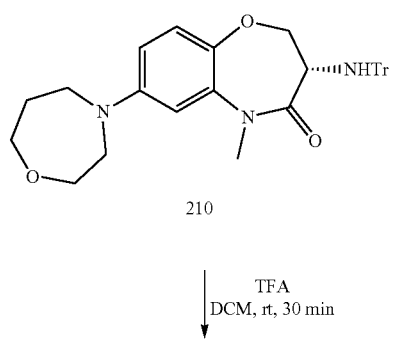

-continued
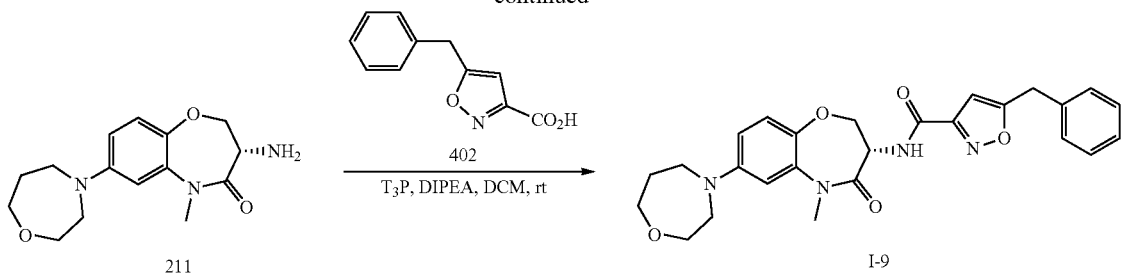
Scheme 4J
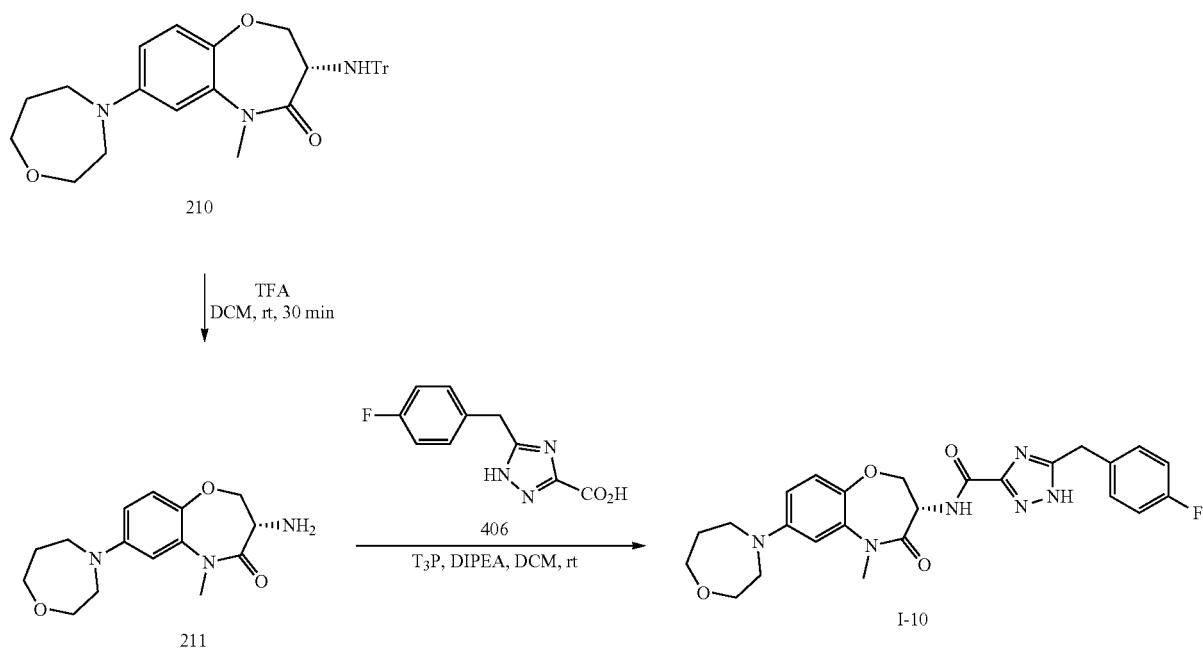
Scheme 4K
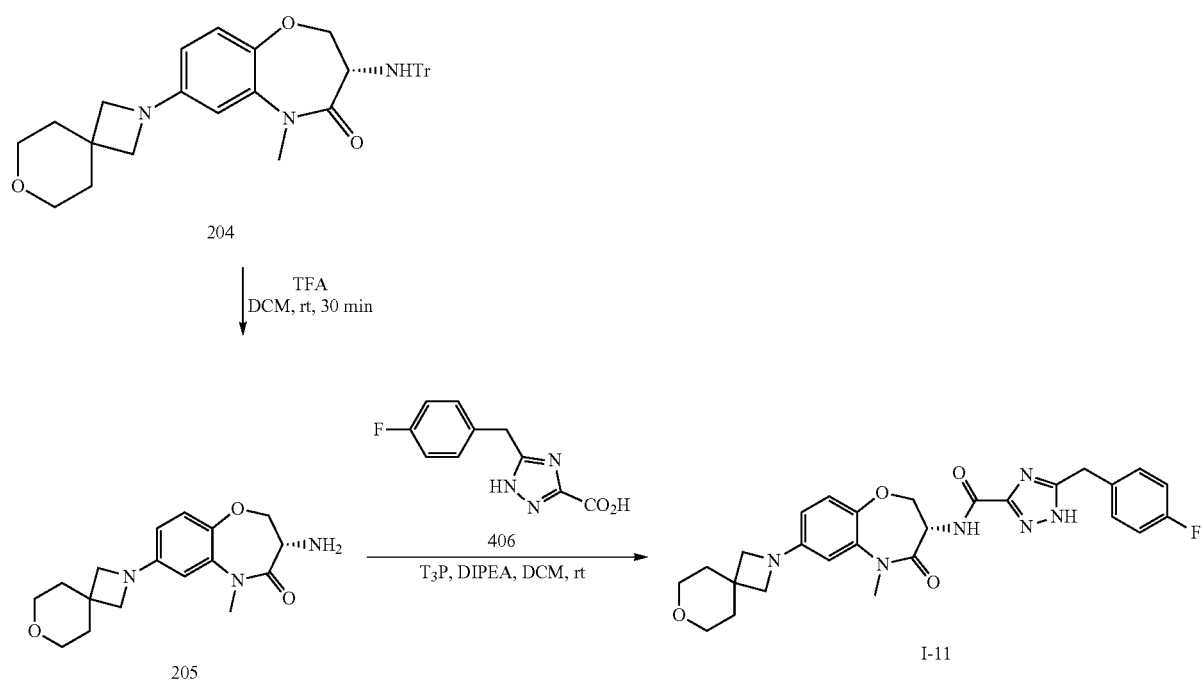

-continued
Scheme 4L
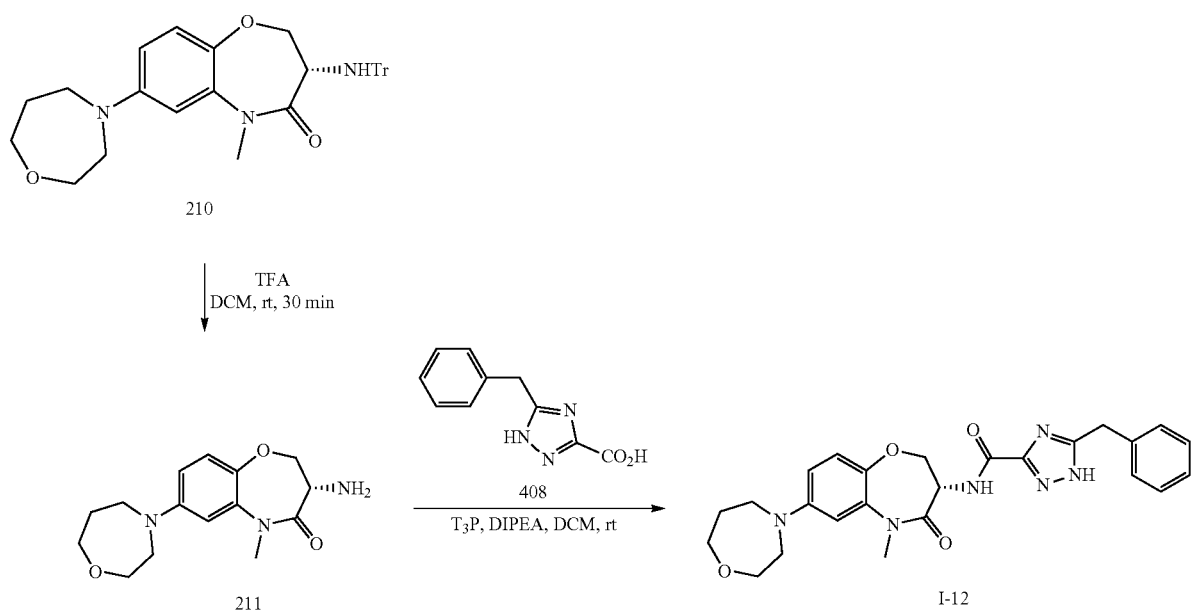
Scheme 4M
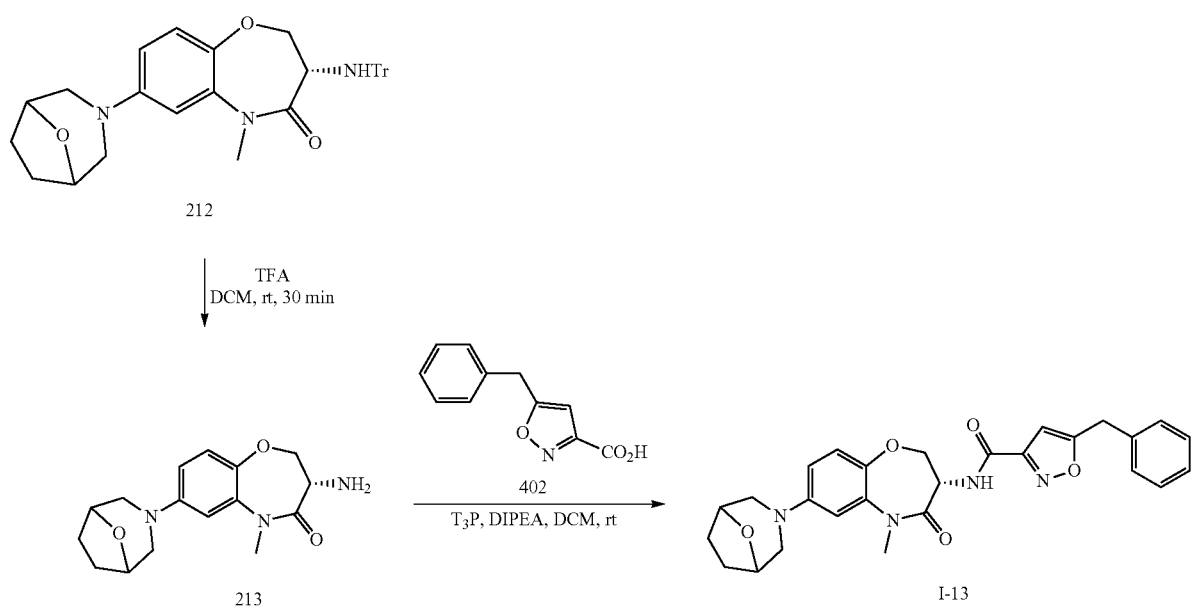
Scheme 4N
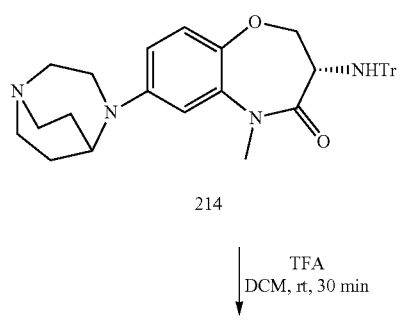

-continued

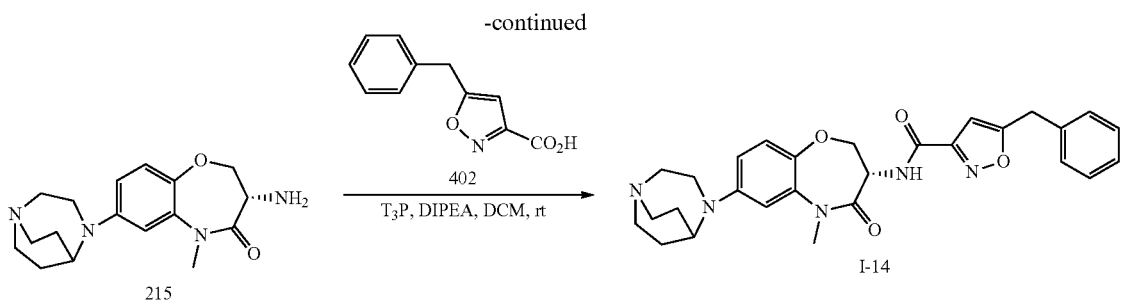

With reference to Schemes 4A-4N above, acid coupling partner 402 can be made using the following procedure: A solution of the ethyl 5-benzylisoxazole-3-carboxylate is dispensed into a solution of NaOH in MeOH and water. After standing for a suitable time at 20° C., the solvent is removed in vacuo. The residue is acidified with dilute HCl and then extracted with EtOAc. The organic phase is washed with water and saturated brine, and dried over sodium sulphate, followed by evaporation in vacuo. The other acid coupling partners described in Schemes 4A-4N can be made using a similar method starting with a suitable starting material (e.g., ethyl 5-benzyl-1H-1,2,4-triazole-3-carboxylate, ethyl 1-benzyl-1H-1,2,4-triazole-3-carboxylate, and fluorinated versions thereof).

IV. Methods of Using Compounds

A. Diseases/Disorders

The disclosed compounds, as well as combinations and/or pharmaceutical compositions thereof, may be used to inhibit a RIP1 kinase by contacting the kinase either in vivo or ex vivo, with a compound or compounds of the present disclosure, or a composition comprising a compound or compounds of the present disclosure. Disclosed compound or compounds, or compositions comprising a disclosed compound or compounds also can be used to ameliorate, treat or prevent a variety of diseases and/or disorders. In particular embodiments, the disclosed compound, combinations of disclosed compounds, or pharmaceutical compositions thereof, may be useful for treating conditions in which inhibition of RIP1 or a pathway involving RIP1 is therapeutically useful. In some embodiments, the compounds directly inhibit RIP1 kinase activity. In certain embodiments, disclosed compounds are useful for treating autoimmune diseases, inflammatory disorders, cardiovascular diseases, nerve disorders, neurodegenerative disorders, allergic disorders, respiratory diseases, kidney diseases, cancers, ischemic conditions, erythrocyte deficiencies, lung and brain injuries (e.g., induced by ischemia-reperfusion or cisplatin and/or cerebrovascular accident), and bacterial and viral infections.

In some embodiments, the disclosed compound, combinations of disclosed compounds, or pharmaceutical compositions thereof, may be used to treat or prevent allergic diseases, amyotrophic lateral sclerosis (ALS), spinal muscular atrophy, systemic lupus erythematosus, rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy, or asthma.

The disclosed compound, combinations of disclosed compounds, or pharmaceutical compositions thereof, may also be useful for treating immune regulatory disorders related to bone marrow or organ transplant rejection or graft-versus-host disease. Examples of inflammatory and immune regulatory disorders that can be treated with the compounds (or pharmaceutical compositions or combinations thereof) include, but are not limited to, transplantation of organs or tissue, graft-versus-host diseases brought about by transplantation, autoimmune syndromes including rheumatoid arthritis, systemic lupus erythematosus, Hashimoto's thyroiditis, multiple sclerosis, systemic sclerosis, systemic inflammatory response syndrome, myasthenia gravis, type I diabetes, uveitis, posterior uveitis, allergic encephalomyelitis, glomerulonephritis, postinfectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, ischemia-reperfusion injuries, inflammatory bowel diseases, necrotizing enterocolitis, intestinal lesions associated with thermal burns, celiac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis or myocardial infarction, scleroderma (including systemic scleroderma), anti-phospholipid syndrome, Wegener's granuloma, Sjögren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, retinal degeneration, retinal detachment, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic liver disease, including alcoholic cirrhosis, alcoholic steatohepatitis, non-alcoholic steatohepatitis (NASH), autoimmune hepatobiliary diseases, acetaminophen toxicity, hepatotoxicity, hepatic failure, fulminant hepatic failure, late-onset hepatic failure, "acute-on-chronic" liver failure, chronic kidney diseases, kidney damage/injury (caused by, for example, nephritis, renal transplant, surgery, administration of nephrotoxic drugs, acute kidney injury), augmentation of chemotherapeutic effect, cytomegalovirus infection, HCMV infection, AIDS, cancer, senile dementia, Parkinson's disease, trauma, or chronic bacterial infection.

In certain embodiments the present compounds are useful for treating nerve pain, including neuropathic pain and inflammation induced pain.

In certain embodiments, the compounds are useful for treating interleukin-1 converting enzyme-associated associated fever syndrome, tumor necrosis factor receptor-associated periodic syndrome, NEMO-deficiency syndrome, HOIL-1 deficiency, linear ubiquitin chain assembly complex deficiency syndrome, lysosomal storage diseases (e.g., Gaucher disease, GM2 gangliosidosis, alpha-mannosidosis, aspartylglucosaminuria, cholesteryl ester storage disease, chronic hexosaminidase A deficiency, cystinosis, Danon disease, Fabry disease, Farber disease, fucosidosis, galactosialidosis, GM1 gangliosidosis, mucolipidosis, infantile free sialic acid storage disease, juvenile hexosaminidase A deficiency, Krabbe disease, lysosomal acid lipase deficiency, metachromatic leukodystrophy, mucopolysaccharidoses disorders, multiple sulfatase deficiency, Niemann-Pick disease, neuronal ceroid lipofuscinoses, Pompe disease, pycnodysostosis, Sandhoff disease, Schindler disease, sialic acid storage disease, Tay-Sach disease, and Wolman disease).

In certain embodiments, the disclosed compound, combinations of disclosed compounds, or pharmaceutical compositions thereof, are useful for treating and/or preventing rheumatoid arthritis, psoriatic arthritis, osteoarthritis, systemic lupus erythematosus, lupus nephritis, ankylosing spondylitis, osteoporosis, systemic sclerosis, multiple sclerosis, psoriasis, in particular pustular psoriasis, type I diabetes, type II diabetes, inflammatory bowel disease (Crohn's disease and ulcerative colitis), hyperimmunoglobulinemia d and periodic fever syndrome, cryopyrin-associated periodic syndromes, Schnitzler's syndrome, systemic juvenile idiopathic arthritis, adult's onset Still's disease, gout, gout flares, pseudogout, sapho syndrome, Castleman's disease, sepsis, stroke, atherosclerosis, celiac disease, DIRA (deficiency of Il-1 receptor antagonist), Alzheimer's disease, Huntington's disease, or Parkinson's disease.

Proliferative diseases that may be treated by the disclosed compound, combinations of disclosed compounds, or pharmaceutical compositions thereof, include benign or malignant tumors, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, undifferentiated carcinoma, papillary carcinoma, seminoma, melanoma, IL-I driven disorders, a MyD88 driven disorder (such as ABC diffuse large B-cell lymphoma (DLBCL), Waldenström's macroglobulinemia, Hodgkin's lymphoma, primary cutaneous T-cell lymphoma or chronic lymphocytic leukemia), smoldering or indolent multiple myeloma, or hematological malignancies (including leukemia, acute myeloid leukemia (AML), DLBCL, ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, myelodysplastic syndromes (MDS), myelofibrosis, polycythemia vera, Kaposi's sarcoma, Waldenström's macroglobulinemia (WM), splenic marginal zone lymphoma, multiple myeloma, plasmacytoma, intravascular large B-cell lymphoma). In particular, the presently disclosed compounds are useful in treating drug resistant malignancies, such as those resistant to JAK inhibitors ibrutinib resistant malignancies, including ibrutinib resistant hematological malignancies, such as ibrutinib resistant CLL and ibrutinib resistant Waldenström's macroglobulinemia.

Examples of allergic disorders that may be treated using the disclosed compound, combinations of disclosed compounds, or pharmaceutical compositions thereof, include, but are not limited to, asthma (e.g. atopic asthma, allergic asthma, atopic bronchial IgE-mediated asthma, non-atopic asthma, bronchial asthma, non-allergic asthma, essential asthma, true asthma, intrinsic asthma caused by pathophysiologic disturbances, essential asthma of unknown or unapparent cause, emphysematous asthma, exercise-induced asthma, emotion-induced asthma, extrinsic asthma caused by environmental factors, cold air induced asthma, occupational asthma, infective asthma caused by or associated with bacterial, fungal, protozoal, or viral infection, incipient asthma, wheezy infant syndrome, bronchiolitis, cough variant asthma or drug-induced asthma), allergic bronchopulmonary aspergillosis (ABPA), allergic rhinitis, perennial allergic rhinitis, perennial rhinitis, vasomotor rhinitis, postnasal drip, purulent or non-purulent sinusitis, acute or chronic sinusitis, and ethmoid, frontal, maxillary, or sphenoid sinusitis.

As another example, rheumatoid arthritis (RA) typically results in swelling, pain, loss of motion and tenderness of target joints throughout the body. RA is characterized by chronically inflamed synovium that is densely crowded with lymphocytes. The synovial membrane, which is typically one cell layer thick, becomes intensely cellular and assumes a form similar to lymphoid tissue, including dendritic cells, T-, B- and NK cells, macrophages and clusters of plasma cells. This process, as well as a plethora of immunopathological mechanisms including the formation of antigen-immunoglobulin complexes, eventually result in destruction of the integrity of the joint, resulting in deformity, permanent loss of function and/or bone erosion at or near the joint. The disclosed compound, combinations of disclosed compounds, or pharmaceutical compositions thereof, may be used to treat, ameliorate or prevent any one, several or all of these symptoms of RA. Thus, in the context of RA, the compounds are considered to provide therapeutic benefit when a reduction or amelioration of any of the symptoms commonly associated with RA is achieved, regardless of whether the treatment results in a concomitant treatment of the underlying RA and/or a reduction in the amount of circulating rheumatoid factor ("RF").

The American College of Rheumatology (ACR) has developed criteria for defining improvement and clinical remission in RA. Once such parameter, the ACR20 (ACR criteria for 20% clinical improvement), requires a 20% improvement in the tender and swollen joint count, as well as a 20% improvement in 3 of the following 5 parameters: patient's global assessment, physician's global assessment, patient's assessment of pain, degree of disability, and level of acute phase reactant. These criteria have been expanded for 50% and 70% improvement in ACR50 and ACR70, respectively. Other criteria include Paulu's criteria and radiographic progression (e.g. Sharp score).

In some embodiments, therapeutic benefit in patients suffering from RA is achieved when the patient exhibits an ACR20. In specific embodiments, ACR improvements of ACRC50 or even ACR70 may be achieved.

B. Formulations and Administration

Pharmaceutical compositions comprising one or more active compounds of the invention may be manufactured by any suitable method, such as mixing, dissolving, granulating, dragee-making, levigating, emulsifying, encapsulating, entrapping or lyophilization processes. The pharmaceutical compositions may be formulated using one or more physiologically acceptable excipients (e.g., diluents, carriers, or auxiliaries), one or more adjuvants, or combinations thereof to provide preparations which can be used pharmaceutically.

The active compound(s) may be formulated in the pharmaceutical compositions per se, or in the form of a pharmaceutically acceptable salt, a stereoisomer, an N-oxide, a tautomer, a hydrate, a solvate, an isotope, or a prodrug thereof. Typically, such salts are more soluble in aqueous solutions than the corresponding free acids and bases, but salts having lower solubility than the corresponding free acids and bases may also be formed.

Pharmaceutical compositions of the invention may take a form suitable for virtually any mode of administration, including, for example, topical, ocular, oral, buccal, systemic, nasal, injection, such as i.v. or i.p., transdermal, rectal, vaginal, etc., or a form suitable for administration by inhalation or insufflation.

For topical administration, the active compound(s), pharmaceutically acceptable salt, stereoisomer, N-oxide, tautomer, hydrate, solvate, isotope, or prodrug may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The pharmaceutical compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile, pyrogen-free water, buffer, dextrose solution, etc., before use. To this end, the active compound(s) maybe dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients, such as: binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); and/or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable excipients such as: suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the active compound, as is well known.

For buccal administration, the pharmaceutical compositions may take the form of tablets or lozenges formulated in conventional manner.

For rectal and vaginal routes of administration, the active compound(s) may be formulated as solutions (for retention enemas) suppositories or ointments containing conventional suppository bases, such as cocoa butter or other glycerides.

For nasal administration or administration by inhalation or insufflation, the active compound(s), pharmaceutically acceptable salt, stereoisomer, N-oxide, tautomer, hydrate, solvate, isotope, or prodrug can be conveniently delivered in the form of an aerosol spray from pressurized packs or a nebulizer with the use of a suitable propellant, e.g.,) dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

A specific example of an aqueous suspension formulation suitable for nasal administration using commercially-available nasal spray devices includes the following ingredients: active compound (0.5 20 mg/ml); benzalkonium chloride (0.1 0.2 mg/mL); polysorbate 80 (TWEEN® 80; 0.5 5 mg/ml); carboxymethylcellulose sodium or microcrystalline cellulose (1 15 mg/ml); phenylethanol (14 mg/ml); and dextrose (20 50 mg/ml). The pH of the final suspension can be adjusted to range from about pH 5 to pH 7, with a pH of about pH 5.5 being typical.

Another specific example of an aqueous suspension suitable for administration of the compounds via inhalation contains 20 mg/mL of the disclosed compound(s), 1% (v/v) polysorbate 80 (TWEEN® 80), 50 mM citrate and/or 0.9% sodium chloride.

For ocular administration, the active compound(s) may be formulated as a solution, emulsion, suspension, etc. suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851, which are incorporated herein by reference.

For prolonged delivery, the active compound(s) can be formulated as a depot preparation for administration by implantation or intramuscular injection. The active ingredient maybe formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption may be used. To this end, permeation enhancers may be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475, which are incorporated herein by reference.

Alternatively, other pharmaceutical delivery systems may be employed. Liposomes and emulsions are well-known examples of delivery vehicles that may be used to deliver active compound(s). Certain organic solvents, such as dimethylsulfoxide (DMSO), may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device may be accompanied by instructions for administration.

C. Dosages

The disclosed compound, pharmaceutical compositions, or combinations of disclosed compounds will generally be used in an amount effective to achieve the intended result, for example, in an amount effective to inhibit a RIP1 kinase and/or to treat, prevent or ameliorate a particular condition. The disclosed compound(s), or pharmaceutical compositions thereof, can be administered therapeutically to achieve therapeutic benefit or prophylactically to achieve a prophylactic benefit. Therapeutic benefit means eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack or a reduction in the frequency or severity of asthmatic episodes. Therapeutic benefit also includes halting or slowing the progression of the disease, regardless of whether improvement is realized.

As known by those of ordinary skill in the art, the preferred dosage of disclosed compounds may depend on various factors, including the age, weight, general health, and severity of the condition of the patient or subject being treated. Dosage also may need to be tailored to the sex of the individual and/or the lung capacity of the individual, when administered by inhalation. Dosage may also be tailored to individuals suffering from more than one condition or those individuals who have additional conditions that affect lung capacity and the ability to breathe normally, for example, emphysema, bronchitis, pneumonia, respiratory distress syndrome, chronic obstructive pulmonary disease, and respiratory infections. Dosage, and frequency of administration of the disclosed compound(s) or pharmaceutical compositions thereof, will also depend on whether the disclosed compound(s) are formulated for treatment of acute episodes of a condition or for the prophylactic treatment of a disorder. A person of ordinary skill in the art will be able to determine the optimal dose for a particular individual.

For prophylactic administration, the disclosed compound, combinations of disclosed compounds, or pharmaceutical compositions thereof, can be administered to a patient or subject at risk of developing one of the previously described conditions. For example, if it is unknown whether a patient or subject is allergic to a particular drug, the disclosed compound, combinations of disclosed compounds, or pharmaceutical compositions thereof, can be administered prior to administration of the drug to avoid or ameliorate an allergic response to the drug. Alternatively, prophylactic administration can be used to avoid or ameliorate the onset of symptoms in a patient diagnosed with the underlying disorder. For example, a disclosed compound(s), or pharmaceutical composition thereof, can be administered to an allergy sufferer prior to expected exposure to the allergen. A disclosed compound, combinations of disclosed compounds, or pharmaceutical compositions thereof, can also be administered prophylactically to healthy individuals who are repeatedly exposed to agents known to one of the above-described maladies to prevent the onset of the disorder. For example, a disclosed compound, combinations of disclosed compounds, or pharmaceutical compositions thereof, can be administered to a healthy individual who is repeatedly exposed to an allergen known to induce allergies, such as latex, in an effort to prevent the individual from developing an allergy. Alternatively, a disclosed compound, combinations of disclosed compounds, or pharmaceutical compositions thereof, can be administered to a patient suffering from asthma prior to partaking in activities which trigger asthma attacks to lessen the severity of, or avoid altogether, an asthmatic episode.

Effective dosages can be estimated initially from in vitro assays. For example, an initial dosage for use in subjects can be formulated to achieve a circulating blood or serum concentration of active compound that is at or above an $IC_{50}$ or $EC_{50}$ of the particular compound as measured in an in vitro assay. Dosages can be calculated to achieve such circulating blood or serum concentrations taking into account the bioavailability of the particular compound. Fingl & Woodbury, "General Principles," In: Goodman and Gilman's The Pharmaceutical Basis of Therapeutics, Chapter 1, pages 1-46, Pergamon Press, and the references cited therein, provide additional guidance concerning effective dosages.

In some embodiments, the disclosed compounds have an $EC_{50}$ from greater than 0 to 20 µM, such as from greater than 0 to 10 µM, from greater than 0 to 5 µM, from greater than 0 to 1 µM, from greater than 0 to 0.5 µM, from greater than 0 to 0.1 µM, or from greater than 0 to 0.05 µM.

Initial dosages can also be estimated from in vivo data, such as animal models. Animal models useful for testing the efficacy of compounds to treat or prevent the various diseases described above are well-known in the art. Suitable animal models of hypersensitivity or allergic reactions are described in Foster, (1995) Allergy 50(21Suppl):6-9, discussion 34-38 and Tumas et al., (2001), J. Allergy Clin. Immunol. 107(6):1025-1033. Suitable animal models of allergic rhinitis are described in Szelenyi et al., (2000), Arzneimittelforschung 50(11):1037-42; Kawaguchi et al., (1994), Clin. Exp. Allergy 24(3):238-244 and Sugimoto et al., (2000), Immunopharmacology 48(1):1-7. Persons of ordinary skill in the art can adapt such information to determine dosages suitable for human administration.

In some embodiments, assays suitable for determining RIP1 activity can be used. Such assay methods can be used to evaluate the efficacy of compound embodiments disclosed herein and/or that can be used to determine amounts/dosages of the compound embodiments that can provide a desired efficacy. In some embodiments, the assay can be an ADP-Glo™ assay that assesses the ability of a compound embodiment to inhibit RIP1. In other embodiments, whole cell assays using mouse and/or human cells, such as U937 and/or L929 cell necroptosis assays, can be performed to determine safe and effective doses of compounds that can be used in human in vivo studies. Using these whole cell assays, the compound's activity against human and/or murine RIP1 can be assessed in an in vitro context, which then allows a person of ordinary skill in the art to determine safe and effective dosages for in vivo use. Yet another assay that can be used to evaluate the activity of compound embodiments described herein to treat a disease or condition involving RIP1 is an acute hypothermia mouse model, which assesses the compound's ability to inhibit TNF-alpha induced hypothermia. Each of these assays, and various results from using these assays, are described in detail in the Examples section of the present disclosure.

Dosage amounts of disclosed compounds will typically be in the range of from greater than 0 mg/kg/day, such as 0.0001 mg/kg/day or 0.001 mg/kg/day or 0.01 mg/kg/day, up to at least about 100 mg/kg/day. More typically, the dosage (or effective amount) may range from about 0.0025 mg/kg to about 1 mg/kg administered at least once per day, such as from 0.01 mg/kg to about 0.5 mg/kg or from about 0.05 mg/kg to about 0.15 mg/kg. The total daily dosage typically ranges from about 0.1 mg/kg to about 5 mg/kg or to about 20 mg/kg per day, such as from 0.5 mg/kg to about 10 mg/kg per day or from about 0.7 mg/kg per day to about 2.5 mg/kg/day. Dosage amounts can be higher or lower depending upon, among other factors, the activity of the disclosed compound, its bioavailability, the mode of administration, and various factors discussed above.

Dosage amount and dosage interval can be adjusted for individuals to provide plasma levels of the disclosed compound that are sufficient to maintain therapeutic or prophylactic effect. For example, the compounds can be administered once per day, multiple times per day, once per week, multiple times per week (e.g., every other day), one per month, multiple times per month, or once per year, depending upon, amongst other things, the mode of administration, the specific indication being treated, and the judgment of the prescribing physician. Persons of ordinary skill in the art will be able to optimize effective local dosages without undue experimentation.

Pharmaceutical compositions comprising one or more of the disclosed compounds typically comprise from greater than 0 up to 99% of the disclosed compound, or compounds, and/or other therapeutic agent by total weight percent. More typically, pharmaceutical compositions comprising one or more of the disclosed compounds comprise from about 1 to about 20 total weight percent of the disclosed compound and other therapeutic agent, and from about 80 to about 99 weight percent of a pharmaceutically acceptable excipient. In some embodiments, the pharmaceutical composition can further comprise an adjuvant.

Preferably, the disclosed compound, combinations of disclosed compounds, or pharmaceutical compositions thereof, will provide therapeutic or prophylactic benefit without causing substantial toxicity. Toxicity of the disclosed compound can be determined using standard pharmaceutical procedures. The dose ratio between toxic and therapeutic (or prophylactic) effect is the therapeutic index. Disclosed compounds that exhibit high therapeutic indices are preferred.

V. Examples

Example 1

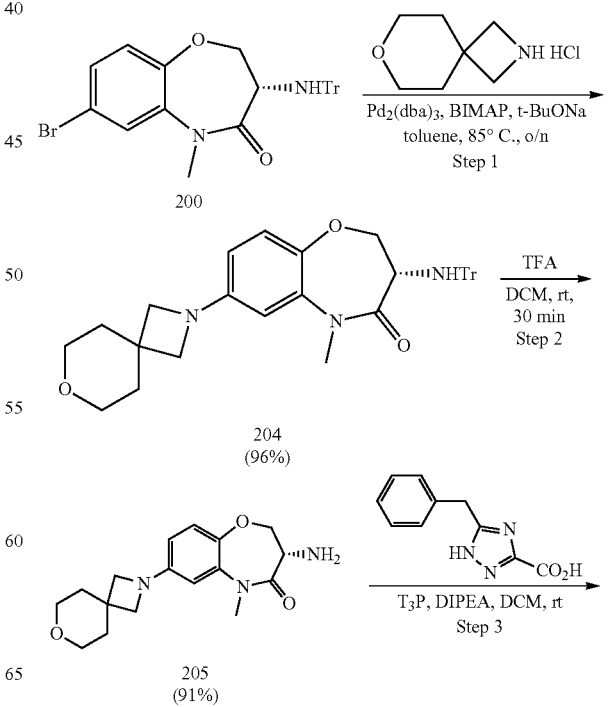

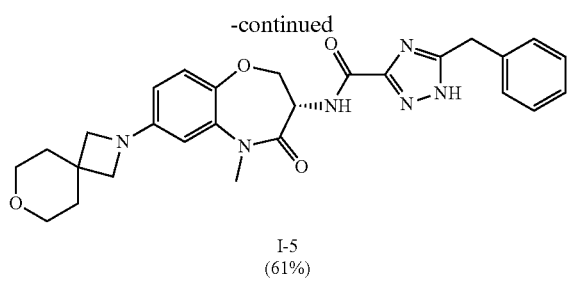

I-5
(61%)

Step 1—A mixture of (S)-7-bromo-5-methyl-3-(tritylamino)-2,3-dihydrobenzo[b][1,4]oxazepin-4(5H)-one 200 (which is made using a method as illustrated below; 0.25 g, 0.49 mmol), 7-oxa-2-azaspiro[3.5]nonane hydrochloride (0.10 g, 0.60 mmol), Pd₂(dba)₃ (0.025 g, 0.027 mmol), rac-BINAP (0.05 g, 0.08 mmol) and NaO$^t$Bu (0.12 g, 1.3 mmol) in toluene (5 mL) was stirred at 85° C. for 16 hours. The reaction mixture was then concentrated under reduced pressure to give a residue, which was purified by chromatography eluting with ethyl acetate/hexanes (3/7) to provide (S)-5-methyl-7-(7-oxa-2-azaspiro[3.5]nonan-2-yl)-3-(tritylamino)-2,3-dihydrobenzo[b][1,4]oxazepin-4(5H)-one 204 as a brown solid (0.26 g, 96%).

Step 2—To a mixture of (S)-5-methyl-7-(7-oxa-2-azaspiro[3.5]nonan-2-yl)-3-(tritylamino)-2,3-dihydrobenzo[b][1,4]oxazepin-4(5H)-one 204 (0.26 g, 0.46 mmol) in dichlomethane (6 mL) was added trifluoroactic acid (15.7 mmol, 1.2 mL). The resulting solution was stirred at room temperature for 0.5 hours. The solution was then concentrated under reduced pressure. The residue was dissolved in methanol and subsequently basified by 28% ammonium hydroxide solution. The resulting mixture was re-concentrated under reduced pressure to give a residue, which was purified by chromatography eluting with ethyl acetate to dichloromethane/MeOH (10/2) to provide (S)-3-amino-5-methyl-7-(7-oxa-2-azaspiro[3.5]nonan-2-yl)-2,3-dihydrobenzo[b][1,4]oxazepin-4(5H)-one 205 as a pale white solid (0.16 g, 91%). ¹H NMR (CD₃OD, 400 MHz) 6.96 (d, J=8.8 Hz, 1H), 6.38 (d, J=2.8 Hz, 1H), 6.32 (dd, J=8.8, 2.8 Hz, 1H), 4.30 (m, 1H), 3.98 (m, 1H), 3.72 (m, 1H), 3.64 (m, 8H), 3.33 (s, 3H), 1.81 (m, 4H) ppm; MS m/e: 318.2 (M+H)⁺.

Step 3—To a stirred mixture of (S)-3-amino-5-methyl-7-(7-oxa-2-azaspiro[3.5]nonan-2-yl)-2,3-dihydrobenzo[b][1,4]oxazepin-4(5H)-one 3 (0.025 g, 0.08 mmol) 205 and 5-benzyl-1H-1,2,4-triazole-3-carboxylic acid (0.018 mg, 0.09 mmol) in dichloromethane (1 mL) was added N,N-diisopropylethylamine (0.05 ml, 0.3 mmol) and T₃P (propylphosphonic anhydride solution (50% wt. % in ethyl acetate). The reaction mixture was stirred at room temperature for 3 hours and quenched with water. The organic layer was separated and concentrated under reduced pressure to give a residue, which was purified by chromatography eluting with ethyl acetate/hexanes (3/7 to 9/1) to provide (S)-5-benzyl-N-(5-methyl-4-oxo-7-(7-oxa-2-azaspiro[3.5]nonan-2-yl)-2,3,4,5-tetrahydrobenzo[b][1,4]oxazepin-3-yl)-1H-1,2,4-triazole-3-carboxamide I-5 as a white solid (0.02 g, 61%). ¹H NMR (CD₃OD, 400 MHz) 7.26 (m, 5H), 7.01 (d, J=8.8 Hz, 1H), 6.43 (d, J=2.8 Hz, 1H), 6.36 (dd, J=9.0, 2.4 Hz, 1H), 4.96 (m, 1H), 4.47 (m, 1H), 4.25 (m, 1H), 4.13 (s, 2H), 3.64 (m, 8H), 3.35 (s, 3H), 1.82 (m, 4H) ppm; MS m/e: 503.3 (M+H)⁺.

Example 2

The synthetic procedure described above was adapted as described herein to make compound I-1 below.

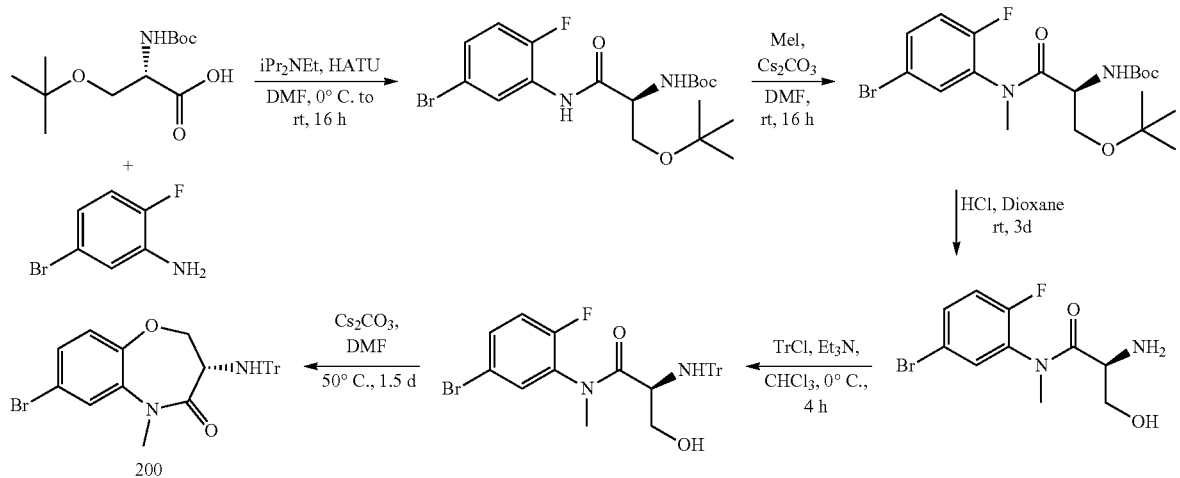

Exemplary Method for Making Compound 200

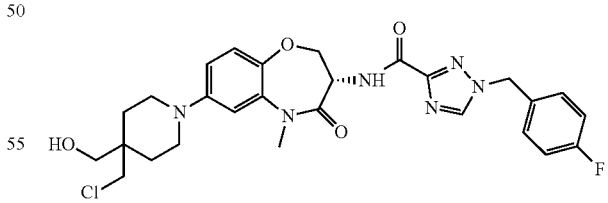

I-1

(S)—N-(7-(4-(chloromethyl)-4-(hydroxymethyl)piperidin-1-yl)-5-methyl-4-oxo-2,3,4,5-tetrahydrobenzo[b][1,4]oxazepin-3-yl)-1-(4-fluorobenzyl)-1H-1,2,4-triazole-3-carboxamide ¹H NMR (CD₃OD, 400 MHz) 8.56 (s, 1H), 7.82 (m, 1H), 7.65 (m, 1H), 7.38 (m, 2H), 7.07 (m, 3H), 5.43 (s, 2H), 5.00 (m, 1H), 4.60 (m, 1H), 4.49 (m, 1H), 4.40 (m, 2H), 3.43 (s, 3H), 2.38 (m, 2H), 2.02 (m, 2H), 1.35 (m, 6H) ppm; MS m/e: 557.3 (M+H)⁺.

Example 3

The synthetic procedure described above was adapted as described herein to make compound I-2 below.

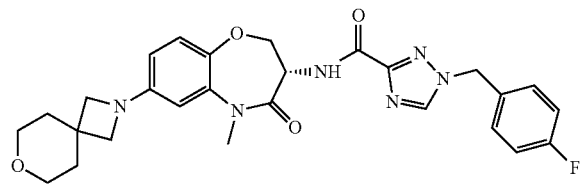

I-2

(S)-1-(4-fluorobenzyl)-N-(5-methyl-4-oxo-7-(7-oxa-2-azaspiro[3.5]nonan-2-yl)-2,3,4,5-tetrahydrobenzo[b][1,4]oxazepin-3-yl)-1H-1,2,4-triazole-3-carboxamide $^1$H NMR (CDCl$_3$, 400 MHz) 8.01 (m, 2H), 7.26 (m, 2H), 7.05 (m, 3H), 6.26 (dd, J=9.0, 2.8 Hz, 1H), 6.18 (d, J=2.8 Hz, 1H), 5.33 (s, 2H), 5.08 (m, 1H), 4.65 (m, 1H), 4.13 (m, 1H), 3.65 (m, 8H), 3.38 (s, 3H), 1.85 (m, 4H) ppm; MS m/e: 521.3 (M+H)$^+$.

Example 4

The synthetic procedure described above was adapted as described herein to make compound I-3 below.

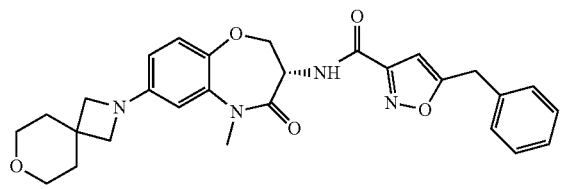

I-3

(S)-5-benzyl-N-(5-methyl-4-oxo-7-(7-oxa-2-azaspiro[3.5]nonan-2-yl)-2,3,4,5-tetrahydrobenzo[b][1,4]oxazepin-3-yl)isoxazole-3-carboxamide $^1$H NMR (CDCl$_3$, 400 MHz) 7.69 (m, 1H), 7.26 (m, 5H), 7.01 (d, J=8.8 Hz, 1H), 6.26 (m, 2H), 6.18 (d, J=2.8 Hz, 1H), 5.00 (m, 1H), 4.61 (m, 1H), 4.13 (m, 1H), 4.08 (s, 2H), 3.64 (m, 8H), 3.38 (s, 3H), 1.84 (m, 4H) ppm; MS m/e: 503.3 (M+H)$^+$.

Example 5

The synthetic procedure described above was adapted as described herein to make compound I-4 below.

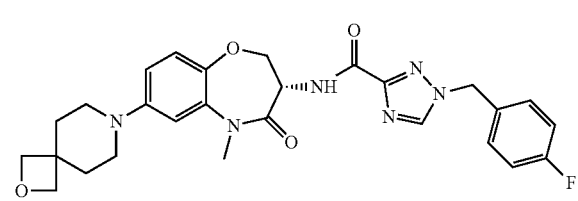

I-4

(S)-1-(4-fluorobenzyl)-N-(5-methyl-4-oxo-7-(2-oxa-7-azaspiro[3.5]nonan-7-yl)-2,3,4,5-tetrahydrobenzo[b][1,4]oxazepin-3-yl)-1H-1,2,4-triazole-3-carboxamide $^1$H NMR (CD$_3$OD, 400 MHz) 8.56 (s, 1H), 7.40 (m, 2H), 7.09 (m, 3H), 6.96 (m, 1H), 6.90 (m, 1H), 5.45 (s, 2H), 4.97 (m, 1H), 4.51 (m, 1H), 4.49 (s, 4H), 4.31 (m, 1H), 3.38 (s, 3H), 3.12 (m, 4H), 2.01 (m, 4H) ppm; MS m/e: 521.3 (M+H)$^+$.

Example 6

The synthetic procedure described above was adapted as described herein to make compound I-6 below.

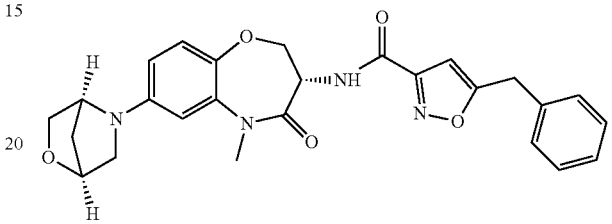

I-6

N—((S)-7-((1S,4S)-2-oxa-5-azabicyclo[2.2.1]heptan-5-yl)-5-methyl-4-oxo-2,3,4,5-tetrahydrobenzo[b][1,4]oxazepin-3-yl)-5-benzylisoxazole-3-carboxamide $^1$H NMR (CD$_3$OD, 400 MHz) 7.28 (m, 5H), 7.02 (d, J=8.8 Hz, 1H), 6.58 (m, 1H), 6.53 (dd, J=8.4, 2.8 Hz, 1H), 6.37 (s, 1H), 4.96 (m, 1H), 4.63 (m, 1H), 4.51 (m, 1H), 4.45 (m, 1H), 4.30 (m, 1H), 4.14 (s, 2H), 3.83 (m, 2H), 3.55 (m, 1H), 3.36 (s, 3H), 3.07 (m, 1H), 2.02 (m, 1H), 1.93 (m, 1H) ppm; MS m/e: 475.1 (M+H)$^+$.

Example 7

The synthetic procedure described above was adapted as described herein to make compound I-7 below.

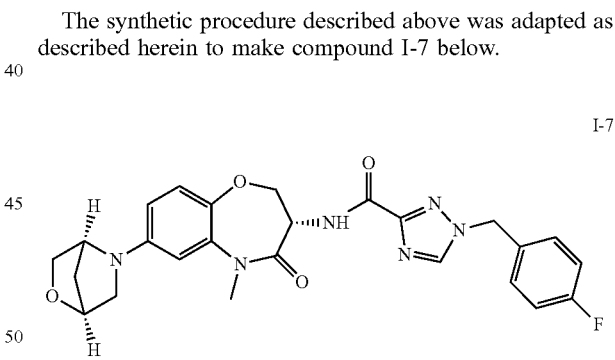

I-7

N—((S)-7-((1S,4S)-2-oxa-5-azabicyclo[2.2.1]heptan-5-yl)-5-methyl-4-oxo-2,3,4,5-tetrahydrobenzo[b][1,4]oxazepin-3-yl)-1-(4-fluorobenzyl)-1H-1,2,4-triazole-3-carboxamide $^1$H NMR (CD$_3$OD, 400 MHz) 8.54 (s, 1H), 7.38 (m, 2H), 7.06 (m, 3H), 6.59 (d, J=2.8 Hz, 1H), 6.54 (dd, J=8.4, 2.8 Hz, 1H), 5.43 (s, 2H), 4.97 (m, 1H), 4.63 (m, 1H), 4.49 (m, 2H), 4.26 (m, 1H), 3.83 (m, 2H), 3.55 (m, 1H), 3.36 (s, 3H), 3.07 (m, 1H), 2.01 (m, 1H), 1.94 (m, 1H) ppm; MS m/e: 493.3 (M+H)$^+$.

Example 8

The synthetic procedure described above was adapted as described herein to make compound I-8 below.

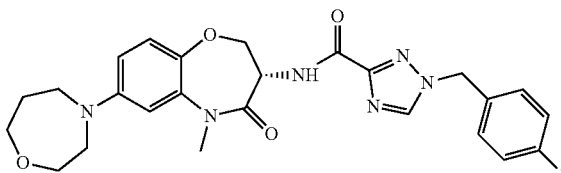

I-8

(S)-1-(4-fluorobenzyl)-N-(5-methyl-7-(1,4-oxazepan-4-yl)-4-oxo-2,3,4,5-tetrahydrobenzo[b][1,4]oxazepin-3-yl)-1H-1,2,4-triazole-3-carboxamide $^1$H NMR (CD$_3$OD, 400 MHz) 8.55 (s, 1H), 7.37 (m, 2H), 7.08 (m, 3H), 6.72 (m, 2H), 5.43 (s, 2H), 4.98 (m, 1H), 4.49 (m, 1H), 4.26 (m, 1H), 3.83 (m, 2H), 3.70 (m, 2H), 3.64 (m, 4H), 3.37 (s, 3H), 2.01 (m, 2H) ppm; MS m/e: 495.3 (M+H)$^+$.

Example 9

The synthetic procedure described above was adapted as described herein to make compound I-9 below.

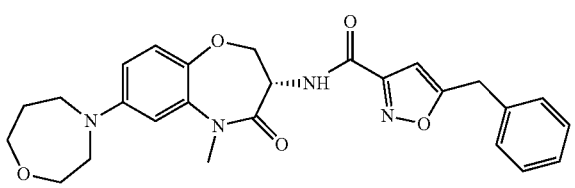

I-9

(S)-5-benzyl-N-(5-methyl-7-(1,4-oxazepan-4-yl)-4-oxo-2,3,4,5 tetrahydrobenzo[b][1,4]oxazepin-3-yl)isoxazole-3-carboxamide $^1$H NMR (CD$_3$OD, 400 MHz) 7.28 (m, 5H), 7.02 (d, J=9.2 Hz, 1H), 6.69 (d, J=2.8 Hz, 1H), 6.65 (dd, J=9.0, 3.2 Hz, 1H), 6.36 (s, 1H), 4.97 (m, 1H), 4.44 (m, 1H), 4.29 (m, 1H), 4.14 (s, 2H), 3.80 (m, 2H), 3.68 (m, 2H), 3.63 (m, 4H), 3.36 (s, 3H), 1.99 (m, 2H) ppm; MS m/e: 477.3 (M+H)$^+$.

Example 10

The synthetic procedure described above was adapted as described herein to make compound I-10 below.

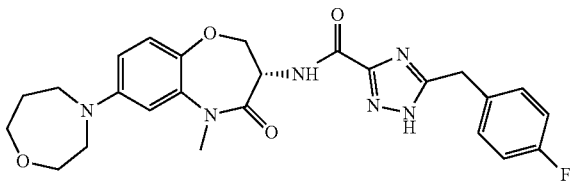

I-10

(S)-5-(4-fluorobenzyl)-N-(5-methyl-7-(1,4-oxazepan-4-yl)-4-oxo-2,3,4,5-tetrahydrobenzo[b][1,4]oxazepin-3-yl)-1H-1,2,4-triazole-3-carboxamide $^1$H NMR (CD$_3$OD, 400 MHz) 7.28 (m, 2H), 7.03 (m, 3H), 6.66 (m, 2H), 4.98 (m, 1H), 4.49 (m, 1H), 4.25 (m, 1H), 4.13 (s, 2H), 3.81 (m, 2H), 3.68 (m, 2H), 3.62 (m, 4H), 3.37 (s, 3H), 1.99 (m, 2H) ppm; MS m/e: 495.3 (M+H)$^+$.

Example 11

The synthetic procedure described above was adapted as described herein to make compound I-11 below.

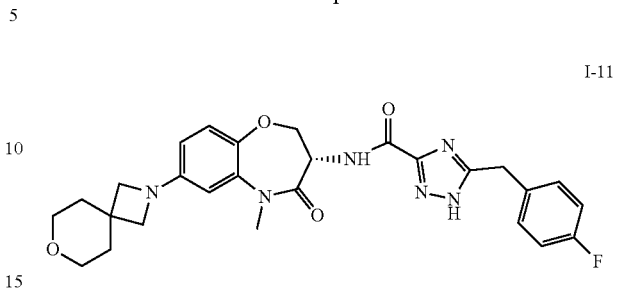

I-11

(S)-5-(4-fluorobenzyl)-N-(5-methyl-4-oxo-7-(7-oxa-2-azaspiro[3.5]nonan-2-yl)-2,3,4,5-tetrahydrobenzo[b][1,4]oxazepin-3-yl)-1H-1,2,4-triazole-3-carboxamide $^1$H NMR (CD$_3$OD, 400 MHz) 7.27 (m, 2H), 7.03 (m, 3H), 6.43 (d, J=2.4 Hz, 1H), 6.37 (dd, J=8.8, 2.8 Hz, 1H), 4.96 (m, 1H), 4.48 (m, 1H), 4.25 (m, 1H), 4.13 (s, 2H), 3.65 (m, 8H), 3.36 (s, 3H), 1.83 (m, 4H) ppm; MS m/e: 519.3 (M−H)$^-$.

Example 12

The synthetic procedure described above was adapted as described herein to make compound I-12 below.

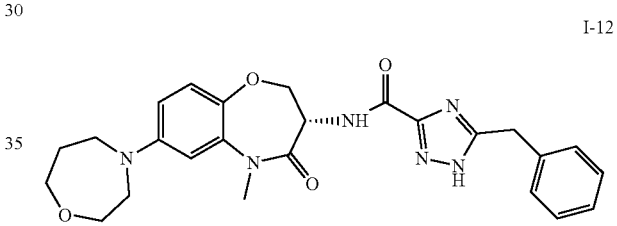

I-12

(S)-5-benzyl-N-(5-methyl-7-(1,4-oxazepan-4-yl)-4-oxo-2,3,4,5-tetrahydrobenzo[b][1,4]oxazepin-3-yl)-1H-1,2,4-triazole-3-carboxamide $^1$H NMR (CD$_3$OD, 400 MHz) 7.26 (m, 4H), 7.02 (d, J=9.2 Hz, 1H), 6.69 (d, J=3.2 Hz, 1H), 6.66 (m, 1H), 4.99 (m, 1H), 4.49 (m, 1H), 4.25 (m, 1H), 4.14 (s, 2H), 3.82 (m, 2H), 3.69 (m, 2H), 3.62 (m, 4H), 3.37 (s, 3H), 1.99 (m, 2H) ppm; MS m/e: 475.3 (M−H)$^-$.

Example 13

The synthetic procedure described above was adapted as described herein to make compound I-13 below.

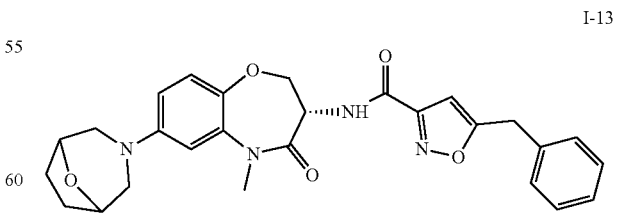

I-13

N-((3S)-7-(8-oxa-3-azabicyclo[3.2.1]octan-3-yl)-5-methyl-4-oxo-2,3,4,5-tetrahydrobenzo[b][1,4]oxazepin-3-yl)-5-benzylisoxazole-3-carboxamide $^1$H NMR (CD$_3$OD, 400 MHz) 7.32 (m, 5H), 7.04 (d, J=8.8 Hz, 1H), 6.81 (d, J=2.8

Hz, 1H), 6.76 (dd, J=8.8, 2.8 Hz, 1H), 6.37 (s, 1H), 4.94 (m, 1H), 4.44 (m, 3H), 4.31 (m, 1H), 4.14 (s, 2H), 3.37 (m, 5H), 2.90 (m, 2H), 1.95 (m, 4H) ppm; MS m/e: 489.1 (M+H)$^+$.

Example 14

The synthetic procedure described above was adapted as described herein to make compound I-14 below.

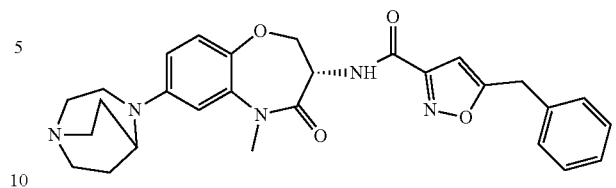

I-14

(S)—N-(7-(1,4-diazabicyclo[3.2.2]nonan-4-yl)-5-methyl-4-oxo-2,3,4,5-tetrahydrobenzo[b][1,4]oxazepin-3-yl)-5-benzylisoxazole-3-carboxamide MS m/e: 502.3 (M+H)$^+$.

Other exemplary compounds are described below.

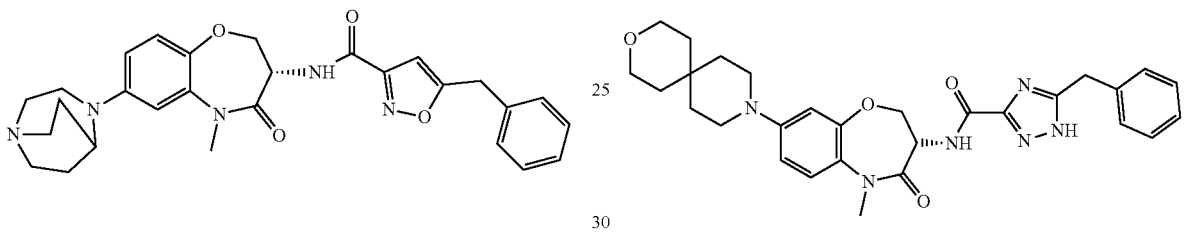

I-14

(S)-5-benzyl-N-(7-(2-benzyl-1-oxo-2,8-diazaspiro[4.5]decan-8-yl)-5-methyl-4-oxo-2,3,4,5-tetrahydrobenzo[b][1,4]oxazepin-3-yl)-1H-1,2,4-triazole-3-carboxamide (S)-5-benzyl-N-(5-methyl-4-oxo-8-(3-oxa-9-azaspiro[5.5]undecan-9-yl)-2,3,4,5-tetrahydrobenzo[b][1,4]oxazepin-3-yl)-1H-1,2,4-triazole-3-carboxamide $^1$H NMR (400 MHz, Chloroform-d) δ 8.03-7.93 (m, 1H), 7.34-7.23 (m, 4H), 7.21-7.18 (m, 2H), 7.14-7.09 (m, 5H), 6.96 (br d, J=8.8 Hz, 1H), 6.72 (br d, J=8.9 Hz, 1H), 6.65 (br s, 1H), 4.94 (t, J=9.2 Hz, 1H), 4.50-4.40 (m, 3H), 4.07 (t, J=10.0 Hz, 1H), 3.94 (br s, 2H), 3.57-3.51 (m, 2H), 3.30 (s, 3H), 3.18 (t, J=6.9 Hz, 2H), 2.86-2.79 (m, 2H), 2.13-2.06 (m, 2H), 1.93 (t, J=6.9 Hz, 2H), 1.54-1.50 (m, 2H); LRMS (M+H) m/z 620.5.

$^1$H nmr (400 MHz, CDCl$_3$) δ 8.08 (1H, d, J Hz, NH), 7.29-7.19 (5H, m, C$_6$H$_5$), 7.04 (1H, d, J 9.0 Hz, oxobenzoxazapineH-6), 6.74 (1H, dd, J 9.0, 2.5 Hz, oxobenzoxazapineH-7), 6.68 (1H, d, J 2.5 Hz, oxobenzoxazapineH-9), 5.06 (1H, dt, J 11.0, 7.5 Hz, oxobenzoxazapineH-3), 4.67 (1H, dd, J 10.0, 7.5 Hz, 1H of oxobenzoxazapineH-2), 4.21 (1H, dd, J 11.0, 10.0 Hz, 1H of oxobenzoxazapineH-2), 4.13 (2H, s, CH$_2$C$_6$H$_5$), 3.70, 3.68 (4H, 2d AB system, J 5.5 Hz, pyranH-2, H-6), 3.34 (3H, s, NCH$_3$), 3.20, 3.18 (4H, 2d AB system, J 5.5 Hz, piperidineH-2, H-6), 1.70-1.68 (4H, m, piperidineH-3, H-5), 1.56-1.53 (4H, m, pyranH-3, H-5); m/z: 531 [M+H]$^+$ (found [M+H]$^+$, 531.2711, C$_{29}$H$_{34}$N$_6$O$_4$ requires [M+H]$^+$ 531.2714).

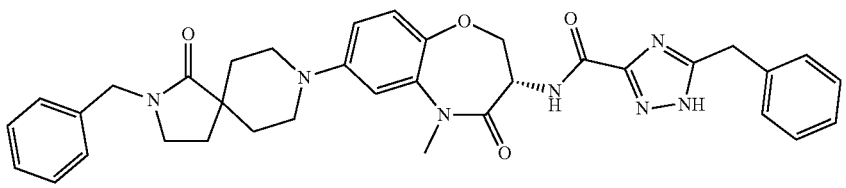 [SMILES: CN1C(=O)[C@@H](NC(=O)c2n[nH]c(Cc3ccccc3)n2)COc2ccc(N3CCC4(CCN(Cc5ccccc5)C4=O)CC3)cc21]

(S)-5-benzyl-N-(7-(2-benzyl-1-oxo-2,8-diazaspiro[4.5]decan-8-yl)-5-methyl-4-oxo-2,3,4,5-tetrahydrobenzo[b][1,4]oxazepin-3-yl)-1H-1,2,4-triazole-3-carboxamide $^1$H NMR (400 MHz, Chloroform-d) δ 8.03-7.93 (m, 1H), 7.34-7.23 (m, 4H), 7.21-7.18 (m, 2H), 7.14-7.09 (m, 5H), 6.96 (br d, J=8.8 Hz, 1H), 6.72 (br d, J=8.9 Hz, 1H), 6.65 (br s, 1H), 4.94 (t, J=9.2 Hz, 1H), 4.50-4.40 (m, 3H), 4.07 (t, J=10.0 Hz, 1H), 3.94 (br s, 2H), 3.57-3.51 (m, 2H), 3.30 (s, 3H), 3.18 (t, J=6.9 Hz, 2H), 2.86-2.79 (m, 2H), 2.13-2.06 (m, 2H), 1.93 (t, J=6.9 Hz, 2H), 1.54-1.50 (m, 2H); LRMS (M+H) m/z 620.5.

at 150 nM was combined with ATP working stock at equal volume and 2 ul/well were added to the 384 well plate. The final reaction volume was 5.0 μl.

The plate was quickly centrifuged and the reaction was incubated at 30° C. for 30 minutes. Adding 5 μl of ADP-Glo™ terminated the reaction. The plate was quickly centrifuged and the reaction was incubated at room temperature for 40 minutes. Kinase Detection Reagent was then added and incubated at room temperature for 30 minutes. The relative light unit (RLU) of kinase reaction was determined by luminescent (Luminescence 0.1s) using a Wallac Victor2 Luminometer (PerkinElmer, Waltham, Mass., USA). IC$_{50}$ values obtained from this example are provided by Table 1.

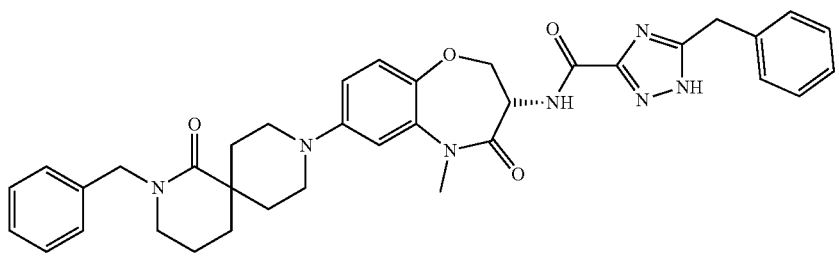

(S)-5-benzyl-N-(7-(2-benzyl-1-oxo-2,9-diazaspiro[5.5]undecan-9-yl)-5-methyl-4-oxo-2,3,4,5-tetrahydrobenzo[b][1,4]oxazepin-3-yl)-1H-1,2,4-triazole-3-carboxamide $^1$H NMR (400 MHz, Chloroform-d) δ 8.00-7.83 (m, 1H), 7.31-7.17 (m, 6H), 7.06-7.04 (m, 5H), 6.91 (br d, J=8.8 Hz, 1H), 6.66 (br d, J=9.0 Hz, 1H), 6.59 (br s, 1H), 4.93-4.87 (m, 1H), 4.54 (br s, 2H), 4.38 (br s, 1H), 4.08-3.98 (m, 1H), 3.86 (br s, 2H), 3.45-3.39 (m, 2H), 3.24 (br s, 2H), 3.19 (br s, 3H), 2.95-2.88 (m, 2H), 2.37-2.30 (m, 2H), 1.80-1.77 (m, 4H), 1.61-1.58 (m, 2H); LRMS (M+H) m/z 634.5.

Example 15

In this example, compounds of the disclosure were evaluated using a biochemical assay using the ADP-Glo™ technology.

ADP-Glo™ (Promega, Madison, Wis., USA) reagents were thawed at ambient temperature. Kinase Detection Reagent was prepared by mixing kinase detection buffer with the lyophilized kinase detection substrate.

A 500 ml stock volume of 5× Reaction Kinase Buffer was made by mixing 1000 μl of 1M MgCl$_2$, 500 μl of 1M Tris-HCL pH7.4, 0.5 mg/ml (25 mg) of BSA, and 3475 μl of distilled H$_2$O. A 3m 2× working stock volume of Reaction Kinase Buffer was made containing a final concentration of 100 μM DTT and 4 mM MnC$_2$.

Components of RIPK1 enzyme (Rigel Pharmaceuticals, South San Francisco, Calif., USA) were thawed on ice. Diluted RIPK1 was prepared in 1× Kinase Reaction Buffer (diluted from 2× buffer) to 31 ng/well. A 166 M working stock ATP assay solution was prepared in 1× Kinase Reaction Buffer (diluted from 2× buffer).

Compounds were serially diluted in DMSO from 250 uM in 4-fold dilutions then diluted 1:5 in 2× Reaction Buffer in a 96 well plate. 1.0 ul of diluted compound was added to a 384 well plate in duplicate. 2 μl of diluted Active RIPK1 was added to 384 well plate (do not add to column1) add 2×rxn buffer to column 1. AKT (Anaspec, Fremont, Calif., USA)

TABLE 1

| Compound | RIP1 ADP-Glo™ Kinase (IC$_{50}$) |
|---|---|
| I-1 | 0.1977 |
| I-2 | 0.0522 |
| I-3 | 0.0374 |
| I-4 | 0.0601 |
| I-5 | 0.0678 |
| I-6 | 0.0609 |
| I-7 | 0.1075 |
| I-8 | 0.2546 |
| I-9 | 0.0392 |
| I-10 | 0.3547 |
| I-11 | 0.0394 |
| I-12 | 0.0146 |
| I-13 | 0.0145 |
| I-14 | 0.4857 |
| I-15 | 0.0425 |
| I-16 | 0.2219 |
| I-17 | 0.0404 |
| I-18 | 0.088 |
| I-19 | 0.0623 |
| I-20 | 0.0482 |
| I-21 | 0.0377 |
| I-22 | 0.0236 |
| I-23 | 0.0697 |
| I-24 | 0.0745 |
| I-25 | 0.082 |
| I-26 | 0.0164 |
| I-27 | 0.0432 |

Example 16

In this example, U937 and L929 cells were exposed to compounds of the present disclosure and a cell necroptosis assay was conducted to evaluate the compounds' activity against human RIP1 and murine RIP1.

U937 and L929 cells were obtained from the American Type Culture Collection (Manassas, VA, USA). Both cells were maintained in logarithmic growth phase in complete RPMI 1640 media (Sigma, ST Louis, MO, USA) supplemented with 10% fetal bovine serum (Sigma, ST Louis, MO, USA) at 37° C. with 5% CO$_2$. For necroptosis assay, L929 cells were plated for 18h in 100 L/well medium at 10K cells/well in Costar 96-well black clear-bottom plates (Fisher Scientific, Hampton, NH, USA); U937 cells were plated on the day of the assay in 50 L/well medium containing 60 uM zVAD-fmk (Lonza, Basel, Switzerland) at 50K cells/well. Medium from L929 cells were removed from the 96-well plates and replaced with 50 L/well new medium containing 40 uM zVAD-fmk. Each compound of the present disclosure evaluated in this example was serially diluted in DMSO from 2.5 mM in 4-fold dilutions, and then diluted 1:125 in complete medium. 50 L/well 2× of the compound was then added to the cells in the plates. The cells were pre-incubated with the compound for 1 hour at 37° C. with 5% $CO_2$ and before addition of 10 L/well 11×TNFa (Peprotech, Rocky Hill, NJ, USA) to give a final concentration of 2 ng/mL for TNFa. The relative amount of necroptosis cells was determined by luminescent using a Wallac Victor2 Luminometer (PerkinElmer, Waltham, MA, USA) and a CellTiter-Glo® Luminescent Cell Viability Reagent Assay (Promega, Madison, WI, USA) added per manufacturer instructions after 18 hours of TNFa stimulation at 37° C. with 5% $CO_2$. Results from this example are summarized in Table 2. This example establishes that embodiments of the compounds described herein have unexpectedly potent activity against human RIP1 and murine RIP1, which allows their assessment in in vivo mouse models of disease. These results are useful in determining safe and effective doses for humans.

TABLE 2

| Compound | L929-CTG-recovery, L929, TNFa+zVAD ($IC_{50}$) | U937 Zvad TNF CTG Recovery, U937, TNFa+zVAD ($IC_{50}$) |
|---|---|---|
| I-1 | 0.5562 | 0.0123 |
| I-2 | 0.1244 | 0.004 |
| I-3 | 0.2211 | 0.0007 |
| I-4 | 0.2095 | 0.0032 |
| I-5 | 0.3589 | 0.0035 |
| I-6 | 11.49 | 0.0273 |
| I-7 | 2.493 | 0.0194 |
| I-8 | 1.487 | 0.0089 |
| I-9 | 4.128 | 0.0111 |
| I-10 | 7.285 | 0.0275 |
| I-11 | 0.4957 | 0.0121 |
| I-12 | 5.167 | 0.0095 |
| I-13 | 1.833 | 0.0063 |
| I-14 | 21.34 | 0.2197 |
| I-15 | 5.644 | 0.0695 |
| I-16 | 5005 | 0.7679 |
| I-17 | 1.862 | 0.0034 |
| I-18 | 0.3418 | 0.003 |
| I-19 | 0.9041 | 0.0065 |
| I-20 | 4.626 | 0.0068 |
| I-21 | 0.2673 | 0.0019 |
| I-22 | 0.1422 | 0.0029 |
| I-23 | 0.2354 | 0.0021 |
| I-24 | 0.1044 | 0.0016 |
| I-25 | 0.2007 | 0.0032 |
| I-26 | 5.586 | 0.013 |
| I-27 | 2.679 | 0.0211 |

Example 17

In this example, an acute hypothermia mouse model assay was used to evaluate the ability of compounds disclosed herein to inhibit TNF-alpha induced hypothermia.

Female C57BL/6 mice are randomly grouped and weighed on Day-1. On the day of the study (Day 0), mice are administered vehicle or test article by oral gavage. Fifteen minutes after oral administration of test agents, each mouse is administered an intraperitoneal (IP) injection of solution containing recombinant human tumor necrosis factor alpha (TNF-α, 25.0 µg) and zVAD-FMK (200 µg). Body temperature is measured at hour zero (before IP injections) and every hour via rectal probe temperature measuring device. Three (3) hours after IP injections of TNF-α and zVAD/FMK, mice are euthanized by $CO_2$ asphyxiation and blood is collected via cardiac puncture. Serum and plasma are harvested for determination of cytokine and compound levels, respectively. Separate groups of mice (satellite mice) are included for the determination of compound levels in plasma at the time of administration of TNFa/zVAD-FMK.

(S)-5-benzyl-N-(5-methyl-4-oxo-2,3,4,5-tetrahydrobenzo[b][1,4]oxazepin-3-yl)-4H-1,2,4-triazole-3-carboxamide (WO 2014/125444), having a structure as illustrated below, was used as a comparative compound and was examined using the same assay protocol. This comparative compound exhibited only 70% inhibition at 30 mg/kg. In comparison, compound 1-5 of the present disclosure achieved 81% inhibition at 15 mg/kg.

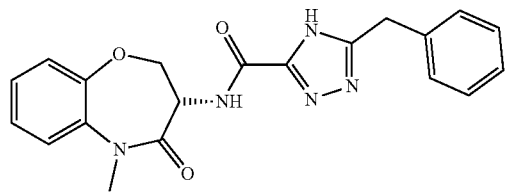

Comparative Compound

In view of the many possible embodiments to which the principles of the present disclosure may be applied, it should be recognized that the illustrated embodiments are only preferred examples and should not be taken as limiting. Rather, the scope of the present disclosure is defined by the following claims. We therefore claim as our invention all that comes within the scope and spirit of these claims.

We claim:

1. A method, comprising contacting a receptor-interacting protein-1 (RIP1) kinase in a subject with a compound, a pharmaceutically acceptable salt thereof, or both the compound and the pharmaceutically acceptable salt thereof; or a pharmaceutical composition comprising the compound and/or the pharmaceutically acceptable salt thereof, and wherein the compound has a formula

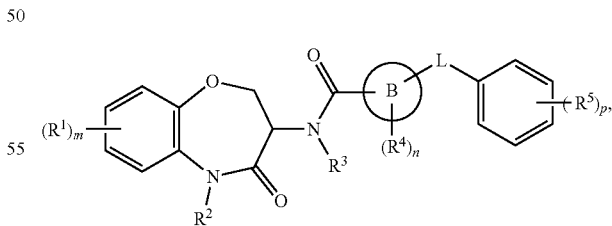

or a pharmaceutically acceptable salt thereof, wherein:
ring B is 5-membered heteroaryl;
L is a $C_{1-10}$aliphatic linker;
$R^1$ is $R^a$ or $R^b$ wherein at least one $R^1$ is $R^b$;
each of $R^2$ and $R^3$ independently are $R^a$;
each $R^4$ and each $R^5$ independently are $R^a$ or $R^b$;
$R^a$ is independently for each occurrence H, D, $C_{1-10}$aliphatic, or $C_{1-10}$cycloaliphatic;

$R^b$ is independently for each occurrence halogen or —$NR^dR^d$ wherein two $R^d$ groups together with the nitrogen bound thereto provide a $C_{3-10}$heterocyclic group optionally substituted with one or more $R^e$ or $R^g$;

$R^e$ is independently for each occurrence —$OR^a$, —$N(R^a)_2$, $C_{1-6}$ alkyl, $C_{1-6}$ haloalkyl, $C_{1-6}$heteroalkyl, $C_{3-6}$ cycloalkyl, or two $R^e$ groups join together to provide a $C_{3-10}$heterocyclic group with the Rb group to which the two $R^e$ groups are bound;

$R^g$ is independently for each occurrence halogen, $C_{1-10}$aliphatic-$C_{5-10}$aromatic, or =O m is 1 to 4;
n is 0, 1 or 2; and
p is 0, 1, 2, 3, 4, or 5,
wherein the subject has a disease involving a receptor-interacting protein-1 (RIP1) kinase, wherein the diseases involving a receptor-interacting protein-1 (RIP1) kinase is ankylosing spondylitis, rheumatoid arthritis, atopic dermatitis, psoriasis, or any combination thereof.

2. The method of claim 1, wherein the disease involving the RIP1 kinase is ankylosing spondylitis.

3. The method of claim 1, wherein the disease involving the RIP1 kinase is rheumatoid arthritis.

4. The method of claim 1, wherein the disease involving the RIP1 kinase is atopic dermatitis.

5. The method of claim 1, wherein the disease involving the RIP1 kinase is psoriasis.

6. The method of claim 1, wherein the compound has a structure satisfying a formula

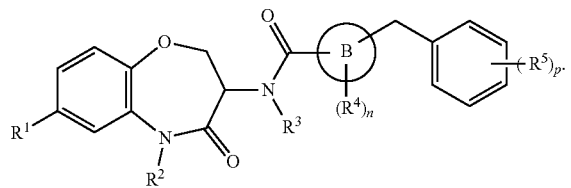

7. The method of claim 1, wherein ring B has a structure satisfying a formula

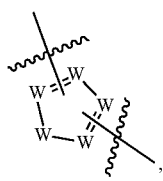

wherein at least one W is nitrogen, and each remaining W independently is selected from carbon, CH, oxygen, sulfur, nitrogen, or NH.

8. The method of claim 1, wherein ring B is a triazole selected from

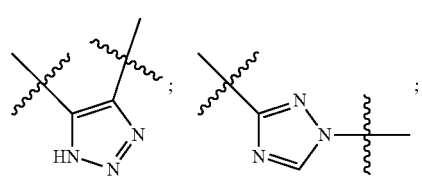

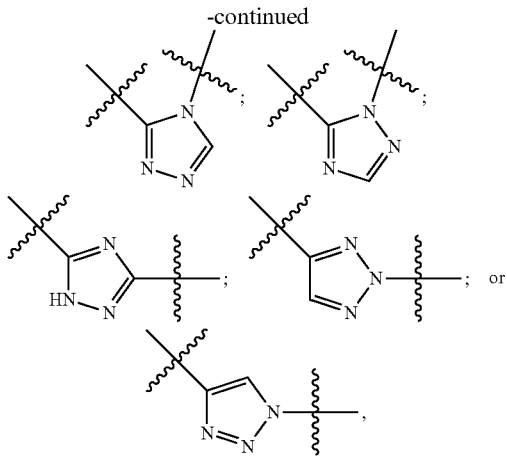

or an oxazole selected from

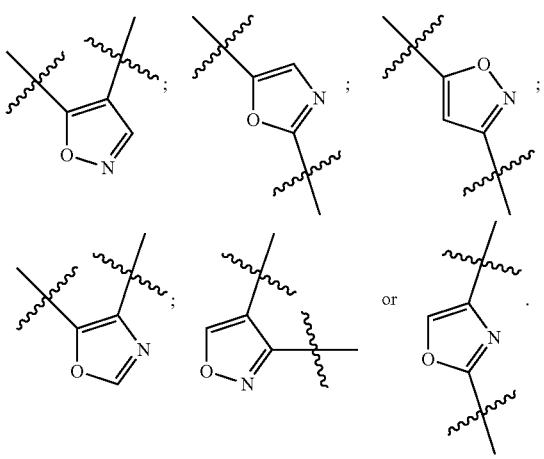

9. The method of claim 1, wherein $R^5$ is $R^a$, wherein $R^a$ is $C_1$-$C_4$aliphatic, and/or wherein $R^2$ is $R^a$ wherein $R^a$ is $C_1$-$C_4$ aliphatic and $R^3$ is $R^a$, wherein $R^a$ is hydrogen.

10. The method of claim 1, wherein $R^1$ is $R^b$ wherein $R^b$ is —$NR^dR^d$ wherein two $R^d$ groups together with the nitrogen bound thereto provide a $C_{3-10}$ heterocyclic group comprising two $R^e$ groups that join together to provide a second $C_{3-10}$ heterocyclic group.

11. The method of claim 10, wherein the second $C_{3-10}$ heterocyclic formed by the two $R^e$ groups and the $C_{3-10}$ heterocyclic formed by the two $R^d$ groups of $R^b$ provide a spirocyclic group or a bicyclic group.

12. The method of claim 11, wherein the spirocyclic group comprises greater than 7 total atoms in the spirocyclic system.

13. The method of claim 10, wherein the $C_{3-10}$ heterocyclic formed by the two $R^e$ groups and the $C_{3-10}$ heterocyclic formed by the two $R^d$ groups of $R^b$ provide a bicyclic group and the bicyclic group comprises two or more heteroatoms in the bicyclic group.

14. The method of claim 13, wherein the bicyclic group is a fused bicyclic group or a bridged bicyclic group and wherein the bicyclic group is attached to the compound through a nitrogen atom of the bicyclic group.

15. The method of claim 1, wherein R¹ is
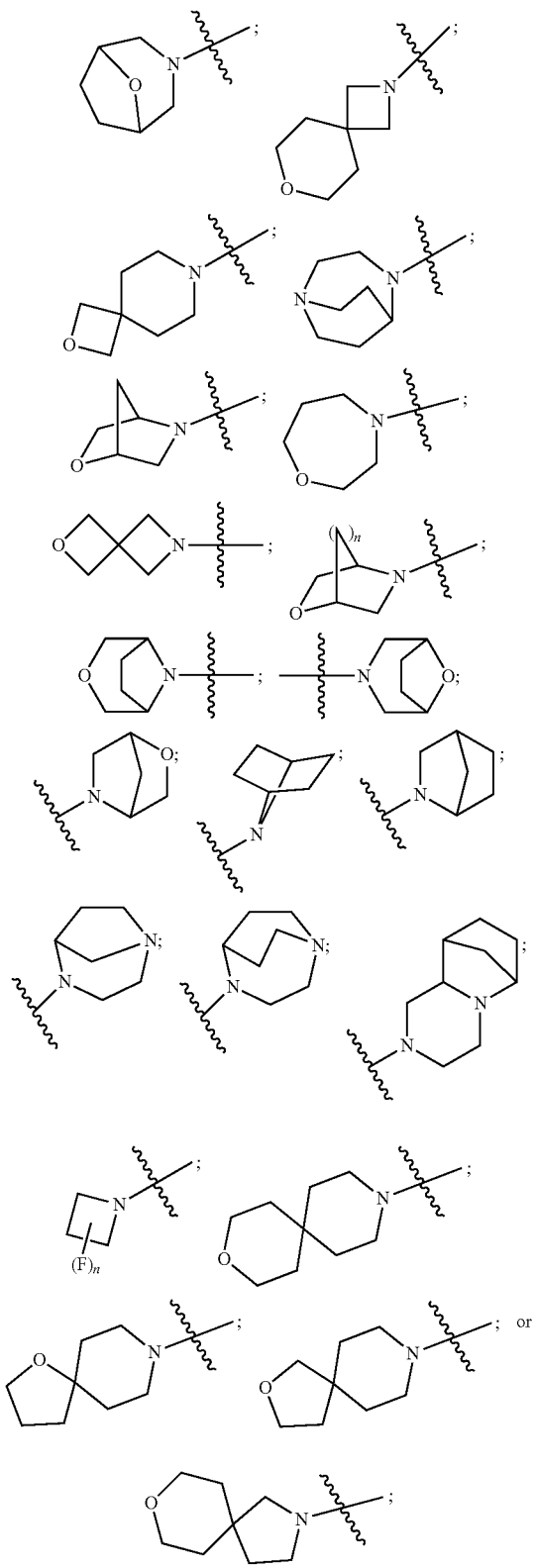
wherein each n independently is an integer ranging from 0 to 2.
16. The method of claim 1, wherein the compound is selected from
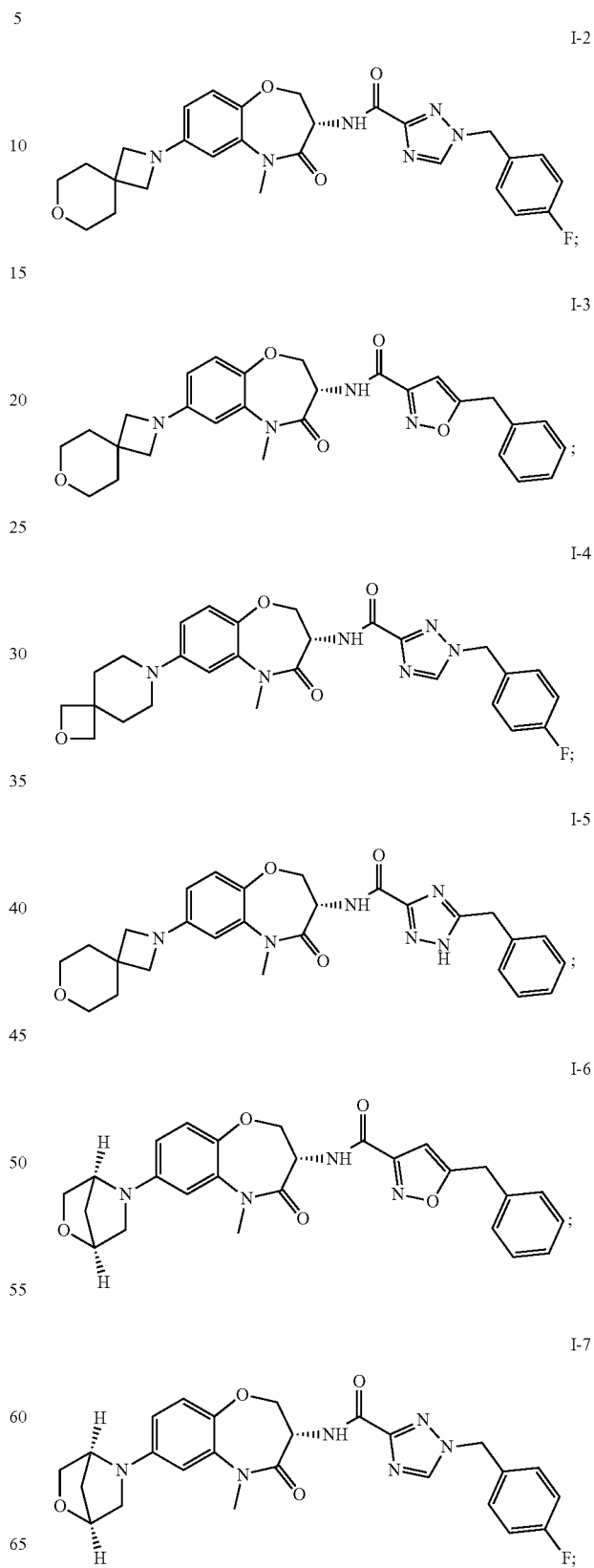

I-8
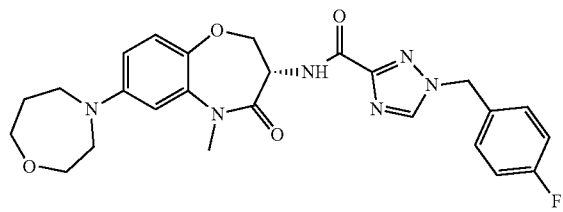
I-9
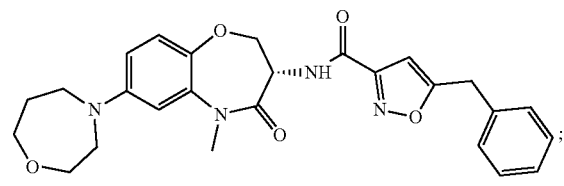
I-10
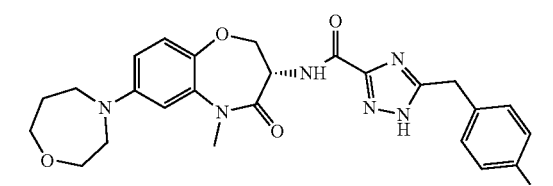
I-11
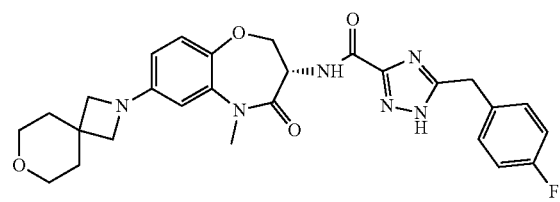
I-12
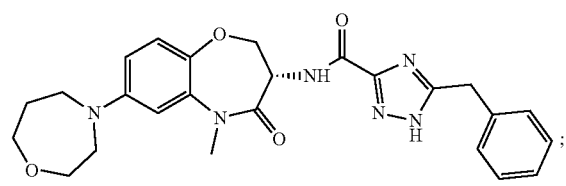
I-13
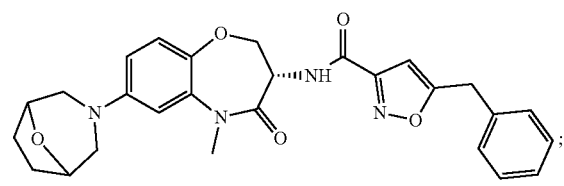
I-14
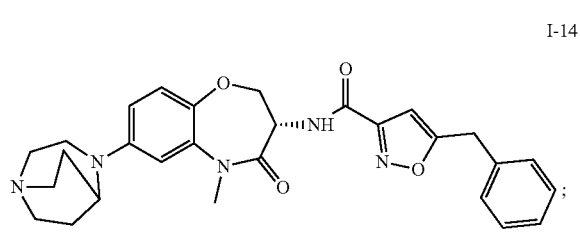
I-15
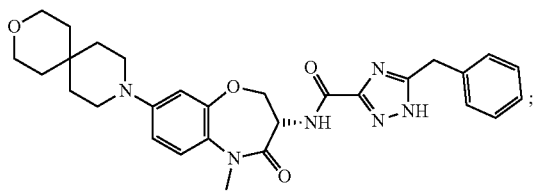
I-16
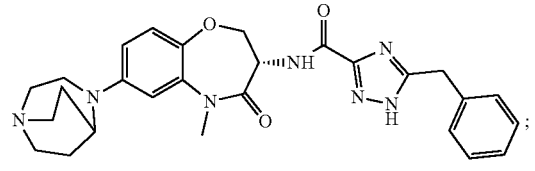
I-18
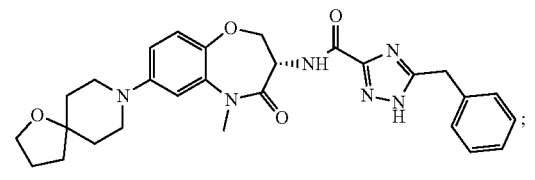
I-19
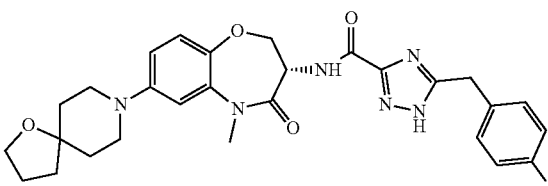
I-20
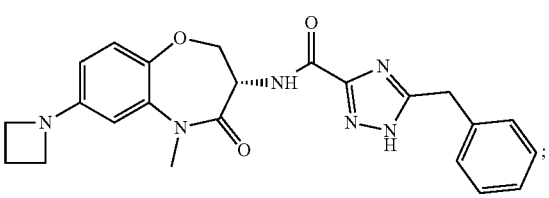
I-21
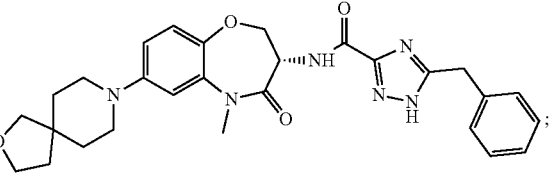
I-22
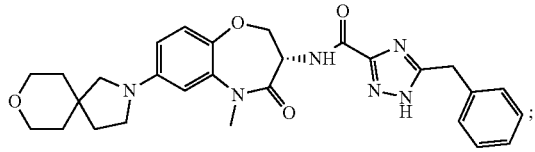

-continued
I-25
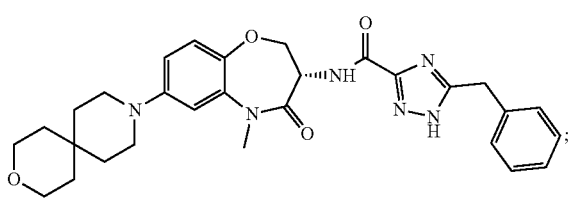;
I-26
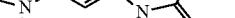; or
I-27
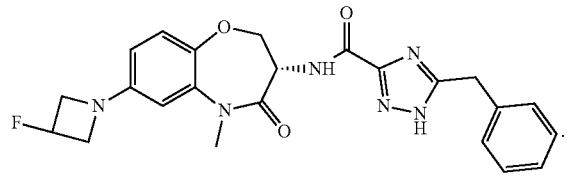.
17. The method of claim 1, wherein the compound is
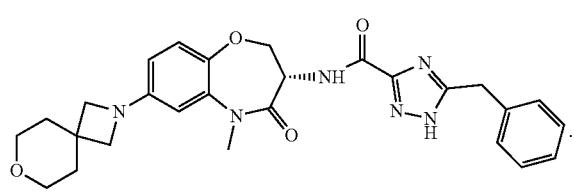 [SMILES: CN1C(=O)[C@@H](NC(=O)c2n[nH]c(Cc3ccccc3)n2)COc2ccc(N3CC4(CCOCC4)C3)cc21].
18. The method of claim 1, wherein the compound is
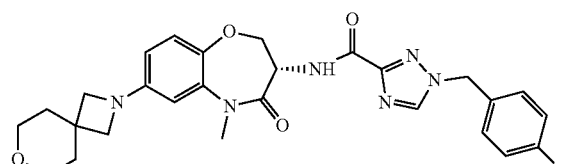.
* * * * *

UNITED STATES PATENT AND TRADEMARK OFFICE
CERTIFICATE OF CORRECTION

PATENT NO. : 11,919,890 B2
APPLICATION NO. : 17/210261
DATED : March 5, 2024
INVENTOR(S) : Vanessa Taylor et al.

It is certified that error appears in the above-identified patent and that said Letters Patent is hereby corrected as shown below:

On the Title Page

Item [73] delete ",Eli" and insert -- Eli --

In the Claims

Column 79, Line 10, Claim 1 delete "Rb" and insert -- $R^b$ --

Column 79, Line 23, Claim 2 delete "RIP'" and insert -- RIP1 --

Column 79, Line 27, Claim 5 delete "RIP'" and insert -- RIP1 --

Signed and Sealed this
Fourth Day of June, 2024

Katherine Kelly Vidal
*Director of the United States Patent and Trademark Office*